US011396509B2

(12) United States Patent
Asselin et al.

(10) Patent No.: US 11,396,509 B2
(45) Date of Patent: Jul. 26, 2022

(54) SOLID FORMS OF A TOLL-LIKE RECEPTOR MODULATOR

(71) Applicant: Gilead Sciences, Inc., Foster City, CA (US)

(72) Inventors: Sylvie M. Asselin, Broomfield, CO (US); Henry G. Morrison, Dublin, CA (US)

(73) Assignee: Gilead Sciences, Inc., Foster City, CA (US)

( * ) Notice: Subject to any disclaimer, the term of this patent is extended or adjusted under 35 U.S.C. 154(b) by 289 days.

(21) Appl. No.: 16/849,274

(22) Filed: Apr. 15, 2020

(65) Prior Publication Data

US 2020/0347051 A1 Nov. 5, 2020

Related U.S. Application Data

(60) Provisional application No. 62/835,359, filed on Apr. 17, 2019.

(51) Int. Cl.
| | | |
|---|---|---|
| *A61K 31/519* | (2006.01) | |
| *A61K 31/4375* | (2006.01) | |
| *C07D 471/04* | (2006.01) | |
| *A61P 31/20* | (2006.01) | |
| *A61K 31/675* | (2006.01) | |
| *A61K 31/683* | (2006.01) | |
| *A61K 31/708* | (2006.01) | |

(52) U.S. Cl.
CPC .......... *C07D 471/04* (2013.01); *A61K 31/519* (2013.01); *A61K 31/675* (2013.01); *A61K 31/683* (2013.01); *A61K 31/708* (2013.01); *C07B 2200/13* (2013.01)

(58) Field of Classification Search
CPC .............. A61K 31/519; A61K 31/4375; C07D 471/04; C07B 2200/13; A61P 31/20
USPC ................. 514/264.11, 264.1, 303; 546/118; 544/279
See application file for complete search history.

(56) References Cited

U.S. PATENT DOCUMENTS

| | | | |
|---|---|---|---|
| 2,512,572 A | 6/1950 | Smith, Jr. et al. |
| 2,581,889 A | 1/1952 | Timmis |
| 2,665,275 A | 1/1954 | Campbell et al. |
| 2,667,486 A | 1/1954 | Cain |
| 2,740,784 A | 4/1956 | Sletzinger et al. |
| 2,939,882 A | 6/1960 | Mecorney |
| 2,940,972 A | 6/1960 | Roch |
| 3,071,587 A | 1/1963 | Curran et al. |
| 3,081,230 A | 3/1963 | Weinstock et al. |
| 3,122,546 A | 2/1964 | Osdene |
| 3,159,628 A | 12/1964 | Pechter et al. |
| 3,162,635 A | 12/1964 | Schroeder |
| 3,475,425 A | 10/1969 | Roch |
| 3,843,791 A | 10/1974 | McFarland |
| 3,859,287 A | 1/1975 | Parish et al. |
| 4,438,128 A | 3/1984 | Wiedemann et al. |
| 4,608,383 A | 8/1986 | Wiedemann |
| 5,047,405 A | 9/1991 | Gennari |
| 5,064,833 A | 11/1991 | Ife et al. |
| 5,281,603 A | 1/1994 | Venkatesan et al. |
| 5,300,509 A | 4/1994 | Block et al. |
| 5,354,776 A | 10/1994 | Chandraratna |
| 5,380,724 A | 1/1995 | Zubovics et al. |
| 5,500,428 A | 3/1996 | Block et al. |
| 5,534,518 A | 7/1996 | Henrie |
| 5,641,783 A | 6/1997 | Klein et al. |
| 5,665,772 A | 9/1997 | Cottens et al. |
| 5,707,998 A | 1/1998 | Takase et al. |
| 5,780,462 A | 7/1998 | Lee et al. |
| 5,843,943 A | 12/1998 | Carson et al. |
| 5,866,572 A | 2/1999 | Barker et al. |
| 5,929,046 A | 7/1999 | McMurry et al. |
| 5,955,464 A | 9/1999 | Barker et al. |
| 5,992,713 A | 11/1999 | Manabat |
| 6,043,228 A | 3/2000 | McMurray et al. |
| 6,203,723 B1 | 3/2001 | Hsu |
| 6,331,547 B1 | 12/2001 | Zhu et al. |
| 6,440,991 B1 | 8/2002 | Zhu et al. |
| 6,559,149 B1 | 5/2003 | Matsuoka et al. |
| 6,844,343 B1 | 1/2005 | Ptleiderer et al. |
| 6,946,465 B2 | 9/2005 | Waer et al. |
| 7,074,801 B1 | 7/2006 | Yoshida et al. |
| 7,276,506 B2 | 10/2007 | Waer et al. |
| 7,501,513 B2 | 3/2009 | Waer et al. |
| 7,928,111 B2 | 4/2011 | Tachdjian et al. |
| 8,143,394 B2 | 3/2012 | Watkins et al. |
| 8,232,278 B2 | 7/2012 | De Jonghe et al. |
| 8,338,435 B2 | 12/2012 | Herdewijn et al. |

(Continued)

FOREIGN PATENT DOCUMENTS

| | | |
|---|---|---|
| CH | 231852 | 7/1944 |
| CN | 1583747 | 2/2005 |

(Continued)

OTHER PUBLICATIONS

Brown et al., Pteridine Studies. Part XIV. Methylation of 2-Amino-4-hydroxypteridine and Related Compounds, J. Chem. Soc., 1961, 869:4413-4420.

Kujime et al., Regioselective Preparation of Pterin 6-Triflate and Its Application to 6-Substituted Pterin Synthesis, Heterocycles, 2007, pp. 1841-1850, vol. 57.

Australian Patent Office, Examination Report No. 1 for Australian Patent Application No. 2016216673 dated Sep. 5, 2016, 7 pages.

Australian Patent Office, Examination Report No. 1 for Australian Patent Application No. 2016322763, dated Nov. 28, 2018, 5 pages.

(Continued)

*Primary Examiner* — Joseph R Kosack
*Assistant Examiner* — Sagar Patel
(74) *Attorney, Agent, or Firm* — Mintz, Levin, Cohn, Ferris, Glovsky and Popeo, P.C.

(57) ABSTRACT

The present disclosure provides solid forms, solvates and hydrates of (R)-2-((2-amino-7-fluoropyrido[3,2-d]pyrimidin-4-yl)amino)-2-methylhexan-1-ol, and methods of making.

27 Claims, 12 Drawing Sheets

(56) References Cited

U.S. PATENT DOCUMENTS

| | | |
|---|---|---|
| 8,367,670 B2 | 2/2013 | Desai et al. |
| 8,536,187 B2 | 9/2013 | Canales et al. |
| 8,541,421 B2 | 9/2013 | Tachdjian et al. |
| 8,633,186 B2 | 1/2014 | Tachdjian et al. |
| 8,637,531 B2 | 1/2014 | Bondy et al. |
| 8,673,929 B2 | 3/2014 | Gao et al. |
| 8,729,089 B2 | 5/2014 | Bondy et al. |
| 8,901,133 B2 | 12/2014 | Ren et al. |
| 8,916,575 B2 | 12/2014 | McGowan et al. |
| 8,969,363 B2 | 3/2015 | Castro et al. |
| 9,181,276 B2 | 11/2015 | Tachdjian et al. |
| 9,259,426 B2 | 2/2016 | Gao et al. |
| 9,603,848 B2 | 3/2017 | Servant et al. |
| 9,670,205 B2 | 6/2017 | Aktoudianakis et al. |
| 10,144,736 B2 | 12/2018 | Herdewijn et al. |
| 10,285,990 B2 | 5/2019 | Aktoudianakis et al. |
| 10,370,342 B2 | 8/2019 | Chin et al. |
| 10,640,499 B2 | 5/2020 | Chin et al. |
| 10,882,851 B2 | 1/2021 | Gao et al. |
| 11,124,487 B2 | 9/2021 | Chin et al. |
| 2003/0236255 A1 | 12/2003 | Waer et al. |
| 2004/0030156 A1 | 2/2004 | Maul |
| 2004/0038856 A1 | 2/2004 | Chakravarty et al. |
| 2004/0102447 A1 | 5/2004 | Bonnert et al. |
| 2004/0167121 A1 | 8/2004 | Aronov et al. |
| 2004/0167198 A1 | 8/2004 | Wrasidlo et al. |
| 2005/0054626 A1 | 3/2005 | Carter et al. |
| 2005/0054653 A1 | 3/2005 | Eisenbrand et al. |
| 2005/0191238 A1 | 9/2005 | Casebier et al. |
| 2005/0282814 A1 | 12/2005 | Wrasidlo et al. |
| 2006/0116371 A1 | 6/2006 | Martyres et al. |
| 2007/0004721 A1 | 1/2007 | Waer et al. |
| 2007/0043000 A1 | 2/2007 | Waer et al. |
| 2007/0054916 A1 | 3/2007 | Patel et al. |
| 2007/0287704 A1 | 12/2007 | Dollinger et al. |
| 2008/0004285 A1 | 1/2008 | De Jonghe et al. |
| 2008/0027062 A1 | 1/2008 | Doblhofer et al. |
| 2008/0096883 A1 | 4/2008 | Caravatti et al. |
| 2008/0112884 A1 | 5/2008 | Casebier et al. |
| 2008/0182870 A1 | 7/2008 | Bondy et al. |
| 2008/0234251 A1 | 9/2008 | Doherty et al. |
| 2008/0306053 A1 | 12/2008 | Tachdjian et al. |
| 2008/0306093 A1 | 12/2008 | Servant et al. |
| 2008/0312227 A1 | 12/2008 | De Jonghe et al. |
| 2009/0036430 A1 | 2/2009 | De Jonghe et al. |
| 2009/0131414 A1 | 5/2009 | De Jonghe et al. |
| 2009/0253696 A1 | 10/2009 | Herdewijn et al. |
| 2009/0318456 A1 | 12/2009 | Herdewijn et al. |
| 2010/0029585 A1 | 2/2010 | Howbert et al. |
| 2010/0143299 A1 | 6/2010 | Gao et al. |
| 2010/1403301 | 6/2010 | Desai et al. |
| 2010/0305117 A1 | 12/2010 | Herdewijn et al. |
| 2011/0098248 A1 | 4/2011 | Halcomb et al. |
| 2011/0224155 A1 | 9/2011 | Zoller |
| 2011/0230502 A1 | 9/2011 | Tachdjian et al. |
| 2012/0122838 A1 | 5/2012 | Ren et al. |
| 2012/0238587 A1 | 9/2012 | Lee et al. |
| 2013/0029982 A1 | 1/2013 | Castro et al. |
| 2013/0109693 A1 | 5/2013 | Routier et al. |
| 2014/0235623 A1 | 8/2014 | Tachdjian et al. |
| 2016/0289229 A1 | 10/2016 | Aktoudianakis et al. |
| 2017/0071944 A1 | 3/2017 | Geleziunas et al. |
| 2018/0263985 A1 | 9/2018 | Geleziunas et al. |
| 2019/0152974 A1 | 5/2019 | Herdewijn et al. |
| 2020/0017451 A1 | 1/2020 | Chin et al. |
| 2020/0345738 A1 | 11/2020 | Asselin et al. |
| 2020/0347051 A1 | 11/2020 | Asselin et al. |
| 2021/0017170 A1 | 1/2021 | Aktoudianakis et al. |
| 2021/0276988 A1 | 9/2021 | Gao et al. |

FOREIGN PATENT DOCUMENTS

| | | |
|---|---|---|
| DE | 1921308 | 1/1971 |
| DE | 267495 | 5/1989 |
| DE | 4009941 | 10/1991 |
| EP | 0042593 | 12/1981 |
| EP | 0108890 | 5/1984 |
| EP | 0134922 | 3/1985 |
| EP | 0185259 | 6/1986 |
| EP | 0290819 | 11/1988 |
| EP | 0322133 | 6/1989 |
| EP | 0362645 | 4/1990 |
| EP | 0404322 A1 | 12/1990 |
| EP | 0404355 | 12/1990 |
| EP | 0544445 | 6/1993 |
| EP | 0574906 | 12/1993 |
| EP | 0837063 | 4/1998 |
| EP | 0956855 | 11/1999 |
| EP | 1144412 | 10/2001 |
| EP | 1382603 | 1/2004 |
| EP | 1479682 | 11/2004 |
| EP | 1724268 | 11/2006 |
| EP | 3097102 | 10/2017 |
| EP | 2709989 | 12/2017 |
| EP | 3321265 | 5/2018 |
| EP | 3349757 A1 | 7/2018 |
| GB | 677342 | 8/1952 |
| GB | 763044 | 12/1956 |
| GB | 785353 | 10/1957 |
| GB | 1301319 | 12/1972 |
| GB | 2143232 | 2/1985 |
| GB | 2405793 | 3/2005 |
| JP | H07138238 | 5/1995 |
| JP | 2000038350 | 2/2000 |
| JP | 2000053653 | 2/2000 |
| JP | 2000053654 | 2/2000 |
| WO | WO1993007124 | 4/1993 |
| WO | WO1993025712 | 12/1993 |
| WO | WO1994006431 | 3/1994 |
| WO | WO1994011001 | 5/1994 |
| WO | WO1994014065 | 6/1994 |
| WO | WO1994022449 | 10/1994 |
| WO | WO1994022855 | 10/1994 |
| WO | WO1994027439 | 12/1994 |
| WO | WO1995013075 | 5/1995 |
| WO | WO1995031469 | 11/1995 |
| WO | WO1995031987 | 11/1995 |
| WO | WO1995032203 | 11/1995 |
| WO | WO1996010568 | 4/1996 |
| WO | WO1996016960 | 6/1996 |
| WO | WO1996020710 | 7/1996 |
| WO | WO1997023616 | 7/1997 |
| WO | WO1997030034 | 8/1997 |
| WO | WO1997031920 | 9/1997 |
| WO | WO1997039358 | 10/1997 |
| WO | WO1998004558 | 2/1998 |
| WO | WO1998008516 | 3/1998 |
| WO | WO1998052948 | 11/1998 |
| WO | WO1999050264 | 10/1999 |
| WO | WO2000039129 | 7/2000 |
| WO | WO2000045800 | 8/2000 |
| WO | WO2001019825 | 3/2001 |
| WO | WO2001021619 | 3/2001 |
| WO | WO2002032507 | 4/2002 |
| WO | WO2003001887 | 1/2003 |
| WO | WO2003031406 | 4/2003 |
| WO | WO2003062240 | 7/2003 |
| WO | WO2004026307 | 4/2004 |
| WO | WO2004065392 | 8/2004 |
| WO | WO2004072033 | 8/2004 |
| WO | WO2004104005 | 12/2004 |
| WO | WO2005020899 | 3/2005 |
| WO | WO2005021003 | 3/2005 |
| WO | WO2005025574 | 3/2005 |
| WO | WO2005028444 | 3/2005 |
| WO | WO2005039587 | 5/2005 |
| WO | WO2005046698 | 5/2005 |
| WO | WO2005063752 | 7/2005 |
| WO | WO2005073204 | 8/2005 |
| WO | WO2005079391 | 9/2005 |
| WO | WO2005080377 | 9/2005 |
| WO | WO2005105761 | 11/2005 |
| WO | WO2006015859 | 2/2006 |
| WO | WO2006039718 | 4/2006 |

(56) References Cited

FOREIGN PATENT DOCUMENTS

| WO | WO2006050843 | 5/2006 |
|---|---|---|
| WO | WO2006058867 | 6/2006 |
| WO | WO2006058869 | 6/2006 |
| WO | WO2006069805 | 7/2006 |
| WO | WO2006120251 | 11/2006 |
| WO | WO2006135993 | 12/2006 |
| WO | WO2007093901 | 8/2007 |
| WO | WO2007135026 | 11/2007 |
| WO | WO2007135027 | 11/2007 |
| WO | WO2008003149 | 1/2008 |
| WO | WO2008009076 | 1/2008 |
| WO | WO2008009077 | 1/2008 |
| WO | WO-2008009078 A2 | 1/2008 |
| WO | WO-2008009079 A2 | 1/2008 |
| WO | WO2008009706 | 1/2008 |
| WO | WO2008024977 | 2/2008 |
| WO | WO2008030455 | 3/2008 |
| WO | WO2008077649 | 7/2008 |
| WO | WO2008077651 | 7/2008 |
| WO | WO2008154221 | 12/2008 |
| WO | WO2009003669 | 1/2009 |
| WO | WO2010002877 | 1/2010 |
| WO | WO2010002998 | 1/2010 |
| WO | WO2010042489 | 4/2010 |
| WO | WO2010046639 | 4/2010 |
| WO | WO2010092340 | 8/2010 |
| WO | WO2011057148 | 5/2011 |
| WO | WO2011072275 | 6/2011 |
| WO | WO2011097607 | 8/2011 |
| WO | WO2011135259 | 11/2011 |
| WO | WO2012058601 | 5/2012 |
| WO | WO2012136834 | 10/2012 |
| WO | WO2012156498 | 11/2012 |
| WO | WO2013012915 | 1/2013 |
| WO | WO2013060881 | 5/2013 |
| WO | WO2013090840 | 6/2013 |
| WO | WO2013117615 | 8/2013 |
| WO | WO2013174947 | 11/2013 |
| WO | WO2014116755 | 1/2014 |
| WO | WO2014023813 | 2/2014 |
| WO | WO2014056953 | 4/2014 |
| WO | WO2014076221 | 5/2014 |
| WO | WO2014078778 | 5/2014 |
| WO | WO2014120995 | 8/2014 |
| WO | WO2014128189 | 8/2014 |
| WO | WO2015014815 | 2/2015 |
| WO | WO2015168269 | 11/2015 |
| WO | WO2015191752 | 12/2015 |
| WO | WO2016141092 | 9/2016 |
| WO | WO2017048727 | 3/2017 |
| WO | WO2018002319 | 1/2018 |
| WO | WO-2018045144 A1 | 3/2018 |
| WO | WO-2018045150 A1 | 3/2018 |
| WO | WO-2020214652 A1 | 10/2020 |
| WO | WO-2020214663 A1 | 10/2020 |

OTHER PUBLICATIONS

Australian Patent Office, Examination Report No. 2 for Australian Patent Application No. 2016216673, dated Nov. 14, 2016, 3 pages.
Chilean Patent Office, Official Action for CL Patent Application No. 201702225, dated Nov. 9, 2018, 11 pages.
Dominican Patent Office, Office Action for DO Patent Application No. P2017-0203, dated Oct. 8, 2020, with English translation, 4 pages.
European Patent Office, Examination Report For EP Patent Application No. 16711723.3, dated Nov. 29, 2016.
European Patent Office, International Preliminary Reporton Patentability for International Application No. PCT/BE2007/000092, dated Apr. 7, 2007.
European Patent Office, International Preliminary Reporton Patentability for International application No. PCT/BE2007/000091, dated Jan. 20, 2009, 14 pages.
European Patent Office, International Preliminary Reporton Patentability for International Patent Application No. PCT/US2017/049562, dated Mar. 5, 2019, 7 pages.
European Patent Office, International Preliminary Reporton Patentability for PCT International Patent Application No. PCT/US2017/049573, dated Mar. 5, 2019, 7 pages.
European Patent Office, International Search Report and Written Opinion for International Application No. PCT/US2016/020499, dated Jul. 25, 2016, 18 pages.
European Patent Office, International Search Report and Written Opinion for International Application No. PCT/BE2007/000091, dated Nov. 11, 2008, 9 pages.
European Patent Office, International Search Report and Written Opinion for International Application No. PCT/US2017/049562, dated Nov. 14, 2017, 11 pages.
European Patent Office, International Search Report and Written Opinion for International Application No. PCT/US2017/049573, dated Oct. 25, 2017, 12 pages.
European Patent Office, International Search Report and Written Opinion for International Application No. PCT/US2016/051545, dated Dec. 8, 2016, 13 pages.
Gulf Cooperation Council Patent Office, Examination Report for GC Application No. GC 2016-30932, dated Jul. 6, 2020, 4 pages.
Israel Patent Office, Office Action for IL Application No. 254164, dated Sep. 21, 2020, 2 pages.
Korean Patent Office, Notice of Preliminary Rejection for Korean Patent Application No. 10-2016-7023289, dated Oct. 14, 2016, with English translation, 9 pages.
Korean Patent Office, Search Report for Korean Patent Application 10-2016-7023289, dated Aug. 25, 2016 with English translation, 14 pages.
Mexico Patent Office, Notice of Allowance for MX Application No. MX/a/2017011307, dated Oct. 14, 2020, 2 pages.
Ukraine Patent Office, Notice of Allowance for UA Application No. a210708923, dated Nov. 5, 2020, 17 pages.
USPTO, Office Action for U.S. Appl. No. 15/264,401, dated Dec. 27, 2016, 11 pages.
USPTO, Office Action for U.S. Appl. No. 12/374,242, dated Apr. 9, 2012, 20 pages.
Schlaepfer et al., "TLR8 Activates HIV from Latently Infected Cells of Myeloid-monocytic Origin Directly via the MAPK Pathway and from Latently Infected CD4+ T Cells Indirectly via TNF-α", Journal of Immunology, 2011, 186(7):4314-4324.
European Patent Office, International Search Report and Written Opinion received for PCT/US2020/028237 dated Jun. 30, 2020, 8 pages.
European Patent Office, International Search Report and Written Opinion for PCT/US2020/028257 dated Jun. 26, 2020, 8 pages.
Abou-Hedeed, et al., Pteridines CVIII Reactions of 6, 7-Dichloro-1, 3-Dimethyllumazine with Sulfur-Nucleophiles, Pteridines, 1996, pp. 113-122, vol. 7.
Armarego et al., Quinazolines. Part IX. Covalent hydration in the neutral species of substituted quinazolines, J. Chem. Soc. B: Phys. Org., 1967, pp. 449-454.
Baba et al., Synergistic Antiviral Effects of Antiherpes Compounds and Human Leukocyte Interferon on Varicella-Zoster Virus in Vitro, Antimicrob. Agents Chemother., 1984, pp. 515-517, vol. 25.
Banker et al. (eds.), Modern Pharmaceutics: Third Edition, Revised and Expanded, Marcel Dekker, Inc., 1996, pp. 451 and 596.
Barl, et al., The Halogen/Magnesium-Exhange using iPrMgCl•LiCl and related exchange reagents, Heterocycles, 2014, pp. 827-844.
Beers et al. (eds), The Merck Manual of Diagnosis and Therapy, Merck Research Laboratories: Whitehouse Station, N.J., Leukemias, 1999, pp. 953-954, Chapter 138.
Beers et al. (eds), The Merck Manual of Diagnosis and Therapy, Merck Research Laboratories: Whitehouse Station, N.J., Neurologic Disorders, 1999, pp. 1474-1476, Sec. 14.
Bennett, et al., Cecil Textbook of Medicine, 20th Ed., 1996, pp. 1004-1010, vol. 1.
Bennett, et al., Cecil Textbook of Medicine, 20th Ed., 1996, pp. 1992-1996, vol. 2.
Bennett, et al., Cecil Textbook of Medicine, 20th Ed., 1996, pp. 2050-2057, vol. 2.

(56) References Cited

OTHER PUBLICATIONS

Bigorgne et al., TLRs in Hepatic Cellular Crosstalk, Gastroenterology Research and Practice, 2010, pp. 1-7, Article ID 618260.
Black et al., Agents that Block TNF-a Synthesis or Activity, 1997, Ann. Rep. Med. Chem., pp. 241-250, vol. 32.
Boon, Pteridines. Part IV.' Derivatives of 2:4-Diaminopteridine and Related Compounds, J. Chem. Soc., 1957, pp. 2146-2158.
Buitendijk, et al., Toll-Like Receptor Agonists are Potent Inhibitors of Human Immunodeficiency Virus-Type 1 Replication in Peripheral Blood Mononuclear Cells, AIDS Research and Human Retroviruses, May 1, 2014, pp. 457-467, vol. 30, No. 5.
Bundgaard (ed.). Design of Prodrugs, 1985, p. 1.
Buu-Hoi et al., Phthalonimides (1,3,4-Trioxo-1,2,3,4-Tetrahydroisoquinolines) of Potential Biological Interest, J. Heretocyclic Chem., 1968, pp. 545-546, vol. 5.
Cairo, Immunology Lecture #20: Transplantation, Columbia University [online] 2003, Retrieved Jul. 12, 2005 from http://healthsciences.columbia.edu/dept/ps/2007/immuno/2006/IM20.pdf (6 pages).
Cervantes, J. et al., TLR8: the forgotten relatuve revindicated, Cellular & Molecular Immunology, 2012, pp. 434-438, vol. 9.
Chantry, Tumour Necrosis Factor Antagonists, Exp. Op. Emerging Drugs, 1999, pp. 5-13, Ch. 1.
Chapman, N. et al., Synthethic Antimalarials. Part XVI. 4-Dialkylaminoalkylaminoquinazolines. Variation of Substituents in the 6- and 7-Positions, Journal of the Chemical Society, 1947, pp. 890-899.
Cho, Synthesis and antiviral activity of a series of 1'-substituted 4-aza-7,9-dideazaadenosince C-nucleosides, Bioorganic & Medicinal Chemistry Letters, 2012, pp. 2705-2707.
CHOU ei al., Quantitative Analysis of Dose-Effect Relationships: The Combined Effects of Multiple Drugs or Enzyme Inhibitors, Adv. Enzyme ReguL, 1984, pp. 27-55.
Cohen, The Development and Therapeutic Potential of Protein Kinase Inhibitors, Chemical Biology, 1999, pp. 459-465.
Colonna, M. et al., Plasmacytoid dendritic cells in immunity, Nature Immunology, 2004, 5(12)0:1219-1226.
Cottam et al., Substituted Xanthines, Pteridinediones and Related Compounds as Potential Anti-Inflammatory Agents. Synthesis and Biological Evaluation of Inhibitors of Tumor Necrosis Factor Alpha, J. Med. Chem. 1996, pp. 2-9, vol. 39.
Database Beilstein, Accession No. 1184281, Beilstein Institute for Organic Chemistry, ZA Pat No. 6706096, 1968. (XP-002324247, 2 pages).
Database Beilstein, Accession No. 7216143, Beilstein Institute for Organic Chemistry, HTCYAM Heterocycles EN 41:7811-788, 1995. (XP-002296937, 3 pages).
Database Beilstein, Accession No. 7928670, Beilstein Institute for Organic Chemistry, HTCYAM Heterocycles EN 48:1255-1274, 1998. (XP-002296938, 2 pages).
Database Beilstein, Accession Nos. 285496, 252276, and 250719, Beilstein Institute for Organic Chemistry, Angew. Chem. 73:695, 704, 1961; Ber. Bunsen-Ges. Phys. Chem. 69:458, 462, 465, 1965; Chem. Ber. 90:2631,2633, 2635, 1957; Chem. Ber. 95:755, 762, 1962; Chem. Ber. 106:3203, 3205, 1973; Chem. Ber. 114:699-706, 1981; Heterocycles 24:1565-1566, 1986; Heterocycles 41:781-788, 1995; J. Chem. Soc. Perkin Trans. 2:35-36, 1979; Justus Liebigs Ann. Chem. 547:180, 183, 1941; Liebigs Ann. Chem. 11:11798-1814, 1984; Zh. Org. Khim. RU 32:455-460, 1996. (XP-002296934, 22 pages).
Database Beilstein, Accession Nos. 533693 and 540145, Beilstein Institute for Organic Chemistry, CHBEAM Chem. Ber. 93: 2668, 2671, 1960. (XP-002296935, 4 pages).
Database Beilstein, Accession Nos. 6337777 and 6373242, Beilstein Institute for Organic Chemistry, KGSSAQ Khim. Geterotsikt Soedin. RU9: 1202-1207, 1992. (XP-002296933, 6 pages).
Database Beilstein, Accession Nos. 9571456 and 9570157, Beilstein Institute for Organic Chemistry, IASKEA Izv. Akad. Nauk. Ser. Khim. RU6:1328-1334, 2003. (XP-002296936,11 pages).
Database WPI Week 2005, Feb. 23, 2005, Thompson Scientific, London, GB (XP002498175).

Dempcy et al., Regioselective synthesis of imidazo[4,5-g]quinazoline quinone nucleosides and quinazoline amino nucleosides. Studies of their xanthine oxidase and purine nucleoside phosphorylase substrate activity, J. Org. Chem., 1991,776-85, vol. 56.
Dermer, Another Anniversary for the War on Cancer, Bio/Technology, Mar. 12, 1994, p. 320, vol. 12.
Deuis, Pharmacological characterization of the highly Nav1.7 selective spider venom peptide Pn3a, Scientific Reports, 2017, pp. 1-18.
Dimauro et al., Microwave-assisted preparation of fused bicyclic heteroaryl boronates: application in one-pot Suzuki couplings, J. Org. Chem., 2006, pp. 3959-3962.
Ding et al., Parallel Synthesis of Pteridine Derivatives as Potent Inhibitors for Hepatitis C Virus NS5B RNA-Dependent RNA Polymerase, Bioorg Med. Chem. Lett., 2005, pp. 675-678, vol. 15.
Elion et al., Antagonists of Nucleic Acid Derivatives. VIII. Synergism in Combinations of Biochemically Related Antimetabolites, J. Biol. Chem., 1954, pp. 477-488.
Elliott et al., Synthesis of N-10-Methyl-4-Thiofolic Acid and Related Compounds, J. Med. Chem., 1975, pp. 492-496, vol. 18
Freshney, Culture of Animal Cells, 1983, pp. 1-6, Chapter 1, Alan R. Liss, Inc.
Frohlich et al., Inhibition of Neuronal Nitric Oxide Synthase by 4-Amino Pteridine Derivatives: Structure-Activity Relationship of Antagonists of (6R)-5, 6, 7, 8-Tetrahydrobiopterin Cofactor, J. Med. Chem., 1999, pp. 4108-4121, vol. 42.
Ganellin, Final Report on the Activities of the Medicinal Chemistry Section, 2002, Retrieved Jun. 2, 2004 from www.iupac.org/divisions/VII/VII.M/VIIM-ReportDec2001.pdf (4 pages).
Gerlach et al., Influence of Pyrimidopyrimidine and Pteridine Derivatives on Phosphate and Adenosine Permeability in Human Erythrocytes, Arzneimittelforschung, 1965, pp. 558-563, vol. 15 (English Abstract).
Giori et al., Reactivity of 3H-Pyrimido[5, 4-c] [1, 2, 5] Oxadiazin-3-One Towards Carbanions: Synthesis of Pteridine-2, 4-Diones, J. Heterocyclic Chem., 1986, pp. 1661-1665, vol. 23.
Golub, et al., Molecular Classification of Cancer: Class Discovery and Class Prediction by Gene Expression Monitoring, Science, Oct. 15, 1999, pp. 531-537, vol. 286.
Gonzalez-Rodriguez, et al., Synergistic combinations of the dual enkephalinase inhibitor PL265 given orally with various analgesic compounds acting on different targets, in a murine model of cancer-induced bone pain, Scand J Pain, 2017, pp. 25-38.
Guillermo et al., Targeting cell cycle kinases for cancer therapy, Current Medicinal Chemistry, Apr. 1, 2007, pp. 969-985, vol. 14.
Hayakawa et al., Synthesis and Biological Evaluation of 4-Morpholino-2-Phenylquinazolines and Related Derivatives as Novel PI3 Kinase p110alpha Inhibitors, Bioorg. Med. Chem., 2006, pp. 6847-6858, vol. 14.
Hayden, Antimicrobial Agents (Continued) Antiviral Agents (Nonretroviral), Goodman and Gilman's The Pharmacological Basis for Therapeutics, 10th Edition, 2001, pp. 1313-1315, Chapter 50.
Higuchi et al., A Disproportionation of 6-Amino-5-Benzylideneamino-1,3-dimethyluracils in Formamide. Formation of 6,7-Diaryl-1,3-dimethyllumazines and Theophylline, Heterocycles, 1976, pp. 977-980, vol. 4.
Horner et al., Analogs of 3-amino-7-chloro-1,2,4-benzotriazine 1-oxide as antimalarial agents, J. Med. Chem., 1968, pp. 946-949, vol. 11.
Illei et al., Novel, Non-Antigen-Specific Therapeutic Approaches to Autoimmune/Inflammatory Diseases, Curr. Op. Immunol., 2000, pp. 712-718, vol. 12.
Isensee, Synergistic regulation of serotonin and opioid signaling contribute to pain insensitivity in Nav1.7 knockout mice, Neuroscience, Science Signaling, 2017, 11 pages.
Israel et al., Pyrimidine Derivatives. VII. Some Condensed Derivatives of 2, 4, 5-Triamino-6-Methylthiopyrimidine, J. Pharm. Sci., 1965, pp. 1626-1632, vol. 54.
Iwagaki et al., Decreased Serum Tryptophan In Patients With Cancer Cachexia Correlates With Increased Serum Neopterin, Immunot Investig., 1995, pp. 467-478, vol. 24.

(56) References Cited

OTHER PUBLICATIONS

Jackson et al., 6, 7-Disubstituted 2, 4-Diaminoteridines: Novel Inhibitors of Pneumocystis carinii and Toxoplasma gondii Dihydrofolate Reductase, Antimicrob. Agents Chemother., 1996, pp. 1371-1375, vol. 40.

Jo, et al., Toll Like Receptor 8 Agonist and Bacteria Trigger Potent Activation of Innate Immune Cells in Human Liver, PLOS Pathogens, Jun. 2014, 13 pages.

Kaczanowska, S. et al. (2013) "TLR agonists: our best frenemy in cancer immunotherapy" Journal of Leukocyte Biology 93(6):847-863.

Kaldrikyan et al., "Pteridine Derivatives. I. Synthesis of Some Substituted 6,7-Diarylpteridines," Armyanskii Khimicheskii Zhumat, 1976, 3 pages, vol. 29.

Kandror et al., Radical Arylation of N-Substituted Carboxylic Acid Thioamides and Cyclic Thioamides, Russ. Chem. Bull., 1982, pp. 1873-1876, vol. 31 (Abstract only).

Kikelj, From 2-Aminobenzonitriles and Carbon Dioxide, Carbon Monoxide, Carbon Disulfide, or Potassium 0-Ethyl Dithiocarbonate, Science of Synthesis, 2004, pp. 573-749, 2004.

Landauer et al., A Convenient Synthesis of Some 4-Substituted 5-Aminopyrimidines, J. Chem. Soc., 1953, pp. 3721-3722.

Landry et al., Pharmacologie Des Cibles Vers L'Indication Therapeutique, Cours et Exercices, 2003, p. 177.

Leguen, Pain management by a new series of dual inhibitors of enkephalin degrading enzymes: long lasting antinociceptive properties and potentiation by CCK2 antagonist or methadone, Pain, 2003, pp. 139-148, vol. 104.

Lensink, Synthesis and structure of sulfonamido cyclopentadiene titanium complexes: X-ray structure, Journal of Organometallic Chemistry 553, 1998, pp. 387-392.

Lin et al., Use of the Methylxanthine Derivative A802715 in Transplantation Immunology, I. Strong in Vitro Inhibitory Effects on CD28-Costimulated T Cell Activities, Transplantation, 1997, p. 1813, vol. 63.

Lin et al., Use of the Methylxanthine Derivative A802715 in Transplantation Immunology, I. Strong in Vitro Inhibitory Effects on CD28-Costimulated T Cell Activities, Transplantation, 1997, pp. 1734-1738, vol. 63.

Magnus et al., Neural Stem Cells in Inflammatory CNS Diseases: Mechanisms and Therapy, J. Cell. MoL Med., 2005, pp. 303-319, vol. 9.

Matter et al., Structural Requirements for Inhibition of the Neuronal Nitric Oxide Synthase (NOS-I): 3D-QSAR Analysis of 4-Oxo- and 4-Amino-Pteridine-Based Inhibitors, Med. Chem., 2002, pp. 2923-2941, vol. 45.

Merz, et al. Synthesis of 7-Benzylamino-6-chloro-2-piperazino-4-pyrrolidinopteridine and Novel Derivatives Free of Positional Isomers. Potent Inhibitors of cAMP-Specific Phosphodiesterase and of Malignant Tumor Cell Growth, J. Med. Chem., 1996, pp. 4733-4743, vol. 41.

Minett, Endogenous opioids contribute to insensitivity to pain in humans and mice lacking sodium channel Nav1.7, Nature Communciations, 2015, 8 pages.

Mohr, et al. Pteridines. Part XCVII. Synthesis and Properties of 6-thioxanthopterine and 7-thioisoxanthopterin, Helv. Chim. Acta, 1992, pp. 2317-2326, vol. 75.

Moody, et al., Toll-Like Receptor 7/8 (TLR7/8) and TLR9 Agonists Cooperate to Enhance HIV-1 Envelope Antibody Responses in Rhesus Macaques. Journal of Virology, Mar. 15, 2014, pp. 3329-3339, vol. 88, No. 6.

Moreb, et al., The Therapeutic Potential of Interleukin-1 and Tumor Necrosis Factor on Hematopoietic Stem Cells, Leuk, Lymphoma, 1992, pp. 267-275, vol. 8, Abstract Only.

Murata, et al. A Facile Method for Regioselective 6,7-Disubstitution of Pleridine, Heterocycles, 2000, pp. 1259-1262, vol. 53.

Neilsen, et al. Unequivocal Syntheses of 6-Methykl- and 6-Phenylisoxanthoterin, J. Heterocyclic Chem., 1987, pp. 1621-1628, vol. 24.

Nicolaus, Symbiotic Approach to Drug Design, in Decision Making in Drug Research, 1983, pp. 173-186, Gross (Ed.) Raven Press: New York.

Novis, et al., Reactivation of latent HIV-1 in central memory CD4+ T cells through TLR-1/2 stimulation, Retrovirology, 2013, 15 pages, vol. 10, No. 119.

Obach, Drug-drug Interactions: An Important Negative Attribute in Drugs, Drugs Today, 2003, pp. 301-338, vol. 39.

Ochoa et al., Application of Neural Networks to the Study of Structure-Activity Relationships of 6.7—Diarylpteridines as Nematocides, Med. Chem. Res., 1997, pp. 530-545, vol. 7.

Ohto, et al., Structure and Function of Toll-like Receptors, Microbes and Infection, Feb. 8, 2014, 1 page, vol. 16.

O'Neill, L. et al., The history of Toll-like receptors—redefining innate immunity, Nature Reviews/immunology, 2013, pp. 453-460, vol. 13.

Patani, et al., Bioisosterism: A Rational Approach in Drug Design, Chem. Rev., 1996, pp. 3147-3176, vol. 96.

Peng, et al., Toll-Like Receptor 8-Mediated Reversal of CD4+ Regulatory T Cell Function, Science, Aug. 26, 2005, pp. 1380-1384.

Pfleiderer et al., Pteridine, XII: Synthese von 2-Amino-4-Alkoxy-Pteridinen, Chem. Ber., 1961, pp. 12-18, vol. 94.

Ramu et al., Circumvention of Adriamycin Resistance by Dipyridamole Analogues: A Structure-activity Relationship Study, Int. J. Cancer, 1989, pp. 487-491, vol. 43.

Rodrigues et al., Co/SiO2 Catalysts for Selective Hydrogenation of Crotonaldehyde III. Promoting Effect of Zinc, Appl. Catalysis A: Gen., 2004, pp. 201-211, 257.

Roethle, et al., Identification and Optimization of Pteridinone Toll-Like Receptor 7 (TLR7) Agonists for the Oral Treatment of Viral Hepatitis, Journal of Medicinal Chemistry, 2013, pp. 7324-7333.

Rosowsky et al., Structure-activity and structure-selectivity studies on Diaminoquinozolines and other inhibitors of Pneumocystis carnii and Toxoplasma gondii Dihydrofolate Reductase, Antimicrobial Agents and Chemotherapy, 1995, pp. 78-86, vol. 39, No. 1.

Sasse, A simple new method for preparation of 2-substituted quinazolines, Sythesis., 1978, pp. 379-382.

Sato et al., Studies on Pyrazines. Part 37. Synthesis of 6-Propionylpteridine-2.4 (1H, 3H)-dione and its 1- and/or 3-Methyl Derivatives from Marine Natural Products, J. Chem. Soc., 2000, pp. 89-95, vol. 1.

Sielecki, et al., Quinazolines as cyclin dependent kinase inhibitors, Bioorg. Med. Chem. Lett., 2001, pp. 1157-1160, vol. 9.

Spickett et al., The Synthesis of Compounds With Potential Anti-Folic Acid Activity. Part I 7-Amino- and 7-Hydroxy-Pteridines, J. Chem. Soc., 1954, pp. 2887-2891.

Sugimoto et al., Regioselective Arylation of 1,3-Dimethyllumazine and Its 5-Oxide by Diazonium Salts, Pteridines, 1997, pp. 188-194, vol. 8.

Sun, Inhibitors of voltage-gated sodium channel Nav1.7: patent applications since 2010, Pharmaceutical Patent Analyst, 2014, pp. 509-521.

Taghavi-Moghadam et al., A New, General, and Regioselective Method for the Synthesis of 2, 6-Disubstituted 4-Aminopteridines, Tetrahedron Lett., 1997, pp. 6835-6836, vol. 38.

Taylor Jr., et al., Opioid antagonists for pain, Expert Opinion on Investigational Drugs, 2013, pp. 517-525.

Ulrich, Kirk-Othmer Encyclopedia of Chemical Technology, Wiley, Chapter 4: Crystallization, 2002 (7 pages).

Urakov et al., Multiple reactivity and tautomerism of substituted pyrimidines. IV. Multiple reactivity of 2-acetamido-4-quinazolinones, Uzbek J. Chem., 1995, pp. 37-41, Nos. 5-6 (1995).

Anynomous, Ankylosing Spondylitis, Retrieved Online on Jul. 27, 2007 from http://www.nlm.nih.gov/medicineplus/print/ankylosingspondylitis.html, 3 pages.

Anonymous, FDA mulls drug to slow late-stage Alzheimer's, Retrieved from CNN.com, Sep. 24, 2003, 2 pages Vema, et al. Design of EGFR Kinase Inhibitors: A Ligand-Based Approach and its Confirmation with Structure-Based Studies, Boorg. Med. Chem., 2003, pp. 4643-4653, vol. 11.

(56) References Cited

OTHER PUBLICATIONS

Vinot, Etude de Pteridiones-2,4 III Orientation de la Reaction de Condensation D'a-dicetones Avec le Diamino-4,5 Dimethyl-1,3 Uracile, Bulletin de la Societe Chimique de France, 1972, pp. 2752-5722, No. 9-10.

Vippagunta, et al. Crystalline Solids, Adv. Drug Del. Rev., 2001, pp. 3-26, vol. 48.

Wang et al., Organic Letters, 2004, pp. 2793-2796, vol. 6.

Warren, Therapeutic efficacy of the small molecule GS-5734 against Ebola virus in rhesus monkeys, Nature, 2016, 19 pages.

Watashi, et al., Interleukin-1 and Tumor Necrosis Factor Triggeer Restriction of Hepatitis B Virus Infection Via a Cytidine Deaminase Activation-induced Cytidine Deaminase (AID), The Journal of Biological Chemistry, Nov. 1, 2013, pp. 31715-31727, vol. 288, No. 44.

Weinstock, et al. Pteridines. XII. Structure-Activity Relationships of Some Pteridine Diuretics, J. Med. Chem., 1968, pp. 573-579, vol. 11.

West, Solid State Chemistry and its Applications, Wiley, pp. 358, 365, 1988.

Willie-Reece, et al., Toll-like receptor agonists influence the magnitude and quality of memory T cell responses after prime-boost immunization in nonhuman primates, The Journal of Experimental Medicine, May 15, 2006, pp. 1249-1258.

Wolff (ed.) Burger's Medicinal Chemistry and Drug Discovery: Fifth Edition, Principles and Practice, 1995, pp. 783-802, vol. 1.

Wolff (ed.) Burger's Medicinal Chemistry and Drug Discovery: Fifth Edition, Principles and Practice, 1995, pp. 975-977, vol. 1.

Xagorari, Toll-Like Receptors and Viruses: Induction of Innate Antiviral Immune Responses, The Open Microbiology Journal, 2008, pp. 49-59, vol. 2.

Yao, et al. Pteridines. Protection of Pteridines, Helv. Chim. Acta., 2003, pp. 1-12, vol. 86.

Yin, P. et al., Synthesis of 2,4-Diaminoquinazolines and Tricyclis Quinazolines by Cascade Reductive Cyclization of Methyl N-Cyano-2-notrobenzimidates, The Journal of Organic Chemistry, 2012, pp. 2649-2658, vol. 77.

Ypakob, et al., Taytomepnr, 1994, pp. 37-41.

Yu, et al., Dual Character of Toll-like Receptor Signaling: Protumorigenic Effects and Anti-tumor Functions, Biochimica et Biophysica Acta, 2013, 1 page, Abstract only.

Zhao, et al., Toll-like Receptors and Prostate Cancer, Frontiers in Immunology, Jul. 23, 2014, 1 page, vol. 5.

FIG. 1. XRPD pattern of Compound I Form I
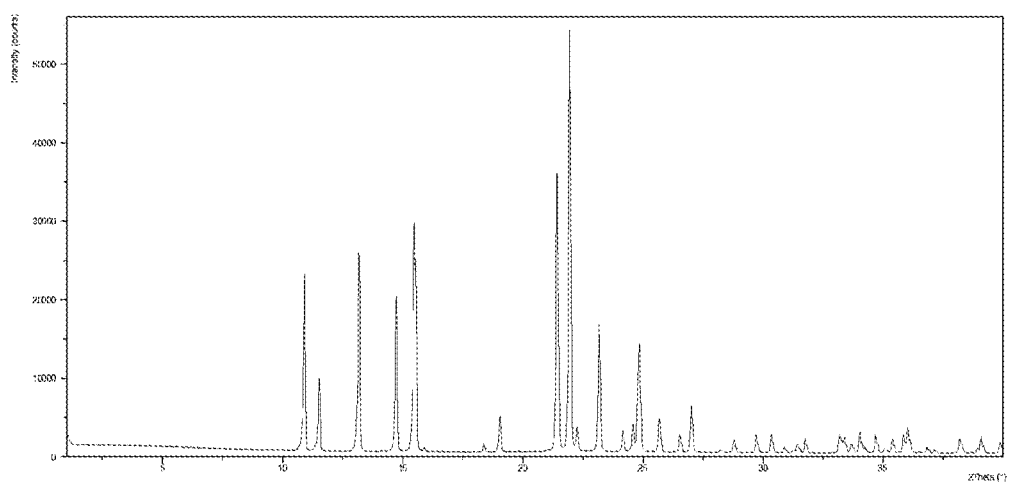

FIG. 2. XRPD pattern of Compound I Gentisic Acid
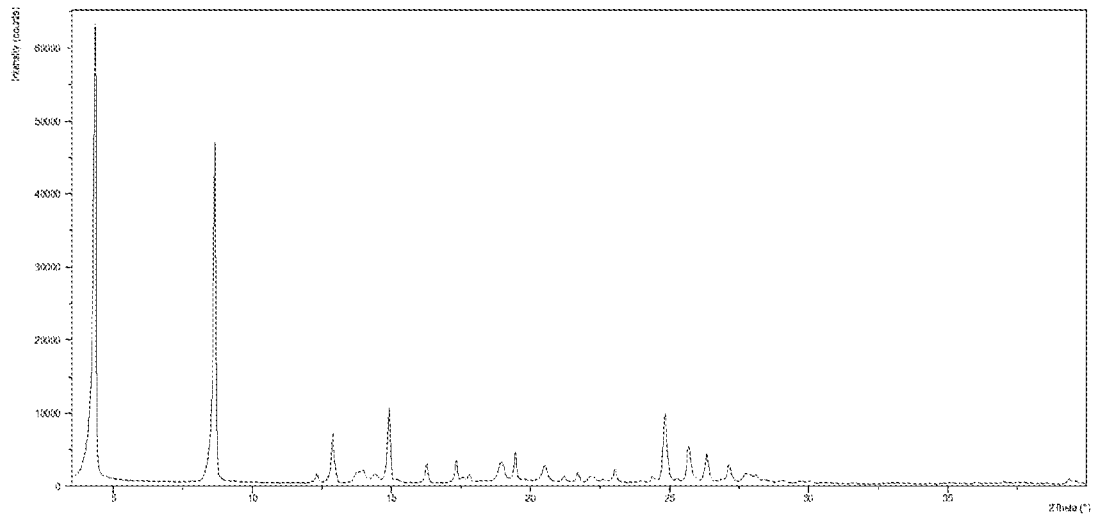
FIG. 3. DSC of Compound I Gentisic Acid
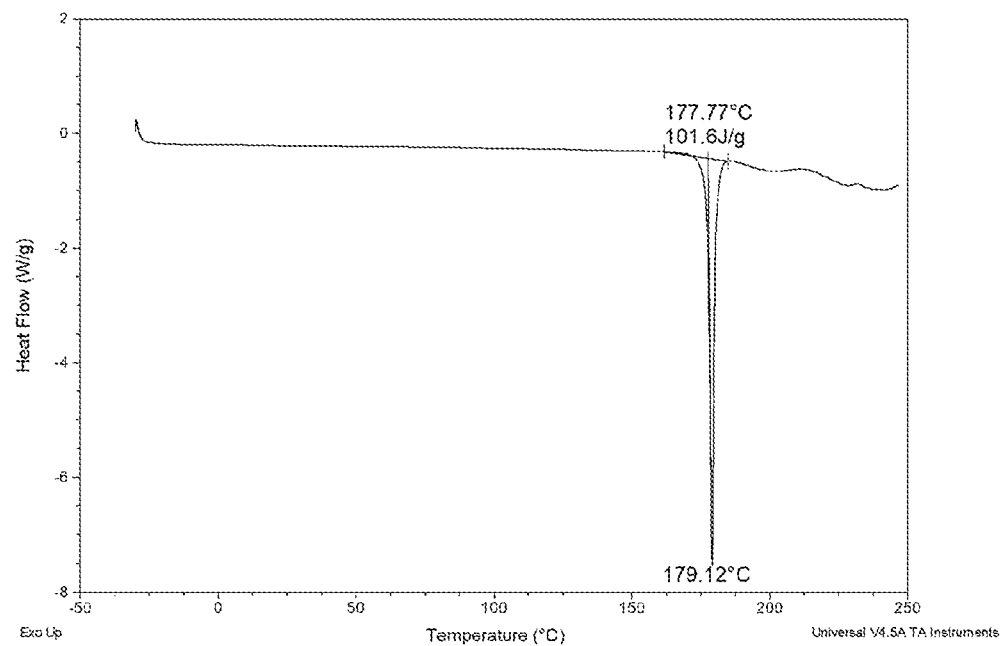

FIG. 4. TGA of Compound I Gentisic Acid
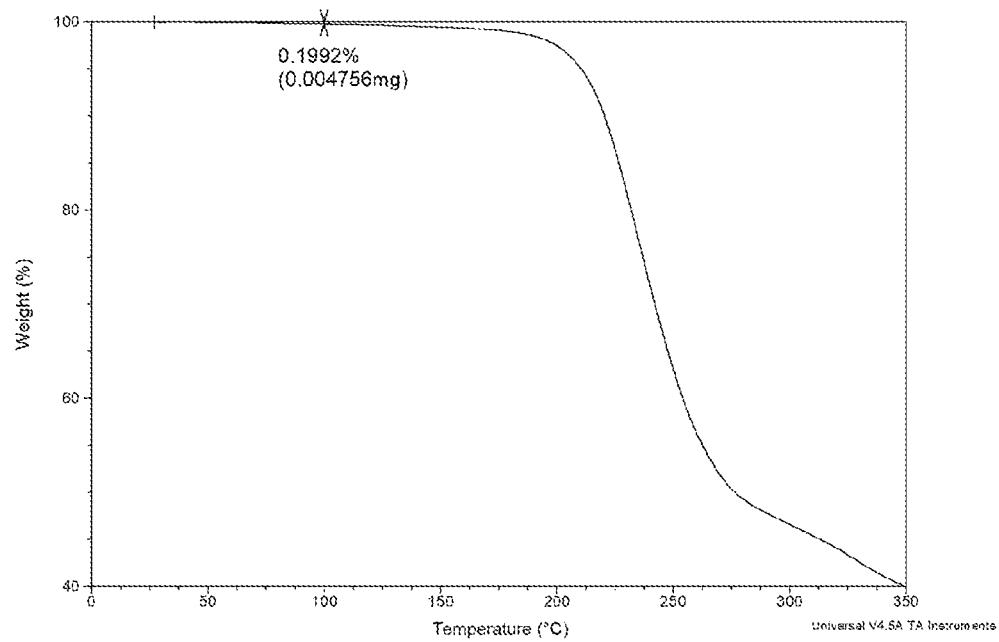
FIG. 5. DVS of Compound I Gentisic Acid
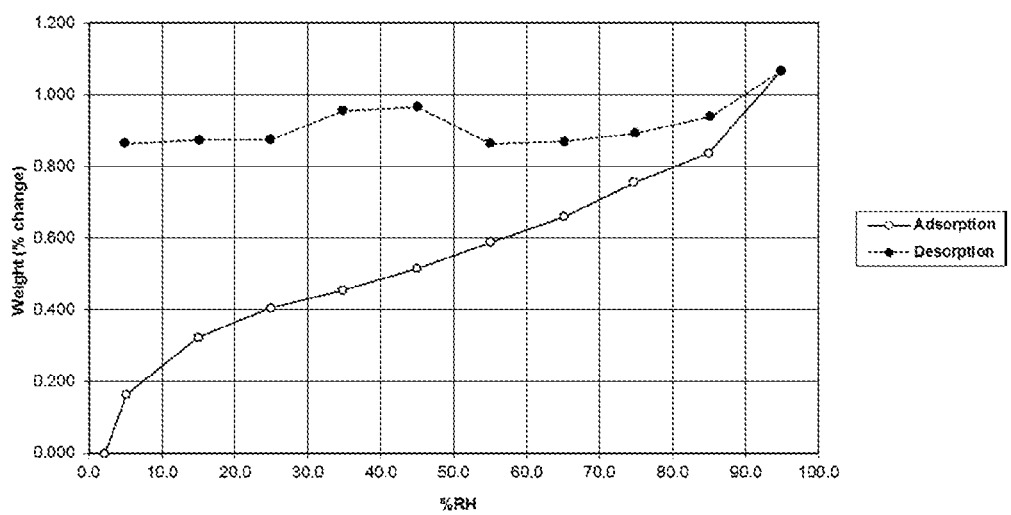

FIG. 6. XRPD pattern of Compound I Hippuric Acid
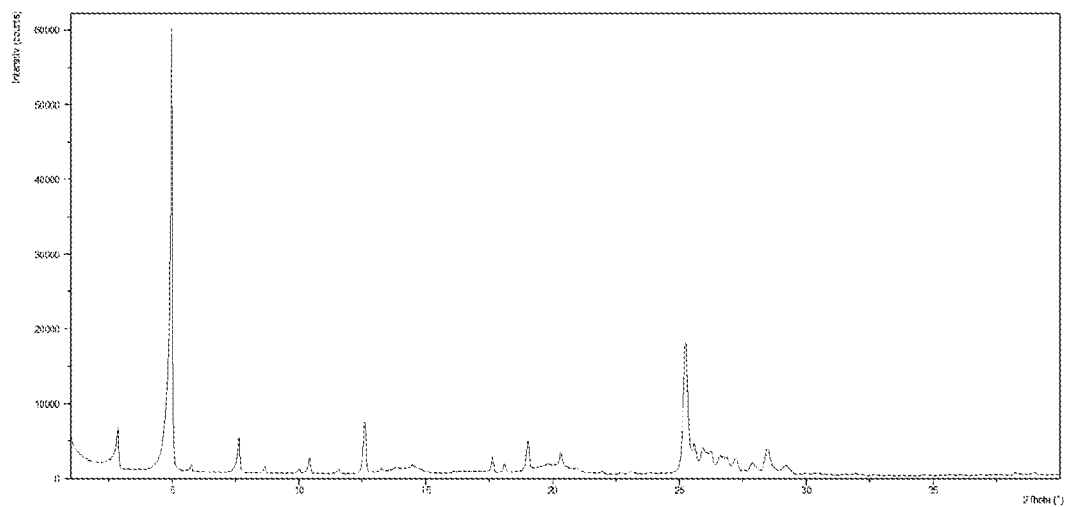
FIG. 7. DSC of Compound I Hippuric Acid
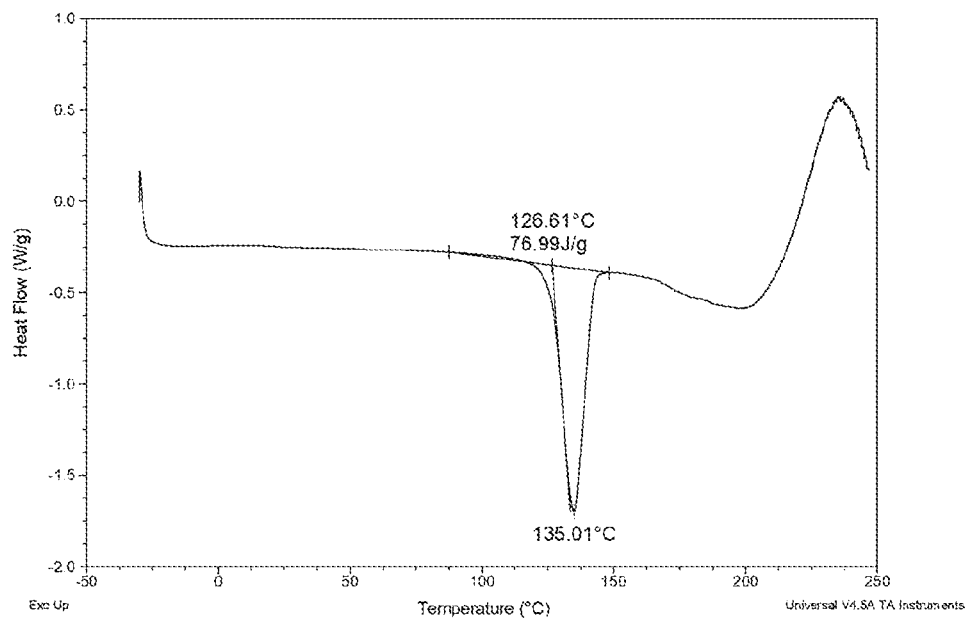

FIG. 8. TGA of Compound I Hippuric Acid
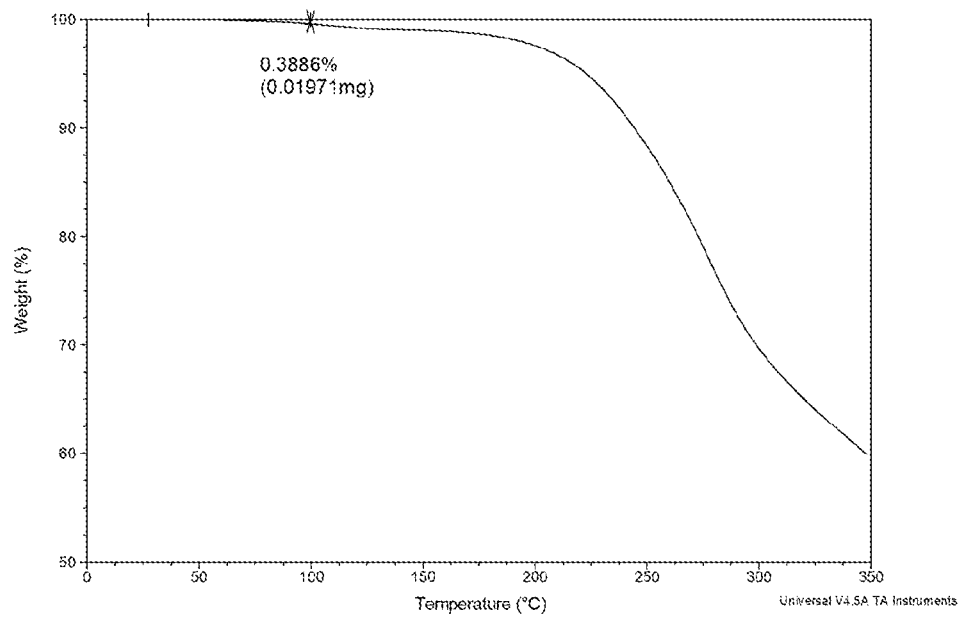
FIG. 9. DVS of Compound I Hippuric Acid
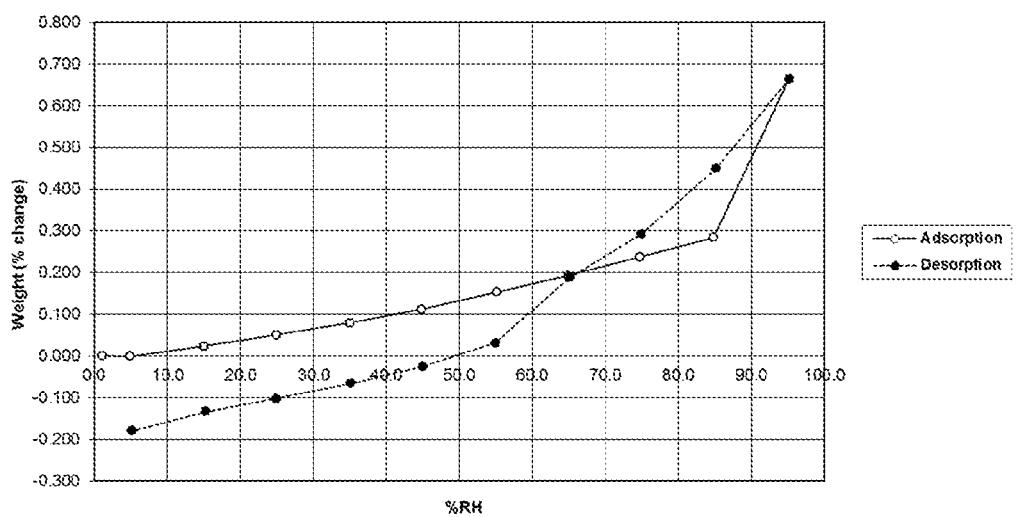

FIG. 10. XRPD pattern of Compound I Phosphoric Acid Form I
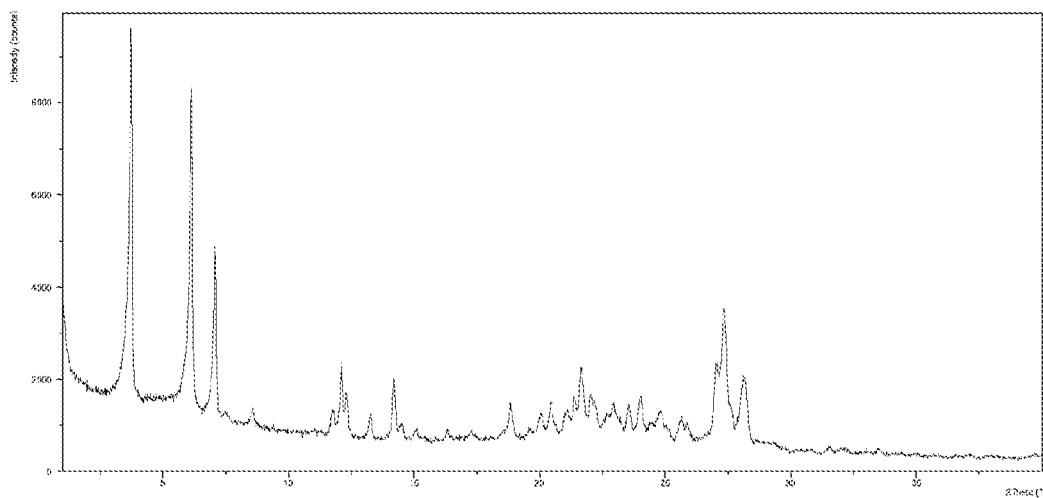
FIG. 11. DSC of Compound I Phosphoric Acid Form I
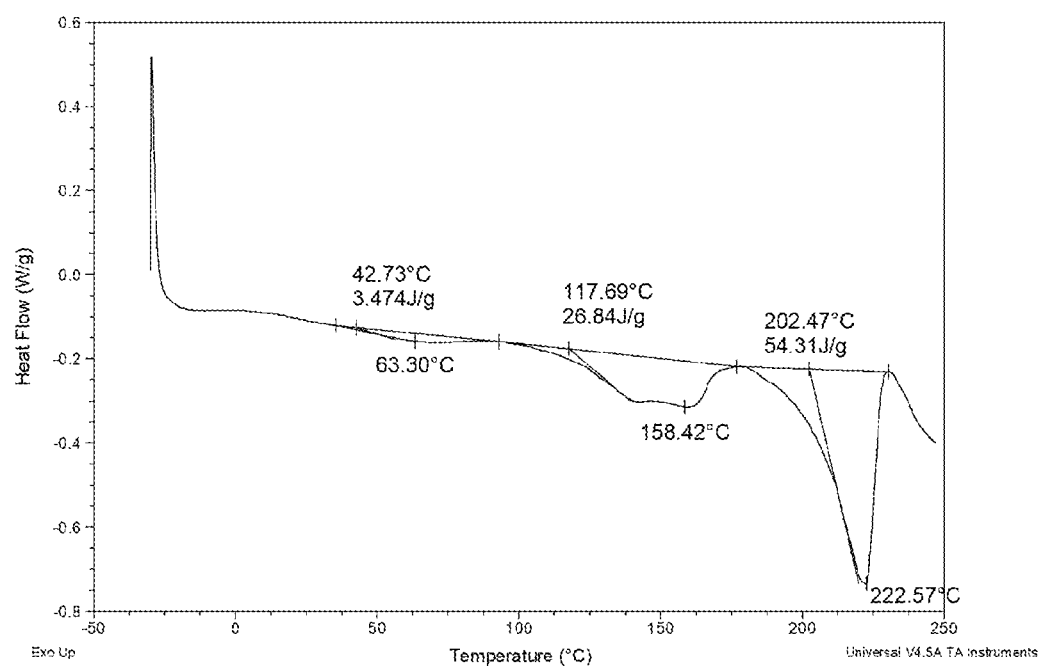

FIG. 12. TGA of Compound I Phosphoric Acid Form I
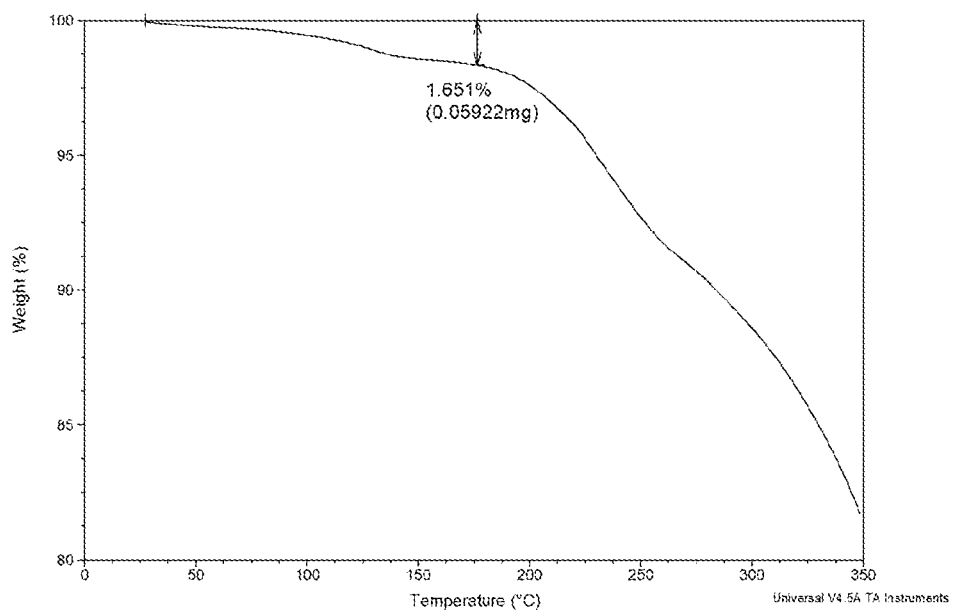

FIG. 13. XRPD pattern of Compound I Phosphoric Acid Form II
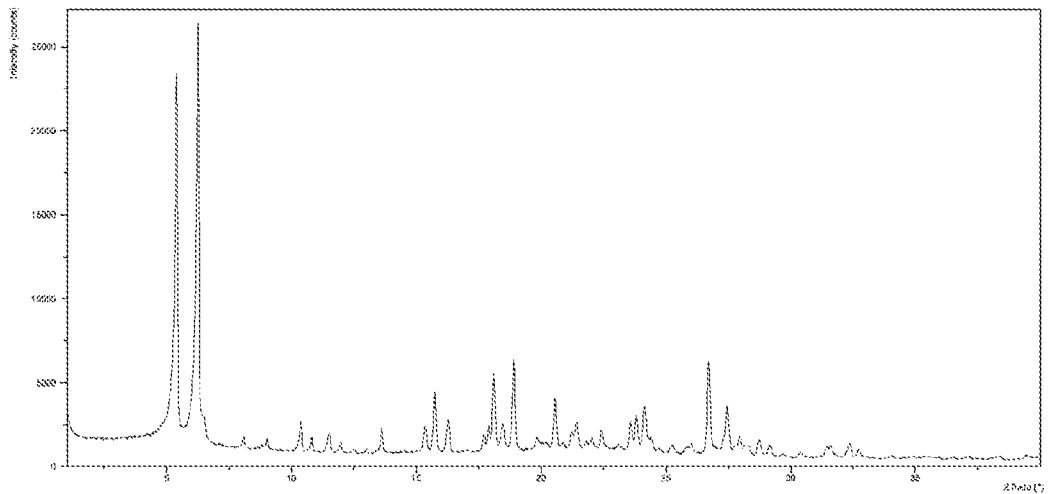
FIG. 14. DSC of Compound I Phosphoric Acid Form II
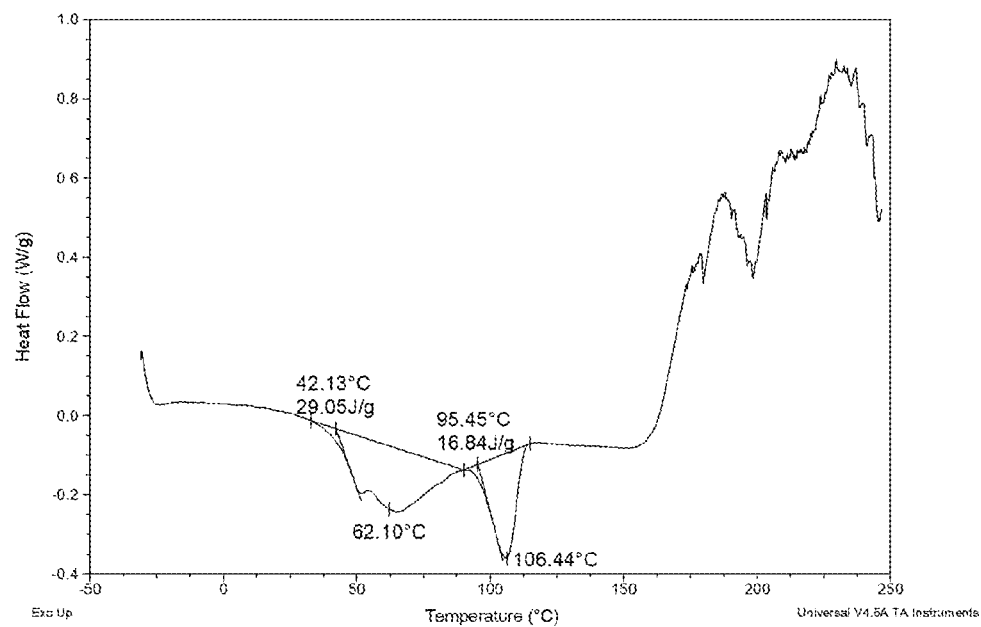

FIG. 15. TGA of Compound I Phosphoric Acid Form II
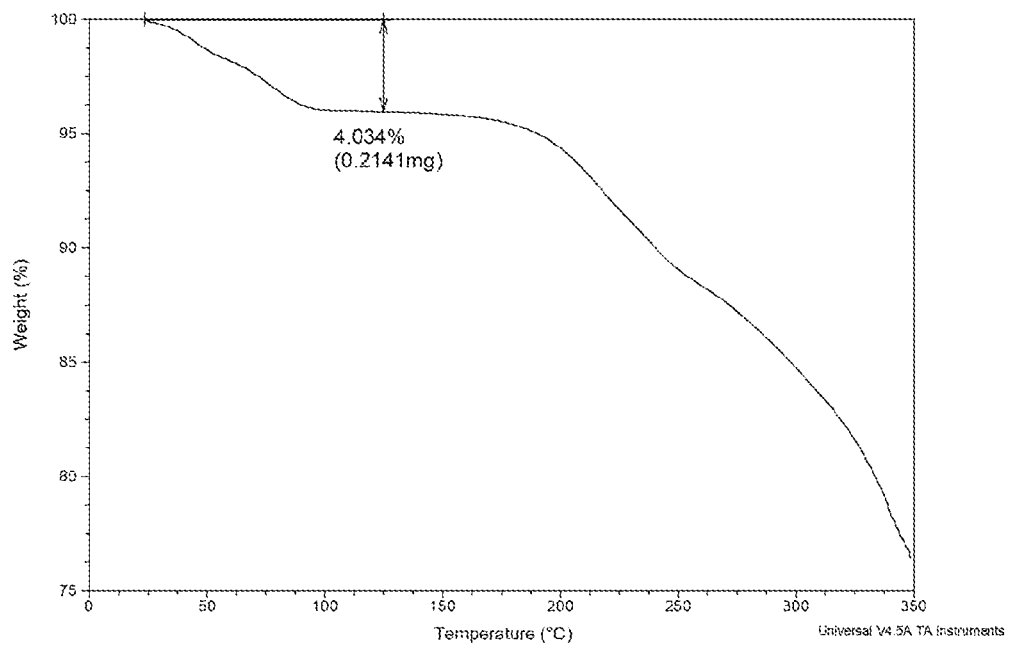

FIG. 16. XRPD pattern of Compound I Succinic Acid
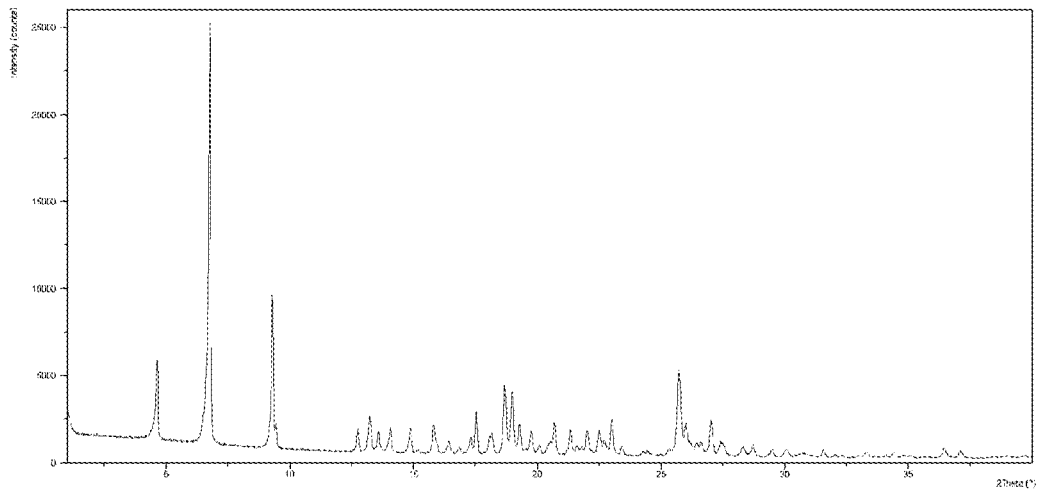
FIG. 17. DSC of Compound I Succinic Acid
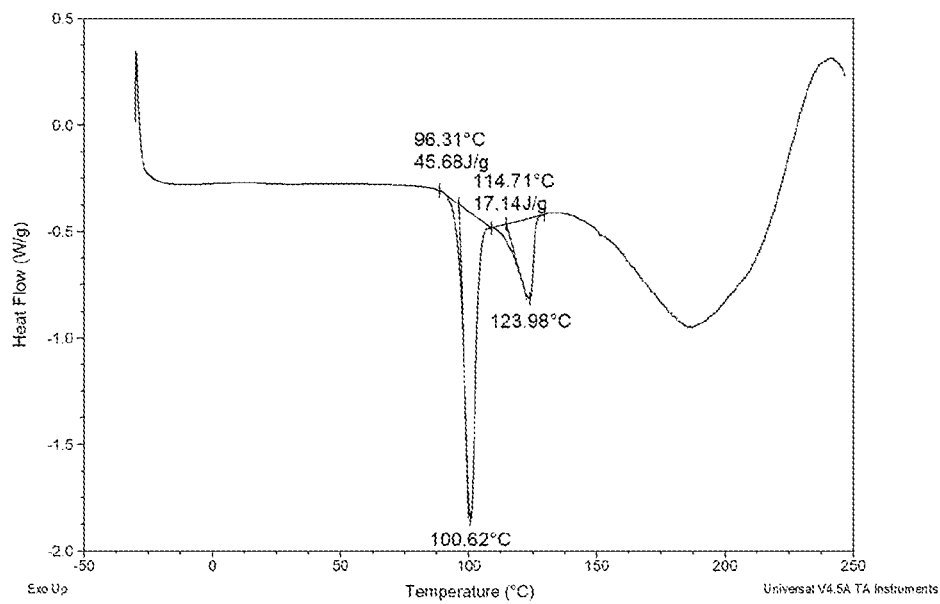

FIG. 18. TGA of Compound I Succinic Acid
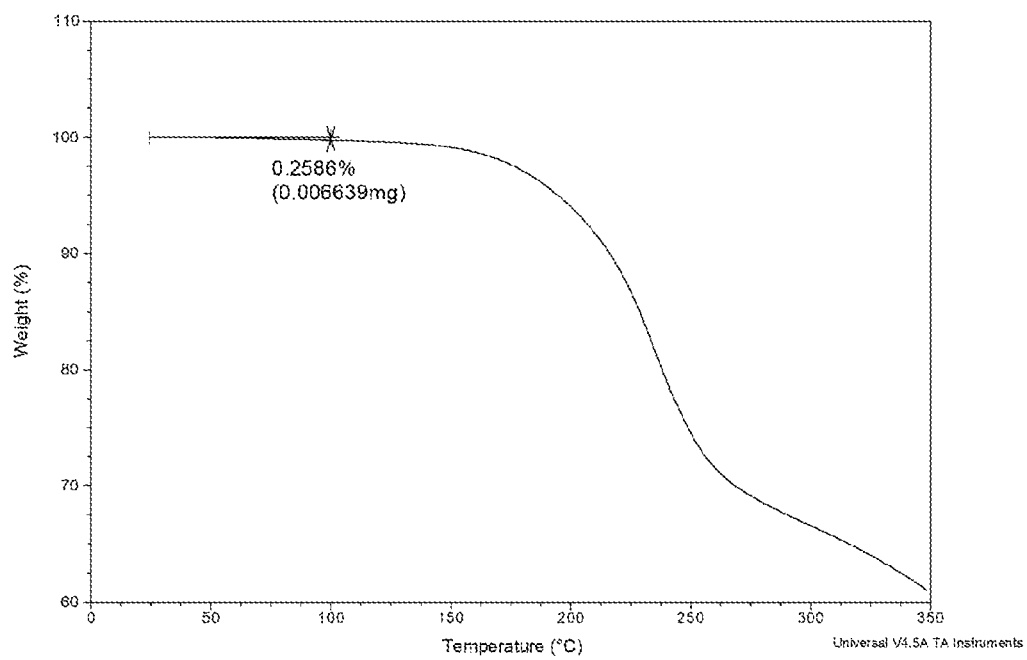
FIG. 19. DVS of Compound I Succinic Acid
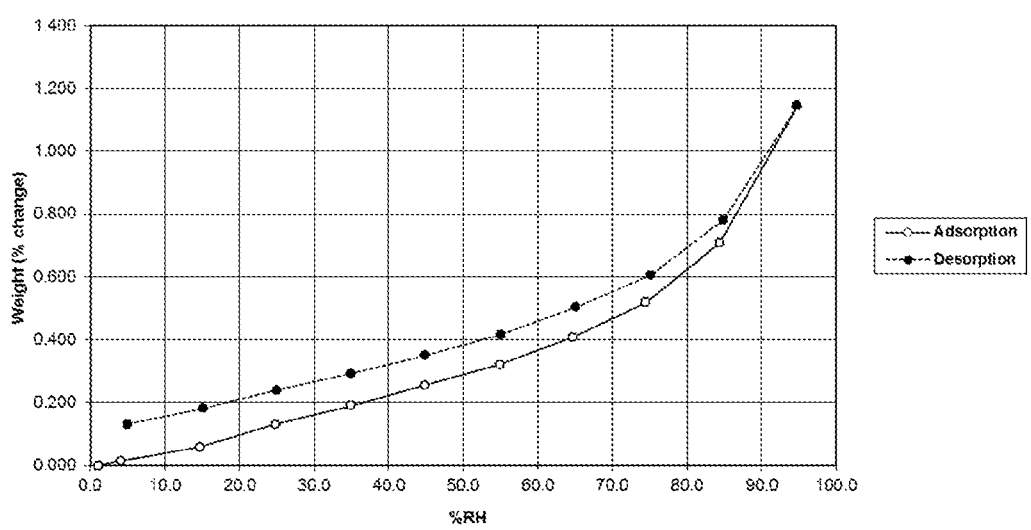

FIG. 20. XRPD pattern of Compound I Ethanedisulfonic Acid Form I
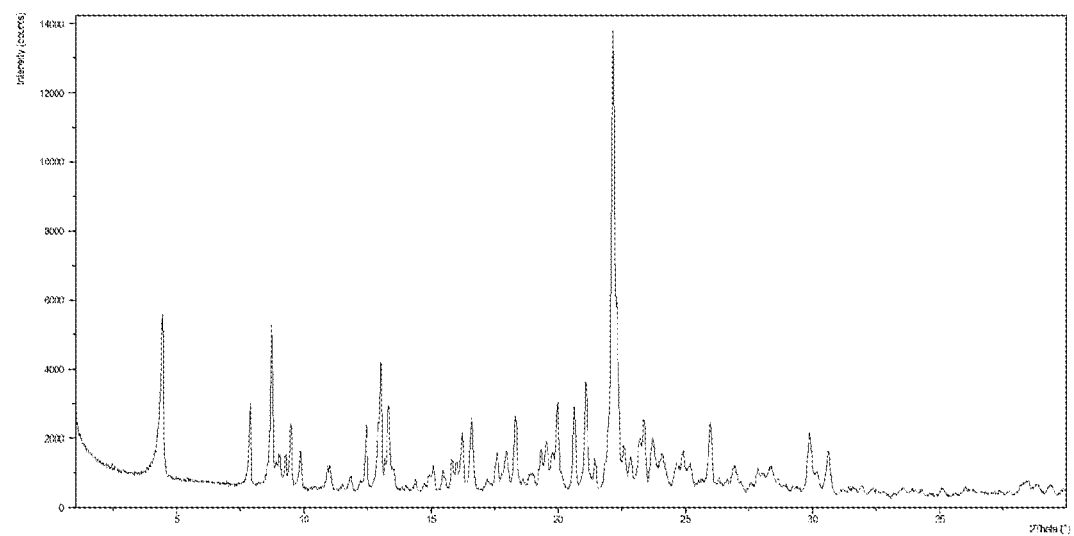
FIG. 21. XRPD pattern of Compound I Ethanedisulfonic Acid Form II
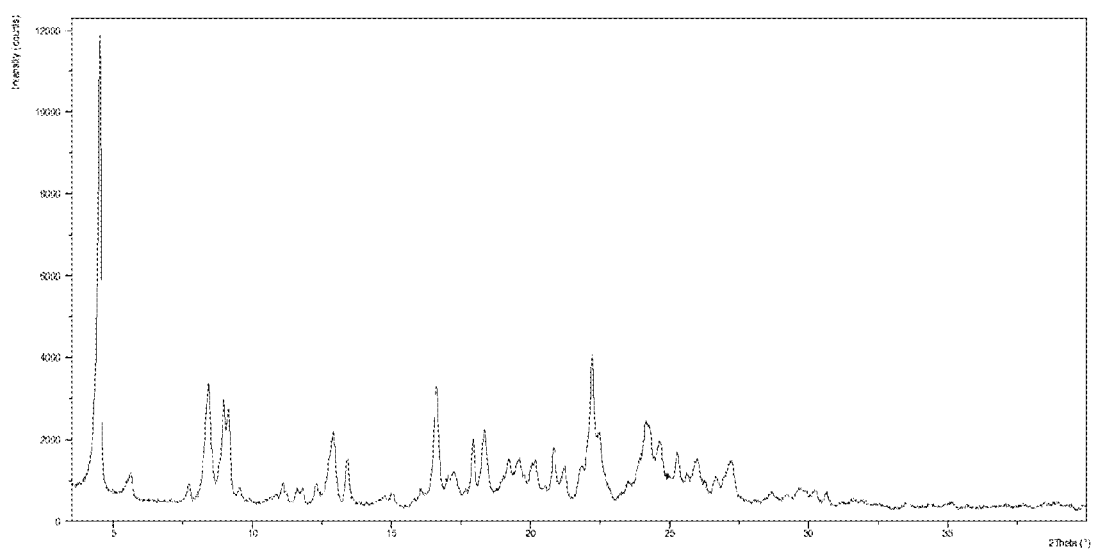

SOLID FORMS OF A TOLL-LIKE RECEPTOR MODULATOR

CROSS-REFERENCES TO RELATED APPLICATIONS

This application claims the benefit of U.S. Provisional Application No. 62/835,359, filed on Apr. 17, 2019, the entire content of which is hereby incorporated by reference in its entirety.

FIELD

This application relates generally to toll-like receptor modulator compounds, including diamino pyrido[3,2 D] pyrimidine compounds, and pharmaceutical compositions which, among other things, modulate toll-like receptors (e.g. TLR-8), and methods of making and using them.

BACKGROUND

The toll-like receptor (TLR) family plays a fundamental role in pathogen recognition and activation of innate immunity. Toll-like receptor 8 (TLR-8) is predominantly expressed by myeloid immune cells and activation of this receptor stimulates a broad immunological response. Agonists of TLR-8 activate myeloid dendritic cells, monocytes, monocyte-derived dendritic cells and Kupffer cells leading to the production of proinflammatory cytokines and chemokines, such as interleukin-18 (IL-18), interleukin-12 (IL-12), tumor necrosis factor-alpha (TNF-α), and interferon-gamma (IFN-γ). Such agonists also promote the increased expression of co-stimulatory molecules such as $CD8^+$ cells, major histocompatibility complex molecules (MAIT, NK cells), and chemokine receptors.

Collectively, activation of these innate and adaptive immune responses induces an immune response and provides a therapeutic benefit in various conditions involving autoimmunity, inflammation, allergy, asthma, graft rejection, graft versus host disease (GvHD), infection, cancer, and immunodeficiency. For example, with respect to hepatitis B, activation of TLR8 on professional antigen presenting cells (pAPCs) and other intrahepatic immune cells is associated with induction of IL-12 and proinflammatory cytokines, which is expected to augment HBV-specific T cell responses, activate intrahepatic NK cells and drive reconstitution of antiviral immunity. See e.g. Wille-Reece, U. et al. *J Exp Med* 203, 1249-1258 (2006); Peng, G. et al., *Science* 309, 1380-1384 (2005); Jo, J. et al., *PLoS Pathogens* 10, e1004210 (2014) and Watashi, K. et al., *J Biol Chem* 288, 31715-31727 (2013).

Given the potential to treat a wide array of diseases, there remains a need for novel modulators of toll-like receptors, for example TLR-8. Potent and selective modulators of TLR-8 that have reduced potential for off target liabilities are particularly desirable.

BRIEF SUMMARY OF THE DISCLOSURE

In one embodiment, the present disclosure provides a crystalline form of (R)-2-((2-amino-7-fluoropyrido[3,2-d]pyrimidin-4-yl)amino)-2-methylhexan-1-ol gentisic acid:

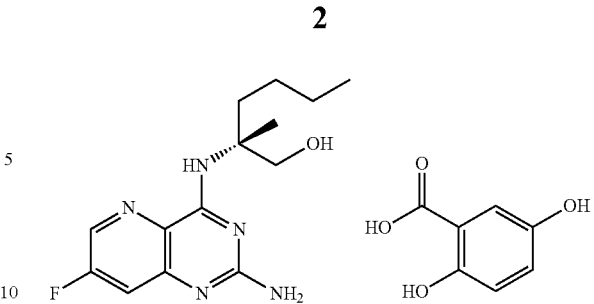

characterized by an X-ray powder diffraction (XRPD) pattern comprising three or more peaks at 4.4°, 8.7°, 12.9°, 14.9°, 17.3°, 19.5°, 24.8°, 25.7°, or 26.3° 2θ (±0.2° 2θ), Compound I gentisic acid.

In another embodiment, the present disclosure provides a crystalline form of (R)-2-((2-amino-7-fluoropyrido[3,2-d]pyrimidin-4-yl)amino)-2-methylhexan-1-ol hippuric acid:

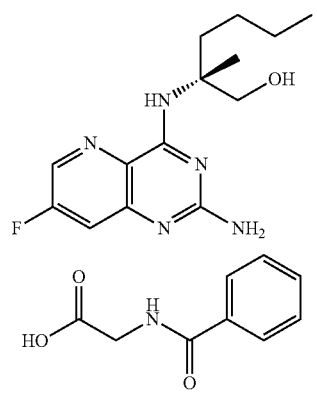

characterized by an XRPD pattern comprising three or more peaks at 2.9°, 5.0°, 7.6°, 10.4°, 12.6°, 17.6°, 19.0°, 25.2°, or 28.5° 2θ (±0.2° 2θ), Compound I hippuric acid.

In another embodiment, the present disclosure provides a crystalline form of (R)-2-((2-amino-7-fluoropyrido[3,2-d]pyrimidin-4-yl)amino)-2-methylhexan-1-ol phosphoric acid:

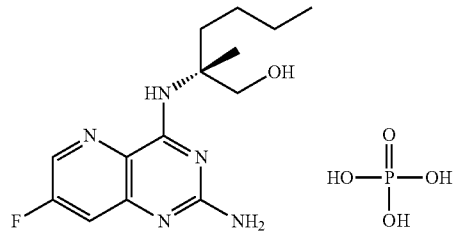

characterized by an XRPD pattern comprising three or more peaks at 3.7°, 6.1°, 7.1°, 12.1°, 14.2°, 21.6°, 24.0°, 27.4°, or 28.2° 2θ (±0.2° 2θ), phosphate salt Form I.

In another embodiment, the present disclosure provides a crystalline form of (R)-2-((2-amino-7-fluoropyrido[3,2-d]pyrimidin-4-yl)amino)-2-methylhexan-1-ol phosphoric acid:

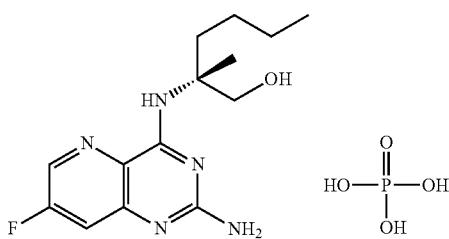

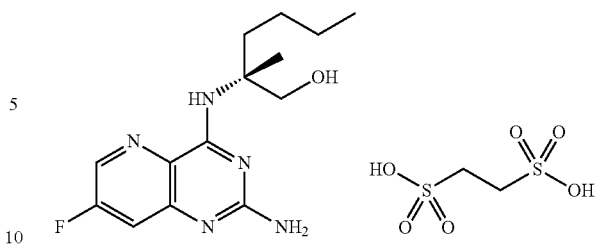

characterized by an XRPD pattern comprising three or more peaks at 5.4°, 6.3°, 15.8°, 18.1°, 18.9°, 20.6°, 24.1°, 26.7°, or 27.4° 2θ (±0.2° 2θ), phosphate salt Form II.

In another embodiment, the present disclosure provides a crystalline form of (R)-2-((2-amino-7-fluoropyrido[3,2-d]pyrimidin-4-yl)amino)-2-methylhexan-1-ol succinic acid:

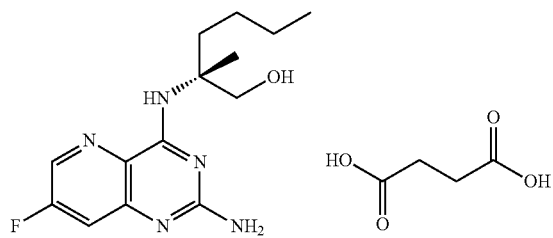

characterized by an XRPD pattern comprising three or more peaks at 4.6°, 6.8°, 9.3°, 13.2°, 17.5°, 18.7°, 19.0°, 25.7°, or 27.0° 2θ (±0.2° 2θ), Compound I succinic acid.

In another embodiment, the present disclosure provides a crystalline form of (R)-2-((2-amino-7-fluoropyrido[3,2-d]pyrimidin-4-yl)amino)-2-methylhexan-1-ol ethanedisulfonic acid:

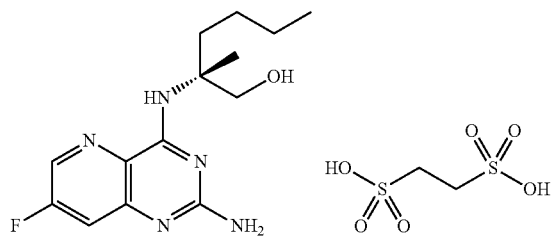

characterized by an XRPD pattern comprising three or more peaks at 4.4° 7.9° 8.7°, 13.0°, 16.6°, 20.6°, 21.1°, 22.1°, or 26.0° 2θ (±0.2° 2θ), Compound I ethanedisulfonic acid Form I.

In another embodiment, the present disclosure provides a crystalline form of (R)-2-((2-amino-7-fluoropyrido[3,2-d]pyrimidin-4-yl)amino)-2-methylhexan-1-ol ethanedisulfonic acid:

characterized by an XRPD pattern comprising three or more peaks at 4.5°, 5.6°, 8.4°, 12.9°, 13.4°, 16.6°, 17.9°, 18.3°, or 22.2° 2θ (±0.2° 2θ), Compound I ethanedisulfonic acid Form II.

BRIEF DESCRIPTION OF THE DRAWINGS

FIG. 1. shows the XRPD pattern for Compound I Form I.
FIG. 2 shows the XRPD pattern for Compound I gentisic acid.
FIG. 3 shows the DSC thermograph for Compound I gentisic acid.
FIG. 4 shows the TGA curve for Compound I gentisic acid.
FIG. 5 shows the DVS curve for Compound I gentisic acid.
FIG. 6 shows the XRPD pattern for Compound I hippuric acid.
FIG. 7 shows the DSC thermograph for Compound I hippuric acid.
FIG. 8 shows the TGA curve for Compound I hippuric acid.
FIG. 9 shows the DVS curve for Compound I hippuric acid.
FIG. 10 shows the XRPD pattern for Compound I phosphoric acid Form I.
FIG. 11 shows the DSC thermograph for Compound I phosphoric acid Form I.
FIG. 12 shows the TGA curve for Compound I phosphoric acid Form I.
FIG. 13 shows the XRPD pattern for Compound phosphoric acid Form II.
FIG. 14 shows the DSC thermograph for Compound I phosphoric acid Form II.
FIG. 15 shows the TGA curve for Compound I phosphoric acid Form II.
FIG. 16 shows the XRPD pattern for Compound I succinic acid.
FIG. 17 shows the DSC thermograph for Compound I succinic acid.
FIG. 18 shows the TGA curve for Compound I succinic acid.
FIG. 19 shows the DVS curve for Compound I succinic acid.
FIG. 20 shows the XRPD pattern for Compound I ethanedisulfonic acid Form I.
FIG. 21 shows the XRPD pattern for Compound I ethanedisulfonic acid Form II.

DETAILED DESCRIPTION OF THE DISCLOSURE

I. General

The present disclosure results from the surprising discoveries of the solid forms of (R)-2-((2-amino-7-fluoropyrido[3,2-d]pyrimidin-4-yl)amino)-2-methylhexan-1-ol (Compound I):

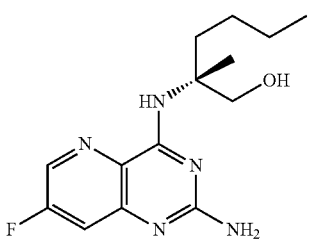

and salts, solvates or co-crystals thereof. Compound I can adopt a variety of crystalline forms, including, but not limited to, crystalline Compound I gentisic acid, crystalline Compound I hippuric acid, crystalline Compound I phosphoric acid Form I, crystalline Compound I phosphoric acid Form II, crystalline Compound I succinic acid, crystalline Compound I ethanedisulfonic acid Form I, and crystalline Compound I ethanedisulfonic acid Form II. Compound I can form a mixture of two or more crystalline forms, or form a single crystalline form substantially free of other crystalline forms.

The X-ray powder diffraction (XRPD) patterns provided herein of the solid forms of (R)-2-((2-amino-7-fluoropyrido[3,2-d]pyrimidin-4-yl)amino)-2-methylhexan-1-ol (Compound I) were collected using Cu Kα radiation.

II. Definitions

As used in the present specification, the following words and phrases are generally intended to have the meanings as set forth below, except to the extent that the context in which they are used indicates otherwise.

"Hydrate" refers to a complex formed by the combining of Compound I and water. The term includes stoichiometric as well as non-stoichiometric hydrates.

"Solvate" refers to a complex formed by the combining of Compound I and a solvent.

"Desolvated" refers to a Compound I form that is a solvate as described herein, and from which solvent molecules have been partially or completely removed. Desolvation techniques to produce desolvated forms include, without limitation, exposure of a Compound I Form (solvate) to vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially solvated wherein solvent molecules are present in stoichiometric or non-stoichiometric amounts.

"Alcohol" refers to a solvent having a hydroxy group. Representative alcohols can have any suitable number of carbon atoms, such as $C_1$-$C_6$, and any suitable number of hydroxy groups, such as 1-3. Exemplary alcohols include, but are not limited to, methanol, ethanol, n-propanol, i-propanol, etc.

"Therapeutically effective amount" refers to an amount that is sufficient to effect treatment, as defined below, when administered to a mammal in need of such treatment. The therapeutically effective amount will vary depending upon the subject being treated, the weight and age of the subject, the severity of the disease condition, the manner of administration and the like, which can readily be determined by one of ordinary skill in the art.

"Substantially free of other crystalline forms of Compound I" refers to a crystalline form of Compound I that contains less than 10% of other crystalline forms of Compound I. For example, substantially free can refer to a crystalline form of Compound I that contains less than 9, 8, 7, 6, 5, 4, 3, 2, or 1% of other crystalline forms of Compound I. Preferably, substantially free refers to a crystalline form of Compound I that contains less than 5% of other crystalline forms of Compound I. Preferably, substantially free refers to a crystalline form of Compound I that contains less than 1% of other crystalline forms of Compound I.

III. Solid Forms of Compound I

The present disclosure provides solid forms of (R)-2-((2-amino-7-fluoropyrido[3,2-d]pyrimidin-4-yl)amino)-2-methylhexan-1-ol (Compound I; see U.S. Pat. No. 9,670,205), including crystalline forms, as well as salts, solvates or co-crystal forms. In some embodiments, the present disclosure provides a crystalline form of Compound I having the structure:

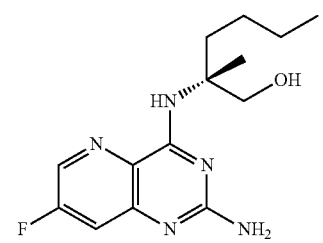

and salts, solvates or co-crystals thereof.

Compound I can adopt a variety of crystalline forms, including, but not limited to, crystalline Compound I gentisic acid, crystalline Compound I hippuric acid, crystalline Compound I phosphoric acid Form I, crystalline Compound I phosphoric acid Form II, crystalline Compound I succinic acid, crystalline Compound I ethanedisulfonic acid Form I, and crystalline Compound I ethanedisulfonic acid Form II. Compound I can form a mixture of two or more crystalline forms, or form a single crystalline form substantially free of other crystalline forms.

In some embodiments, the present disclosure provides a compound selected from the group consisting of: (R)-2-((2-amino-7-fluoropyrido[3,2-d]pyrimidin-4-yl)amino)-2-methylhexan-1-ol gentisic acid; (R)-2-((2-amino-7-fluoropyrido[3,2-d]pyrimidin-4-yl)amino)-2-methylhexan-1-ol hippuric acid; (R)-2-((2-amino-7-fluoropyrido[3,2-d]pyrimidin-4-yl)amino)-2-methylhexan-1-ol phosphoric acid Form I; (R)-2-((2-amino-7-fluoropyrido[3,2-d]pyrimidin-4-yl)amino)-2-methylhexan-1-ol phosphoric acid Form II; (R)-2-((2-amino-7-fluoropyrido[3,2-d]pyrimidin-4-yl)amino)-2-methylhexan-1-ol succinic acid; (R)-2-((2-amino-7-fluoropyrido[3,2-d]pyrimidin-4-yl)amino)-2-methylhexan-1-ol ethanedisulfonic acid Form I; and (R)-2-((2-amino-7-fluoropyrido[3,2-d]pyrimidin-4-yl)amino)-2-methylhexan-1-ol ethanedisulfonic acid Form II.

Form I

In some embodiments, the present disclosure provides a crystalline form of (R)-2-((2-amino-7-fluoropyrido[3,2-d]pyrimidin-4-yl)amino)-2-methylhexan-1-ol, wherein the crystalline form is Form I. In some embodiments, the present disclosure provides a crystalline form of (R)-2-((2-amino-7-fluoropyrido[3,2-d]pyrimidin-4-yl)amino)-2-methylhexan-1-ol (Compound I):

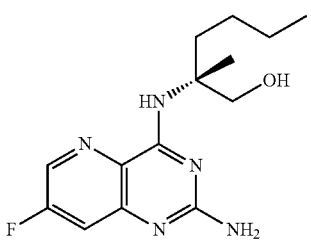

characterized by an X-ray powder diffraction (XRPD) pattern comprising
peaks at 10.9°, 11.5°, 13.2°, 14.7°, 15.5°, 21.4°, 21.9°, 23.2°, and 24.9° 2θ (±0.2° 2θ). In some embodiments, Form I is characterized by a unit cell as determined by single crystal X-ray crystallography of the following dimensions: a=8.0344 (2) Å; b=8.0344 (2) Å; c=23.7871 (7) Å; α=90°; β=90°; and γ=90°. In some embodiments, Form I is characterized by an XRPD pattern substantially as shown in FIG. 1.

Gentisic Acid

In some embodiments, the present disclosure provides a crystalline form of (R)-2-((2-amino-7-fluoropyrido[3,2-d]pyrimidin-4-yl)amino)-2-methylhexan-1-ol gentisate, wherein the crystalline form is the Gentisate Salt. In some embodiments, the present disclosure provides a crystalline form of (R)-2-((2-amino-7-fluoropyrido[3,2-d]pyrimidin-4-yl)amino)-2-methylhexan-1-ol, wherein the crystalline form is the Compound I Gentisic Acid co-crystal. In some embodiments, the present disclosure provides a crystalline form of (R)-2-((2-amino-7-fluoropyrido[3,2-d]pyrimidin-4-yl)amino)-2-methylhexan-1-ol gentisic acid:

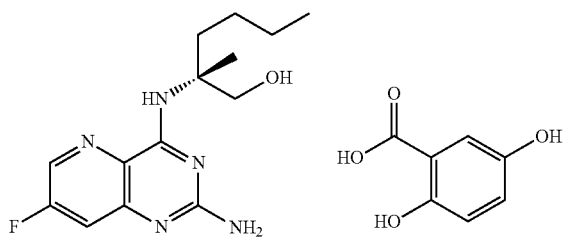

characterized by an X-ray powder diffraction (XRPD) pattern comprising three or more peaks at 4.4°, 8.7°, 12.9°, 14.9°, 17.3°, 19.5°, 24.8°, 25.7°, or 26.3° 2θ (±0.2° 2θ), Compound I gentisic acid.

In some embodiments, the Compound I gentisic acid is characterized by an XRPD pattern comprising four or more peaks at 4.4°, 8.7°, 12.9°, 14.9°, 17.3°, 19.5°, 24.8°, 25.7°, or 26.3° 2θ (±0.2° 2θ). In some embodiments, Compound I gentisic acid is characterized by an XRPD pattern comprising five or more peaks at 4.4°, 8.7°, 12.9°, 14.9°, 17.3°, 19.5°, 24.8°, 25.7°, or 26.3° 2θ (±0.2° 2θ). In some embodiments, the Compound I gentisic acid is characterized by an XRPD pattern comprising six or more peaks at 4.4°, 8.7°, 12.9°, 14.9°, 17.3°, 19.5°, 24.8°, 25.7°, or 26.3° 2θ (±0.2° 2θ). In some embodiments, the Compound I gentisic acid is characterized by an XRPD pattern comprising seven or more peaks at 4.4° 8.7°, 12.9°, 14.9°, 17.3°, 19.5°, 24.8°, 25.7°, or 26.3° 2θ (±0.2° 2θ). In some embodiments, the Compound I gentisic acid is characterized by an XRPD pattern comprising eight or more peaks at 4.4°, 8.7°, 12.9°, 14.9°, 17.3°, 19.5°, 24.8°, 25.7°, or 26.3° 2θ (±0.2° 2θ).

In some embodiments, the Compound I gentisic acid is characterized by an XRPD pattern comprising peaks at 4.4°, 8.7°, and 14.9° 2θ (±0.2° 2θ). In some embodiments, the XRPD pattern further comprises one or more additional peaks at 12.9°, 17.3°, 19.5°, 24.8°, 25.7°, or 26.3° 2θ (±0.2° 2θ). In some embodiments, the XRPD pattern further comprises two or more additional peaks at 12.9°, 17.3°, 19.5°, 24.8°, 25.7°, or 26.3° 2θ (±0.2° 2θ). In some embodiments, the XRPD pattern further comprises three or more additional peaks at 12.9°, 17.3°, 19.5°, 24.8°, 25.7°, or 26.3° 2θ (±0.2° 2θ). In some embodiments, the XRPD pattern further comprises four or more additional peaks at 12.9°, 17.3°, 19.5°, 24.8°, 25.7°, or 26.3° 2θ (±0.2° 2θ). In some embodiments, the XRPD pattern further comprises five or more additional peaks at 12.9°, 17.3°, 19.5°, 24.8°, 25.7°, or 26.3° 2θ (±0.2° 2θ). In some embodiments, the XRPD pattern further comprises additional peaks at 12.9°, 17.3°, 19.5°, 24.8°, 25.7°, and 26.3° 2θ (±0.2° 2θ).

In some embodiments, the Compound I gentisic acid is characterized by an XRPD pattern comprising peaks at 12.9°, 24.8°, and 25.7° 2θ (±0.2° 2θ). In some embodiments, the XRPD pattern further comprises one or more additional peaks at 4.4°, 8.7°, 14.9°, 17.3°, 19.5°, or 26.3° 2θ (±0.2° 2θ). In some embodiments, the XRPD pattern further comprises two or more additional peaks at 4.4°, 8.7°, 14.9°, 24.8°, or 26.3°2θ (±0.2°2θ). In some embodiments, the XRPD pattern further comprises three or more additional peaks at 4.4°, 8.7°, 14.9°, 24.8°, or 26.3°2θ (±0.2°2θ). In some embodiments, the XRPD pattern further comprises four or more additional peaks at 4.4°, 8.7°, 14.9°, 24.8°, or 26.3°2θ (±0.2°2θ). In some embodiments, the XRPD pattern further comprises five or more additional peaks at 4.4°, 8.7°, 14.9°, 24.8°, or 26.3°2θ (±0.2°2θ). In some embodiments, the XRPD pattern further comprises additional peaks at 4.4°, 8.7°, 14.9°, 24.8°, and 26.3°2θ (±0.2°2θ).

In some embodiments, the Compound I gentisic acid is characterized by an XRPD pattern comprising three or more peaks at 4.4°, 8.7°, 12.9°, 14.9°, 24.8°, or 25.7°2θ (±0.2°2θ).

In some embodiments, the Compound I gentisic acid is characterized by an XRPD pattern comprising four or more peaks at 4.4°, 8.7°, 12.9°, 14.9°, 24.8°, or 25.7°2θ (±0.2°2θ). In some embodiments, the Compound I gentisic acid is characterized by an XRPD pattern comprising five or more peaks at 4.4°, 8.7°, 12.9°, 14.9°, 24.8°, or 25.7°2θ (±0.2°2θ). In some embodiments, the Compound I gentisic acid is characterized by an XRPD pattern comprising peaks at 4.4°, 8.7°, 12.9°, 14.9°, 24.8°, and 25.7°2θ (±0.2°2θ).

In some embodiments, the Compound I gentisic acid is characterized by an XRPD pattern comprising peaks at 4.4°, 8.7°, 12.9°, 14.9°, 17.3°, 19.5°, 24.8°, 25.7°, and 26.3°2θ (±0.2°2θ). In some embodiments, the Compound I gentisic acid is characterized by an XRPD pattern substantially as shown in FIG. 2. In some embodiments, the Compound I gentisic acid is characterized by a differential scanning calorimetry (DSC) thermogram having an endotherm with an onset of about 178° C. In some embodiments, the Compound I gentisic acid is characterized by a DSC thermogram substantially as shown in FIG. 3.

In some embodiments, the Compound I gentisic acid is characterized by: (a) an XRPD pattern comprising peaks at 4.4°, 8.7°, 12.9°, 14.9°, 17.3°, 19.5°, 24.8°, 25.7°, and 26.3°2θ (±0.2°2θ); and (b) a differential scanning calorimetry (DSC) thermogram having an endotherm with an onset of about 178° C. In some embodiments, the Compound I gentisic acid is characterized by: (a) an XRPD pattern substantially as shown in FIG. 2; and (b) a DSC thermogram substantially as shown in FIG. 3.

In some embodiments, Compound I gentisic acid is substantially free of Compound I Form I.

Hippuric Acid

In some embodiments, the present disclosure provides a crystalline form of (R)-2-((2-amino-7-fluoropyrido[3,2-d]pyrimidin-4-yl)amino)-2-methylhexan-1-ol hippurate, wherein the crystalline form is the Hippurate Salt. In some embodiments, the present disclosure provides a crystalline form of (R)-2-((2-amino-7-fluoropyrido[3,2-d]pyrimidin-4-yl)amino)-2-methylhexan-1-ol, wherein the crystalline form is the Compound I Hippuric Acid co-crystal. In some embodiments, the present disclosure provides a crystalline form of (R)-2-((2-amino-7-fluoropyrido[3,2-d]pyrimidin-4-yl)amino)-2-methylhexan-1-ol hippuric acid:

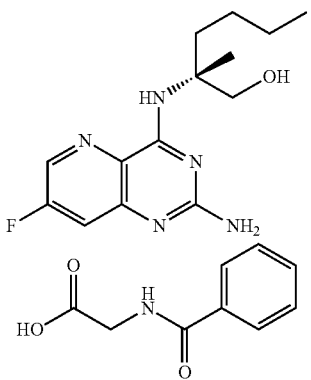

characterized by an XRPD pattern comprising three or more peaks at 2.9°, 5.0°, 7.6°, 10.4°, 12.6°, 17.6°, 19.0°, 25.2°, or 28.5° 2θ (±0.2° 2θ), Compound I hippuric acid.

In some embodiments, the Compound I hippuric acid is characterized by an XRPD pattern comprising four or more peaks at 2.9°, 5.0°, 7.6°, 10.4°, 12.6°, 17.6°, 19.0°, 25.2°, or 28.5° 2θ (±0.2° 2θ). In some embodiments, the Compound I hippuric acid is characterized by an XRPD pattern comprising five or more peaks at 2.9°, 5.0°, 7.6°, 10.4°, 12.6°, 17.6°, 19.0°, 25.2°, or 28.5° 2θ (±0.2° 2θ). In some embodiments, the Compound I hippuric acid is characterized by an XRPD pattern comprising six or more peaks at 2.9°, 5.0°, 7.6°, 10.4°, 12.6°, 17.6°, 19.0°, 25.2°, or 28.5° 2θ (±0.2° 2θ). In some embodiments, the Compound I hippuric acid is characterized by an XRPD pattern comprising seven or more peaks at 2.9°, 5.0°, 7.6°, 10.4°, 12.6°, 17.6°, 19.0°, 25.2°, or 28.5° 2θ (±0.2° 2θ). In some embodiments, the Compound I hippuric acid is characterized by an XRPD pattern comprising eight or more peaks at 2.9°, 5.0°, 7.6°, 10.4°, 12.6°, 17.6°, 19.0°, 25.2°, or 28.5° 2θ (±0.2° 2θ).

In some embodiments, the Compound I hippuric acid is characterized by an XRPD pattern comprising peaks at 5.0°, 12.6°, and 25.2° 2θ (±0.2° 2θ). In some embodiments, the XRPD pattern further comprises one or more additional peaks at 2.9°, 7.6°, 10.4°, 17.6°, 19.0°, or 28.5° 2θ (±0.2° 2θ). In some embodiments, the XRPD pattern further comprises two or more additional peaks at 2.9°, 7.6°, 10.4°, 17.6°, 19.0°, or 28.5° 2θ (±0.2° 2θ). In some embodiments, the XRPD pattern further comprises three or more additional peaks at 2.9°, 7.6°, 10.4°, 17.6°, 19.0°, or 28.5° 2θ (±0.2° 2θ). In some embodiments, the XRPD pattern further comprises four or more additional peaks at 2.9°, 7.6°, 10.4°, 17.6°, 19.0°, or 28.5° 2θ (±0.2° 2θ). In some embodiments, the XRPD pattern further comprises five or more additional peaks at 2.9°, 7.6°, 10.4°, 17.6°, 19.0°, or 28.5° 2θ (±0.2° 2θ). In some embodiments, the XRPD pattern further comprises additional peaks at 2.9°, 7.6°, 10.4°, 17.6°, 19.0°, and 28.5° 2θ (±0.2° 2θ).

In some embodiments, the Compound I hippuric acid is characterized by an XRPD pattern comprising peaks at 2.9°, 7.6°, and 19.0° 2θ (±0.2° 2θ). In some embodiments, the XRPD pattern further comprises one or more additional peaks at 5.0°, 10.4°, 12.6°, 17.6°, 25.2°, or 28.5° 2θ (±0.2° 2θ). In some embodiments, the XRPD pattern further comprises two or more additional peaks at 5.0°, 10.4°, 12.6°, 17.6°, 25.2°, or 28.5° 2θ (±0.2° 2θ). In some embodiments, the XRPD pattern further comprises three or more additional peaks at 5.0°, 10.4°, 12.6°, 17.6°, 25.2°, or 28.5° 2θ (±0.2° 2θ). In some embodiments, the XRPD pattern further comprises four or more additional peaks at 5.0°, 10.4°, 12.6°, 17.6°, 25.2°, or 28.5° 2θ (±0.2° 2θ). In some embodiments, the XRPD pattern further comprises five or more additional peaks at 5.0°, 10.4°, 12.6°, 17.6°, 25.2°, or 28.5° 2θ (±0.2° 2θ). In some embodiments, the XRPD pattern further comprises additional peaks at 5.0°, 10.4°, 12.6°, 17.6°, 25.2°, and 28.5° 2θ (0.2° 2θ).

In some embodiments, the Compound I hippuric acid is characterized by an XRPD pattern comprising peaks at 2.9°, 5.0°, 7.6°, 10.4°, 12.6°, 19.0°, 17.6°, 25.2°, and 28.5° 2θ (±0.2° 2θ). In some embodiments, the Compound I hippuric acid is characterized by an XRPD pattern substantially as shown in FIG. 6. In some embodiments, the Compound I hippuric acid is characterized by a differential scanning calorimetry (DSC) thermogram having an endotherm with an onset of about 127° C. In some embodiments, the Compound I hippuric acid is characterized by a DSC thermogram substantially as shown in FIG. 7.

In some embodiments, the Compound I hippuric acid is characterized by: (a) an XRPD pattern comprising peaks at 2.9°, 5.0°, 7.6°, 10.4°, 12.6°, 19.0°, 17.6°, 25.2°, and 28.5° 2θ (±0.2° 2θ); and (b) a differential scanning calorimetry (DSC) thermogram having an endotherm with an onset of about 127° C. In some embodiments, the Compound I hippuric acid is characterized by: (a) an XRPD pattern substantially as shown in FIG. 6; and (b) a DSC thermogram substantially as shown in FIG. 7.

In some embodiments, Compound I hippuric acid is substantially free of Compound I Form I.

Phosphoric Acid Form I

In some embodiments, the present disclosure provides a crystalline form of (R)-2-((2-amino-7-fluoropyrido[3,2-d]pyrimidin-4-yl)amino)-2-methylhexan-1-ol phosphate, wherein the crystalline form is the Phosphate Salt Form I. In some embodiments, the present disclosure provides a crystalline form of (R)-2-((2-amino-7-fluoropyrido[3,2-d]pyrimidin-4-yl)amino)-2-methylhexan-1-ol, wherein the crystalline form is the Compound I Phosphoric Acid Form I co-crystal. In some embodiments, the present disclosure provides a crystalline form of (R)-2-((2-amino-7-fluoropyrido[3,2-d]pyrimidin-4-yl)amino)-2-methylhexan-1-ol phosphoric acid:

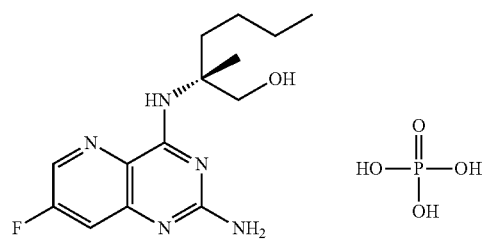

characterized by an XRPD pattern comprising three or more peaks at 3.7°, 6.1°, 7.1°, 12.10, 14.2°, 21.6°, 24.0°, 27.4°, or 28.2° 2θ (±0.2° 2θ), phosphate salt Form I.

In some embodiments, the phosphate salt Form I is characterized by an XRPD pattern comprising four or more peaks at 3.7°, 6.1, 7.1, 12.1°, 14.2°, 21.6°, 24.0°, 27.4°, or 28.2° 2θ (+0.2° 2θ). In some embodiments, the phosphate salt Form I is characterized by an XRPD pattern comprising five or more peaks at 3.7°, 6.1°, 7.1°, 12.1, 14.2°, 21.6°, 24.0°, 27.4°, or 28.2° 2θ (±0.2° 2θ). In some embodiments, the phosphate salt Form I is characterized by an XRPD pattern comprising six or more peaks at 3.7°, 6.1, 7.1, 12.1°, 14.2°, 21.6°, 24.0°, 27.4°, or 28.2° 2θ (±0.2° 2θ). In some embodiments, the phosphate salt Form I is characterized by an XRPD pattern comprising seven or more peaks at 3.7°, 6.1, 7.1, 12.1°, 14.2°, 21.6°, 24.0°, 27.4°, or 28.2° 2θ (±0.2° 2θ). In some embodiments, the phosphate salt Form I is characterized by an XRPD pattern comprising eight or more peaks at 3.7°, 6.1°, 7.1°, 12.1°, 14.2°, 21.6°, 24.0°, 27.4°, or 28.2° 2θ (±0.2° 2θ).

In some embodiments, the phosphate salt Form I is characterized by an XRPD pattern comprising peaks at 3.7°, 6.1, and 7.1° 2θ (±0.2° 2θ). In some embodiments, the XRPD pattern further comprises one or more additional peaks at 12.1°, 14.2°, 21.6°, 24.0°, 27.4°, or 28.2° 2θ (±0.2° 2θ). In some embodiments, the XRPD pattern further comprises two or more additional peaks at 12.1°, 14.2°, 21.6°, 24.0°, 27.4°, or 28.2° 2θ (±0.2° 2θ). In some embodiments, the XRPD pattern further comprises three or more additional peaks at 12.1°, 14.2°, 21.6°, 24.0°, 27.4°, or 28.2° 2θ (±0.2° 2θ). In some embodiments, the XRPD pattern further comprises four or more additional peaks at 12.10, 14.2°, 21.6°, 24.0°, 27.4°, or 28.2° 2θ (±0.2° 2θ). In some embodiments, the XRPD pattern further comprises five or more additional peaks at 12.1, 14.2°, 21.6°, 24.0°, 27.4°, or 28.2° 2θ (±0.2° 2θ). In some embodiments, the XRPD pattern further comprises additional peaks at 12.1°, 14.2°, 21.6°, 24.0°, 27.4°, and 28.2° 2θ (±0.2° 2θ).

In some embodiments, the phosphate salt Form I is characterized by an XRPD pattern comprising peaks at 14.2°, 27.4°, and 28.2° 2θ (±0.2° 2θ). In some embodiments, the XRPD pattern further comprises one or more additional peaks at 3.7°, 6.1°, 7.1°, 12.1°, 21.6°, or 24.0°2θ (±0.2°2θ). In some embodiments, the XRPD pattern further comprises two or more additional peaks at 3.7°, 6.1°, 7.1°, 12.1°, 21.6°, or 24.0°2θ (±0.2° 2θ). In some embodiments, the XRPD pattern further comprises three or more additional peaks at 3.7°, 6.1°, 7.1°, 12.1°, 21.6°, or 24.0°2θ (±0.2°2θ). In some embodiments, the XRPD pattern further comprises four or more additional peaks at 3.7°, 6.1°, 7.1°, 12.1°, 21.6°, or 24.0°2θ (±0.2°2θ). In some embodiments, the XRPD pattern further comprises five or more additional peaks at 3.7°, 6.1°, 7.1°, 12.1°, 21.6°, or 24.0°2θ (±0.2°2θ). In some embodiments, the XRPD pattern further comprises additional peaks at 3.7°, 6.1°, 7.1°, 12.1°, 21.6°, and 24.0°2θ (±0.2° 2θ).

In some embodiments, the phosphate salt Form I is characterized by an XRPD pattern comprising three or more peaks at 3.7°, 6.1°, 7.1°, 14.2°, 27.4°, or 28.2°2θ (±0.2°2θ). In some embodiments, the phosphate salt Form I is characterized by an XRPD pattern comprising four or more peaks at 3.7°, 6.1°, 7.1°, 14.2°, 27.4°, or 28.2°2θ (±0.2°2θ). In some embodiments, the phosphate salt Form I is characterized by an XRPD pattern comprising five or more peaks at 3.7°, 6.1°, 7.1°, 14.2°, 27.4°, or 28.2°2θ (±0.2°2θ). In some embodiments, the phosphate salt Form I is characterized by an XRPD pattern comprising peaks at 3.7°, 6.1°, 7.1°, 14.2°, 27.4°, and 28.2°2θ (±0.2°2θ).

In some embodiments, the phosphate salt Form I is characterized by an XRPD pattern comprising peaks at 3.7°, 6.1°, 7.1°, 12.1°, 14.2°, 21.6°, 24.0°, 27.4°, and 28.2°2θ (±0.2°2θ).

In some embodiments, the phosphate salt Form I is characterized by an XRPD pattern substantially as shown in FIG. 10. In some embodiments, the phosphate salt Form I is characterized by a differential scanning calorimetry (DSC) thermogram having an endotherm with an onset of about 43° C. In some embodiments, the DSC thermogram has a second endotherm with an onset of about 118° C. In some embodiments, the DSC thermogram has a third endotherm with an onset of about 202° C. In some embodiments, the phosphate salt Form I is characterized by a differential scanning calorimetry (DSC) thermogram having endotherms with an onset of about 43° C., about 118° C., and about 202° C. In some embodiments, the phosphate salt Form I is characterized by a DSC thermogram substantially as shown in FIG. 11.

In some embodiments, the phosphate salt Form I is characterized by: (a) an XRPD pattern comprising peaks at 3.7°, 6.1°, 7.1°, 12.1°, 14.2°, 21.6°, 24.0°, 27.4°, and 28.2°2θ (±0.2°2θ); and (b) a differential scanning calorimetry (DSC) thermogram having endotherms with an onset of about 43° C., about 118° C., and about 202° C. In some embodiments, the phosphate salt Form I is characterized by: (a) an XRPD pattern substantially as shown in FIG. 10; and (b) a DSC thermogram substantially as shown in FIG. 11.

In some embodiments, Compound I phosphoric acid Form I is substantially free of Compound I Form I.

Phosphoric Acid Form II

In some embodiments, the present disclosure provides a crystalline form of (R)-2-((2-amino-7-fluoropyrido[3,2-d]pyrimidin-4-yl)amino)-2-methylhexan-1-ol phosphate, wherein the crystalline form is the Phosphate Salt Form II. In some embodiments, the present disclosure provides a crystalline form of (R)-2-((2-amino-7-fluoropyrido[3,2-d]pyrimidin-4-yl)amino)-2-methylhexan-1-ol, wherein the crystalline form is the Compound I Phosphoric Acid Form II co-crystal. In some embodiments, the present disclosure provides a crystalline form of (R)-2-((2-amino-7-fluoropyrido[3,2-d]pyrimidin-4-yl)amino)-2-methylhexan-1-ol phosphoric acid:

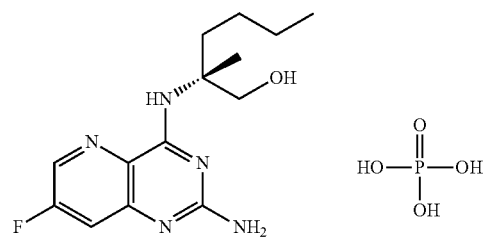

characterized by an XRPD pattern comprising three or more peaks at 5.4°, 6.3°, 15.8°, 18.1°, 18.9°, 20.6°, 24.1°, 26.7°, or 27.4° 2θ (±0.2° 2θ), phosphate salt Form II.

In some embodiments, the phosphate salt Form II is characterized by an XRPD pattern comprising four or more peaks at 5.4°, 6.3°, 15.8°, 18.1°, 18.9°, 20.6°, 24.1°, 26.7°, or 27.4° 2θ (+0.2° 2θ). In some embodiments, the phosphate salt Form II is characterized by an XRPD pattern comprising five or more peaks at 5.4°, 6.3°, 15.8°, 18.1°, 18.9°, 20.6°, 24.1°, 26.7°, or 27.4° 2θ (±0.2° 2θ). In some embodiments, the phosphate salt Form II is characterized by an XRPD pattern comprising six or more peaks at 5.4°, 6.3°, 15.8°, 18.1°, 18.9°, 20.6°, 24.1°, 26.7°, or 27.4° 2θ (±0.2° 2θ). In some embodiments, the phosphate salt Form II is characterized by an XRPD pattern comprising seven or more peaks at 5.4°, 6.3°, 15.8°, 18.1°, 18.9°, 20.6°, 24.1°, 26.7°, or 27.4° 2θ (±0.2° 2θ). In some embodiments, the phosphate salt Form II is characterized by an XRPD pattern comprising eight or more peaks at 5.4°, 6.3°, 15.8°, 18.1°, 18.9°, 20.6°, 24.1°, 26.7°, or 27.4° 2θ (±0.2° 2θ).

In some embodiments, the phosphate salt Form II is characterized by an XRPD pattern comprising peaks at 5.4°, 6.3°, and 26.7° 2θ (±0.2° 2θ). In some embodiments, the XRPD pattern further comprises one or more additional peaks at 15.8°, 18.1°, 18.9°, 20.6°, 24.1°, or 27.4° 2θ (±0.2° 2θ). In some embodiments, the XRPD pattern further comprises two or more additional peaks at 15.8°, 18.1°, 18.9°, 20.6°, 24.1°, or 27.4° 2θ (±0.2° 2θ). In some embodiments, the XRPD pattern further comprises three or more additional peaks at 15.8°, 18.1°, 18.9°, 20.6°, 24.1°, or 27.4° 2θ (±0.2° 2θ). In some embodiments, the XRPD pattern further comprises four or more additional peaks at 15.8°, 18.1°, 18.9°, 20.6°, 24.1°, or 27.4° 2θ (±0.2°2θ). In some embodiments, the XRPD pattern further comprises five or more additional peaks at 15.8°, 18.1°, 18.9°, 20.6°, 24.1°, or 27.4° 2θ (±0.2° 2θ). In some embodiments, the XRPD pattern further comprises additional peaks at 15.8°, 18.1°, 18.9°, 20.6°, 24.1°, and 27.4° 2θ (±0.2° 2θ).

In some embodiments, the phosphate salt Form II is characterized by an XRPD pattern comprising peaks at 15.8°, 18.1°, and 18.9° 2θ (±0.2°2θ). In some embodiments, the XRPD pattern further comprises one or more additional peaks at 5.4°, 6.3°, 20.6°, 24.1°, 26.7°, or 27.4° 2θ (±0.2°2θ). In some embodiments, the XRPD pattern further comprises two or more additional peaks at 5.4°, 6.3°, 20.6°, 24.1°, 26.7°, or 27.4° 2θ (±0.2°2θ). In some embodiments, the XRPD pattern further comprises three or more additional peaks at 5.4°, 6.3°, 20.6°, 24.1°, 26.7°, or 27.4° 2θ (±0.2°2θ). In some embodiments, the XRPD pattern further comprises four or more additional peaks at 5.4°, 6.3°, 20.6°, 24.1°, 26.7°, or 27.4° 2θ (±0.2° 2θ). In some embodiments, the XRPD pattern further comprises five or more additional peaks at 5.4°, 6.3°, 20.6°, 24.1°, 26.7°, or 27.4° 2θ (±0.2°2θ). In some embodiments, the XRPD pattern further comprises additional peaks at 5.4°, 6.3°, 20.6°, 24.1°, 26.7°, and 27.4° 2θ (±0.2°2θ).

In some embodiments, the phosphate salt Form II is characterized by an XRPD pattern comprising three or more peaks at 5.4°, 6.3°, 15.8°, 18.1°, 18.9°, or 26.7° 2θ (±0.2° 2θ). In some embodiments, the phosphate salt Form II is characterized by an XRPD pattern comprising four or more peaks at 5.4°, 6.3°, 15.8°, 18.1°, 18.9°, or 26.7° 2θ (±0.2°2θ). In some embodiments, the phosphate salt Form II is characterized by an XRPD pattern comprising five or more peaks at 5.4°, 6.3°, 15.8°, 18.1°, 18.9°, or 26.7° 2θ (±0.2°2θ). In some embodiments, the phosphate salt Form II is characterized by an XRPD pattern comprising peaks at 5.4°, 6.3°, 15.8°, 18.1°, 18.9°, and 26.7° 2θ (±0.2° 2θ).

In some embodiments, the phosphate salt Form II is characterized by an XRPD pattern comprising peaks at 5.4°, 6.3°, 15.8°, 18.1°, 18.9°, 20.6°, 24.1°, 26.7°, and 27.4° 2θ (±0.2°2θ).

In some embodiments, the phosphate salt Form II is characterized by an XRPD pattern substantially as shown in FIG. 13. In some embodiments, the phosphate salt Form II is characterized by a differential scanning calorimetry (DSC) thermogram having an endotherm with an onset of about 42° C. In some embodiments, the DSC thermogram has a second endotherm with an onset of about 95° C. In some embodiments, the phosphate salt Form II is characterized by a differential scanning calorimetry (DSC) thermogram having endotherms with an onset of about 42° C. and about 95° C. In some embodiments, the phosphate salt Form II is characterized by a DSC thermogram substantially as shown in FIG. 14.

In some embodiments, the phosphate salt Form II is characterized by: (a) an XRPD pattern comprising peaks at 5.4°, 6.3°, 15.8°, 18.1°, 18.9°, 20.6°, 24.1°, 26.7°, and 27.4°2θ (±0.2°2θ); and (b) a differential scanning calorimetry (DSC) thermogram having endotherms with an onset of about 42° C. and about 95° C. In some embodiments, the phosphate salt Form II is characterized by: (a) an XRPD pattern substantially as shown in FIG. 13; and (b) a DSC thermogram substantially as shown in FIG. 14.

In some embodiments, Compound I phosphoric acid Form II is substantially free of Compound I Form I.

Succinic Acid

In some embodiments, the present disclosure provides a crystalline form of (R)-2-((2-amino-7-fluoropyrido[3,2-d]pyrimidin-4-yl)amino)-2-methylhexan-1-ol succinate wherein the crystalline form is the Succinate Salt. In some embodiments, the present disclosure provides a crystalline form of (R)-2-((2-amino-7-fluoropyrido[3,2-d]pyrimidin-4-yl)amino)-2-methylhexan-1-ol, wherein the crystalline form is the Compound I Succinic Acid co-crystal. In some embodiments, the present disclosure provides a crystalline form of (R)-2-((2-amino-7-fluoropyrido[3,2-d]pyrimidin-4-yl)amino)-2-methylhexan-1-ol succinic acid:

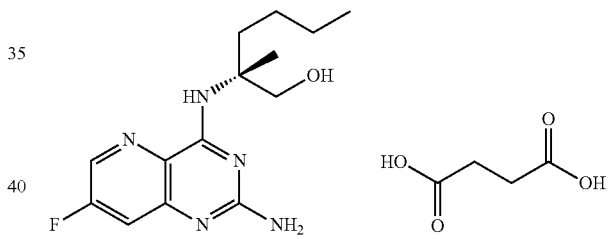

characterized by an XRPD pattern comprising three or more peaks at 4.6°, 6.8°, 9.3°, 13.2°, 17.5°, 18.7°, 19.0°, 25.7°, or 27.0°2θ (±0.2°2θ), Compound I succinic acid.

In some embodiments, the Compound I succinic acid is characterized by an XRPD pattern comprising four or more peaks at 4.6°, 6.8°, 9.3°, 13.2°, 17.5°, 18.7°, 19.0°, 25.7°, or 27.0°2θ (±0.2°2θ). In some embodiments, the Compound I succinic acid is characterized by an XRPD pattern comprising five or more peaks at 4.6°, 6.8°, 9.3°, 13.2°, 17.5°, 18.7°, 19.0°, 25.7°, or 27.0°2θ (±0.2°2θ). In some embodiments, the Compound I succinic acid is characterized by an XRPD pattern comprising six or more peaks at 4.6°, 6.8°, 9.3°, 13.2°, 17.5°, 18.7°, 19.0°, 25.7°, or 27.0°2θ (±0.2°2θ). In some embodiments, the Compound I succinic acid is characterized by an XRPD pattern comprising seven or more peaks at 4.6°, 6.8°, 9.3°, 13.2°, 17.5°, 18.7°, 19.0°, 25.7°, or 27.0°2θ (±0.2°2θ). In some embodiments, the Compound I succinic acid is characterized by an XRPD pattern comprising eight or more peaks at 4.6°, 6.8°, 9.3°, 13.2°, 17.5°, 18.7°, 19.0°, 25.7°, or 27.0° 2θ (±0.2° 2θ).

In some embodiments, the Compound I succinic acid is characterized by an XRPD pattern comprising peaks at 4.6°, 6.8°, and 9.3° 2θ (±0.2° 2θ). In some embodiments, the XRPD pattern further comprises one or more additional peaks at 13.2°, 17.5°, 18.7°, 19.0°, 25.7°, or 27.0° 2θ (±0.2° 2θ). In some embodiments, the XRPD pattern further comprises two or more additional peaks at 13.2°, 17.5°, 18.7°, 19.0°, 25.7°, or 27.0° 2θ (±0.2° 2θ). In some embodiments, the XRPD pattern further comprises three or more additional peaks at 13.2°, 17.5°, 18.7°, 19.0°, 25.7°, or 27.0° 2θ (±0.2° 2θ). In some embodiments, the XRPD pattern further comprises four or more additional peaks at 13.2°, 17.5°, 18.7°, 19.0°, 25.7°, or 27.0° 2θ (±0.2° 2θ). In some embodiments, the XRPD pattern further comprises five or more additional peaks at 13.2°, 17.5°, 18.7°, 19.0°, 25.7°, or 27.0° 2θ (±0.2° 2θ). In some embodiments, the XRPD pattern further comprises additional peaks at 13.2°, 17.5°, 18.7°, 19.0°, 25.7°, and 27.0° 2θ (±0.2° 2θ).

In some embodiments, the Compound I succinic acid is characterized by an XRPD pattern comprising peaks at 18.7°, 19.0°, and 25.7° 2θ (±0.2° 2θ). In some embodiments, the XRPD pattern further comprises one or more additional peaks at 4.6°, 6.8°, 9.3°, 13.2°, 17.5°, or 27.0° 2θ (±0.2° 2θ). In some embodiments, the XRPD pattern further comprises two or more additional peaks at 4.6°, 6.8°, 9.3°, 13.2°, 17.5°, or 27.0° 2θ (±0.2° 2θ). In some embodiments, the XRPD pattern further comprises three or more additional peaks at 4.6°, 6.8°, 9.3°, 13.2°, 17.5°, or 27.0° 2θ (±0.2° 2θ). In some embodiments, the XRPD pattern further comprises four or more additional peaks at 4.6°, 6.8°, 9.3°, 13.2°, 17.5°, or 27.0° 2θ (±0.2° 2θ). In some embodiments, the XRPD pattern further comprises five or more additional peaks at 4.6°, 6.8°, 9.3°, 13.2°, 17.5°, or 27.0° 2θ (±0.2° 2θ). In some embodiments, the XRPD pattern further comprises additional peaks at 4.6°, 6.8°, 9.3°, 13.2°, 17.5°, and 27.0° 2θ (±0.2° 2θ).

In some embodiments, the Compound I succinic acid is characterized by an XRPD pattern comprising three or more peaks at 4.6°, 6.8°, 9.3°, 18.7°, 19.0°, or 25.7° 2θ (±0.2° 2θ).

In some embodiments, the Compound I succinic acid is characterized by an XRPD pattern comprising four or more peaks at 4.6°, 6.8°, 9.3°, 18.7°, 19.0°, or 25.7° 2θ (±0.2° 2θ). In some embodiments, the Compound I succinic acid is characterized by an XRPD pattern comprising five or more peaks at 4.6°, 6.8°, 9.3°, 18.7°, 19.0°, or 25.7° 2θ (±0.2° 2θ). In some embodiments, the Compound I succinic acid is characterized by an XRPD pattern comprising peaks at 4.6°, 6.8°, 9.3°, 18.7°, 19.0°, and 25.7° 2θ (±0.2° 2θ).

In some embodiments, the Compound I succinic acid is characterized by an XRPD pattern comprising peaks at 4.6°, 6.8°, 9.3°, 13.2°, 17.5°, 18.7°, 19.0°, 25.7°, and 27.0° 2θ (±0.2°2θ). In some embodiments, the Compound I succinic acid is characterized by an XRPD pattern substantially as shown in FIG. 16. In some embodiments, the Compound I succinic acid is characterized by a differential scanning calorimetry (DSC) thermogram having an endotherm with an onset of about 96° C. In some embodiments, the DSC thermogram has a second endotherm with an onset of about 115° C. In some embodiments, the Compound I succinic acid is characterized by a differential scanning calorimetry (DSC) thermogram having endotherms with an onset of about 96° C. and about 115° C. In some embodiments, the Compound I succinic acid is characterized by a DSC thermogram substantially as shown in FIG. 17.

In some embodiments, the Compound I succinic acid is characterized by: (a) an XRPD pattern comprising peaks at 4.6°, 6.8°, 9.3°, 13.2°, 17.5°, 18.7°, 19.0°, 25.7°, and 27.0° 2θ (±0.2°2θ); and (b) a differential scanning calorimetry (DSC) thermogram having endotherms with an onset of about 96° C. and about 115° C. In some embodiments, the Compound I succinic acid is characterized by: (a) an XRPD pattern substantially as shown in FIG. 16; and (b) a DSC thermogram substantially as shown in FIG. 17.

In some embodiments, Compound I succinic acid is substantially free of Compound I Form I.

Ethanedisulfonic Acid Form I

In some embodiments, the present disclosure provides a crystalline form of (R)-2-((2-amino-7-fluoropyrido[3,2-d]pyrimidin-4-yl)amino)-2-methylhexan-1-ol edisylate, wherein the crystalline form is the Edysilate Salt Form I. In some embodiments, the present disclosure provides a crystalline form of (R)-2-((2-amino-7-fluoropyrido[3,2-d]pyrimidin-4-yl)amino)-2-methylhexan-1-ol, wherein the crystalline form is the Compound I Ethanedisulfonic Acid Form I co-crystal. In some embodiments, the present disclosure provides a crystalline form of (R)-2-((2-amino-7-fluoropyrido[3,2-d]pyrimidin-4-yl)amino)-2-methylhexan-1-ol ethanedisulfonic acid:

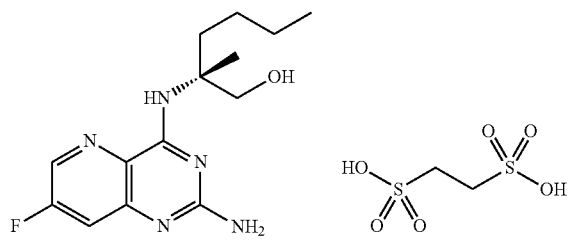

characterized by an XRPD pattern comprising three or more peaks at 4.4°79° 8.7°, 13.0°, 16.6°, 20.6°, 21.1°, 22.1°, or 26.0° 2θ (±0.2°2θ), Compound I ethanedisulfonic acid Form I.

In some embodiments, the Compound I ethanedisulfonic acid Form I is characterized by an XRPD pattern comprising four or more peaks at 4.4°, 79° 8.7°, 13.0°, 16.6°, 20.6°, 21.1°, 22.1°, or 26.0° 2θ (±0.2°2θ). In some embodiments, the Compound I ethanedisulfonic acid Form I is characterized by an XRPD pattern comprising five or more peaks at 4.4°79° 8.7°, 13.0°, 16.6°, 20.6°, 21.1°, 22.1°, or 26.0° 2θ (±0.2° 2θ). In some embodiments, the Compound I ethanedisulfonic acid Form I is characterized by an XRPD pattern comprising six or more peaks at 4.4°79° 8.7°, 13.0°, 16.6°, 20.6°, 21.1°, 22.1°, or 26.0° 2θ (±0.2°2θ). In some embodiments, the Compound I ethanedisulfonic acid Form I is characterized by an XRPD pattern comprising seven or more peaks at 4.4°79° 8.7°, 13.0°, 16.6°, 20.6°, 21.1°, 22.1°, or 26.0° 2θ (±0.2°2θ). In some embodiments, the Compound I ethanedisulfonic acid Form I is characterized by an XRPD pattern comprising eight or more peaks at 4.4°79° 8.7°, 13.0°, 16.6°, 20.6°, 21.1°, 22.1°, or 26.0° 2θ (±0.2° 2θ).

In some embodiments, the Compound I ethanedisulfonic acid Form I is characterized by an XRPD pattern comprising peaks at 4.4°, 8.7°, and 22.1° 2θ (±0.2°2θ). In some embodiments, the XRPD pattern further comprises one or more additional peaks at 7.9°, 13.0°, 16.6°, 20.6°, 21.1°, or 26.0° 2θ (±0.2°2θ). In some embodiments, the XRPD pattern further comprises two or more additional peaks at 7.9°, 13.0°, 16.6°, 20.6°, 21.1°, or 26.0° 2θ (±0.2°2θ). In some embodiments, the XRPD pattern further comprises three or more additional peaks at 7.9°, 13.0°, 16.6°, 20.6°, 21.1°, or 26.0° 2θ (±0.2°2θ). In some embodiments, the XRPD pattern further comprises four or more additional peaks at 7.9°, 13.0°, 16.6°, 20.6°, 21.1°, or 26.0° 2θ (±0.2°2θ). In some embodiments, the XRPD pattern further comprises five or more additional peaks at 7.9°, 13.0°, 16.6°, 20.6°, 21.1°, or 26.0° 2θ (±0.2° 2θ). In some embodiments, the XRPD pattern further comprises additional peaks at 7.9°, 13.0°, 16.6°, 20.6°, 21.1°, and 26.0° 2θ (±0.2°2θ).

In some embodiments, the Compound I ethanedisulfonic acid Form I is characterized by an XRPD pattern comprising peaks at 7.9°, 13.0°, and 21.1° 2θ (±0.2°2θ). In some embodiments, the XRPD pattern further comprises one or more additional peaks 4.4°8.7°, 16.6°, 20.6°, 22.1°, or 26.0° 2θ (±0.2°2θ). In some embodiments, the XRPD pattern further comprises two or more additional peaks at 4.4°, 8.7°, 16.6°, 20.6°, 22.1°, or 26.0° 2θ (±0.2°2θ).

In some embodiments, the XRPD pattern further comprises three or more additional peaks at 4.4°, 8.7°, 16.6°, 20.6°, 22.1°, or 26.0° 2θ (±0.2°2θ). In some embodiments, the XRPD pattern further comprises four or more additional peaks at 4.4°, 8.7°, 16.6°, 20.6°, 22.1°, or 26.0° 2θ (±0.2°2θ). In some embodiments, the XRPD pattern further comprises five or more additional peaks at 4.4°, 8.7°, 16.6°, 20.6°, 22.1°, or 26.0° 2θ (±0.2°2θ). In some embodiments, the XRPD pattern further comprises additional peaks at 4.4°, 8.7°, 16.6°, 20.6°, 22.1°, and 26.0° 2θ (+0.2° 2θ).

In some embodiments, the Compound I ethanedisulfonic acid Form I is characterized by an XRPD pattern comprising three or more peaks at 4.4°, 79° 8.7°, 13.0°, 21.1° or 22.1° 2θ (±0.2°2θ). In some embodiments, the Compound I ethanedisulfonic acid Form I is characterized by an XRPD pattern comprising four or more peaks at 4.4°79° 8.7°, 13.0°, 21.1° or 22.1° 2θ (±0.2°2θ). In some embodiments, the Compound I ethanedisulfonic acid Form I is characterized by an XRPD pattern comprising five or more peaks at 4.4°79° 8.7°, 13.0°, 21.1° or 22.1° 2θ (±0.2°2θ). In some embodiments, the Compound I ethanedisulfonic acid Form I is characterized by an XRPD pattern comprising peaks at 4.4°79° 8.7°, 13.0°, 21.1° and 22.1° 2θ (±0.2° 2θ).

In some embodiments, the Compound I ethanedisulfonic acid Form I is characterized by an XRPD pattern comprising peaks at 4.4°79° 8.7°, 13.0°, 16.6°, 20.6°, 21.1°, 22.1°, and 26.0° 2θ (±0.2°2θ). In some embodiments, the Compound I ethanedisulfonic acid Form I is characterized by an XRPD pattern substantially as shown in FIG. 20.

In some embodiments, Compound I ethanesulfonic acid Form I is substantially free of Compound I Form I.

Ethanedisulfonic Acid Form II

In some embodiments, the present disclosure provides a crystalline form of (R)-2-((2-amino-7-fluoropyrido[3,2-d]pyrimidin-4-yl)amino)-2-methylhexan-1-ol edisylate, wherein the crystalline form is the Edysilate Salt Form II. In some embodiments, the present disclosure provides a crystalline form of (R)-2-((2-amino-7-fluoropyrido[3,2-d]pyrimidin-4-yl)amino)-2-methylhexan-1-ol, wherein the crystalline form is the Compound I Ethanedisulfonic Acid Form II co-crystal. In some embodiments, the present disclosure provides a crystalline form of (R)-2-((2-amino-7-fluoropyrido[3,2-d]pyrimidin-4-yl)amino)-2-methylhexan-1-ol ethanedisulfonic acid:

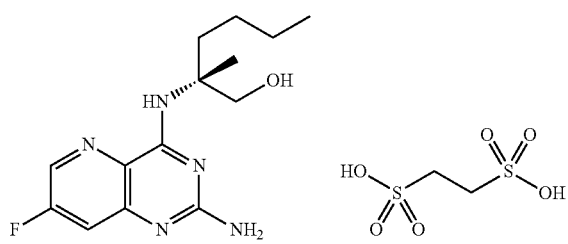

characterized by an XRPD pattern comprising three or more peaks at 4.5°, 5.6°, 8.4°, 12.9°, 13.4°, 16.6°, 17.9°, 18.3°, or 22.2° 2θ (±0.2°2θ), Compound I ethanedisulfonic acid Form II.

In some embodiments, the Compound I ethanedisulfonic acid Form II is characterized by an XRPD pattern comprising four or more peaks at 4.5°, 5.6°, 8.4°, 12.9°, 13.4°, 16.6°, 17.9°, 18.3°, or 22.2° 2θ (±0.2° 2θ). In some embodiments, the Compound I ethanedisulfonic acid Form II is characterized by an XRPD pattern comprising five or more peaks at 4.5°, 5.6°, 8.4°, 12.9°, 13.4°, 16.6°, 17.9°, 18.3°, or 22.2° 2θ (±0.2° 2θ). In some embodiments, the Compound I ethanedisulfonic acid Form II is characterized by an XRPD pattern comprising six or more peaks at 4.5°, 5.6°, 8.4°, 12.9°, 13.4°, 16.6°, 17.9°, 18.3°, or 22.2° 2θ (±0.2° 2θ). In some embodiments, the Compound I ethanedisulfonic acid Form II is characterized by an XRPD pattern comprising seven or more peaks at 4.5°, 5.6°, 8.4°, 12.9°, 13.4°, 16.6°, 17.9°, 18.3°, or 22.2° 2θ (±0.2° 2θ). In some embodiments, the Compound I ethanedisulfonic acid Form II is characterized by an XRPD pattern comprising eight or more peaks at 4.5°, 5.6°, 8.4°, 12.9°, 13.4°, 16.6°, 17.9°, 18.3°, or 22.2° 2θ (±0.2° 2θ).

In some embodiments, the Compound I ethanedisulfonic acid Form II is characterized by an XRPD pattern comprising peaks at 4.5°, 8.4°, and 22.2° 2θ (±0.2° 2θ). In some embodiments, the XRPD pattern further comprises one or more additional peaks at 5.6°, 12.9°, 13.4°, 16.6°, 17.9°, or 18.3° 2θ (±0.2° 2θ). In some embodiments, the XRPD pattern further comprises two or more additional peaks at 5.6°, 12.9°, 13.4°, 16.6°, 17.9°, or 18.3° 2θ (±0.2° 2θ). In some embodiments, the XRPD pattern further comprises three or more additional peaks at 5.6°, 12.9°, 13.4°, 16.6°, 17.9°, or 18.3° 2θ (±0.2° 2θ). In some embodiments, the XRPD pattern further comprises four or more additional peaks at 5.6°, 12.9°, 13.4°, 16.6°, 17.9°, or 18.3° 2θ (±0.2° 2θ). In some embodiments, the XRPD pattern further comprises five or more additional peaks at 5.6°, 12.9°, 13.4°, 16.6°, 17.9°, or 18.3° 2θ (±0.2° 2θ). In some embodiments, the XRPD pattern further comprises additional peaks at 5.6°, 12.9°, 13.4°, 16.6°, 17.9°, and 18.3° 2θ (±0.2° 2θ).

In some embodiments, the Compound I ethanedisulfonic acid Form II is characterized by an XRPD pattern comprising peaks at 12.9°, 13.4°, and 16.6° 2θ (±0.2° 2θ). In some embodiments, the XRPD pattern further comprises one or more additional peaks 4.5°, 5.6°, 8.4°, 17.9°, 18.3°, or 22.2° 2θ (±0.2° 2θ). In some embodiments, the XRPD pattern further comprises two or more additional peaks at 4.5°, 5.6°, 8.4°, 17.9°, 18.3°, or 22.2° 2θ (±0.2° 2θ).

In some embodiments, the XRPD pattern further comprises three or more additional peaks at 4.5°, 5.6°, 8.4°, 17.9°, 18.3°, or 22.2° 2θ (±0.2° 2θ). In some embodiments, the XRPD pattern further comprises four or more additional peaks at 4.5°, 5.6°, 8.4°, 17.9°, 18.3°, or 22.2° 2θ (±0.2° 2θ). In some embodiments, the XRPD pattern further comprises five or more additional peaks at 4.5°, 5.6°, 8.4°, 17.9°, 18.3°, or 22.2° 2θ (±0.2° 2θ). In some embodiments, the XRPD pattern further comprises additional peaks at 4.5°, 5.6°, 8.4°, 17.9°, 18.3°, and 22.2°2θ (±0.2°2θ).

In some embodiments, the Compound I ethanedisulfonic acid Form II is characterized by an XRPD pattern comprising three or more peaks at 4.5°, 8.4°, 12.9°, 13.4°, 16.6°, or 22.2°2θ (±0.2°2θ). In some embodiments, the Compound I ethanedisulfonic acid Form II is characterized by an XRPD pattern comprising four or more peaks at 4.5°, 8.4°, 12.9°, 13.4°, 16.6°, or 22.2°2θ (±0.2°2θ). In some embodiments, the Compound I ethanedisulfonic acid Form II is characterized by an XRPD pattern comprising five or more peaks at 4.5°, 8.4°, 12.9°, 13.4°, 16.6°, or 22.2°2θ (±0.2°2θ). In some embodiments, the Compound I ethanedisulfonic acid Form II is characterized by an XRPD pattern comprising peaks at 4.5°, 8.4°, 12.9°, 13.4°, 16.6°, and 22.2°2θ (±0.2°2θ).

In some embodiments, the Compound I ethanedisulfonic acid Form II is characterized by an XRPD pattern comprising peaks at 4.5°, 5.6°, 8.4°, 12.9°, 13.4°, 16.6°, 17.9°, 18.3°, and 22.2°2θ (±0.2°2θ). In some embodiments, the Compound I ethanedisulfonic acid Form II is characterized by an XRPD pattern substantially as shown in FIG. 21.

In some embodiments, Compound I ethanedisulfonic acid Form II is substantially free of Compound I Form I.

IV. Methods of Preparing Solid Forms of Compound I

The solid forms of Compound I can be prepared by a variety of methods. For example, Compound I can be dissolved in a single solvent system and allowed to crystallize. Alternatively, Compound I can be crystallized from a two-solvent system by dissolving Compound I in a solvent, and then adding an anti-solvent to the mixture causing Compound I to crystallize.

The solvent can be any solvent suitable to form a solution. Typically the solvent can be a polar solvent, which in some embodiments is a protic solvent. Other suitable solvents include non-polar solvents. Suitable solvents include, but are not limited to, water, alkanes such as heptanes, hexanes, and cyclohexane, petroleum ether, $C_1$-$C_3$ alcohols (methanol, ethanol, propanol, isopropanol), ethylene glycol and polyethylene glycol such as PEG400, alkanoates such as ethyl acetate, propyl acetate, isopropyl acetate, and butyl acetate, acetonitrile, alkanones such as acetone, butanone, methyl ethyl ketone (MEK), methyl propyl ketone (MPK) and methyl iso-butyl ketone (MIBK), ethers such as diethyl ether, methyl-t-butyl ether, tetrahydrofuran, methyl-tetrahydrofuran, 1,2-dimethoxy ethane and 1,4-dioxane, aromatics such as benzene and toluene, halogenated solvents such as methylene chloride, chloroform and carbon tetrachloride, dimethylsulfoxide (DMSO), and dimethylformamide (DMF). Suitable solvents also include, but are not limited to halogenated $C_1$-$C_3$ alcohols (trifluoromethanol, trifluoroethanol (TFE), hexafluoroisopropanol (HFIPA)). For example, the solvent can be a polar aprotic solvent such as dichloromethane, N-methylpyrrolidone, tetrahydrofuran, ethyl acetate, acetone, methyl ethyl ketone, dimethylformamide (DMF), acetonitrile (AcCN), dimethyl sulfoxide (DMSO), among others. The solvent can also be a polar protic solvent such as t-butanol, n-propanol, isopropanol, ethanol, methanol, acetic acid, water, among others. The solvent can also be a non-polar solvent, such as hexane, pentanes, petroleum ether, benzene, toluene, diethyl ether, methyl-t-butyl ether, tetrahydrofuran, methyl-tetrahydrofuran, 1,2-dimethoxy ethane and 1,4-dioxane, chloroform, and carbon tetrachloride.

Two or more solvents can be used in a solvent mixture in any suitable ratio. For example, the ratio of a first solvent and a second solvent can be from 10:1 to about 1:10 (volume/volume), or about 10:1 to 1:5, or 10:1 to 1:1, or 10:1 to 5:1, or 5:1 to 1:5, or 5:1 to 1:1, or 4:1 to 1:1, or 3:1 to 1:1, or 2:1 to 1:1. Other solvent ratios include about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9 or about 1:10 (volume/volume).

The methods of preparing solid forms of Compound I can be performed under any suitable reaction conditions. For example, the methods of preparing the crystalline forms of Compound I can be performed at any suitable temperature, such as, but not limited to, below room temperature, at room temperature, or above room temperature. In some embodiments, the temperature can be from about −78° C. to about 100° C., or from about 0° C. to about 50° C., or from about 10° C. to about 30° C. For example, the reaction mixture be at a temperature of about 20° C., or 25, 30, 35, 40, 45, 50, 55, 60, 65, 70, 75, 80, 85, 90, 95 or about 100° C. The reaction mixture can also be at a temperature of about 20° C., 15, 10, 5, 0, −5, −10, −20, −30, −40, −50, −60, −70 or about −78° C. In some embodiments, the temperature can be the reflux temperature of the particular solvent used in the method. In other embodiments, crystalline forms of Compound I can be heated above about 100° C. such that one crystalline form of Compound I forms a second crystalline form of Compound I.

The methods of preparing solid forms of Compound I can include a variety of other steps. For example, the solvent can be evaporated, a seed crystal can be added to the mixture, the mixture can be heated and cooled a single time or repeatedly, etc. For example, the methods can include heating the reaction mixture to a temperature of about 20° C., or 25, 30, 35, 40, 45, 50, 55, 60, 65, 70, 75, 80, 85, 90, 95 or about 100° C. The methods can also include cooling the reaction mixture to a temperature of about 20° C., 15, 10, 5, 0, −5, −10, −20, −30, −40, −50, −60, −70 or about −78° C. The temperature of the reaction mixture can be changed at any suitable rate. For example, the rate of temperature change can be from about 0.1° C./min to about 10° C./min.

The methods of preparing crystalline forms of Compound I can be performed for any suitable time. For example, the time can be for minutes, hours or days. In some embodiments, the time can be several hours, such as overnight. The methods of preparing crystalline forms of Compound I can be also be performed at any suitable pressure. For example, the pressure can be below atmospheric pressure, at about atmospheric pressure, or above atmospheric pressure.

Crystallization can be induced by methods known in the art, for example by mechanical means such as scratching or rubbing the contact surface of the reaction vessel with e.g. a glass rod. Optionally the saturated or supersaturated solution may be inoculated with seed crystals. The method preparing solid forms of Compound I can also include a seed crystal of crystalline Compound I.

Isolation of the desired crystalline form can be accomplished by removing the solvent and precipitating solvent from the crystals. Generally this is carried out by known methods, such as, filtration, suction filtration, decantation or centrifugation. Further isolation can be achieved by removing any excess of the solvent(s) from the crystalline form by methods known to the one skilled in the art as for example application of a vacuum, and/or by heating.

Form I

Crystalline Compound I Form I can be prepared by a variety of methods. In some embodiments, the present disclosure provides a method of preparing a crystalline Compound I Form I of the present disclosure, including forming a mixture of Compound I of the present disclosure, and a solvent, under conditions suitable to prepare Form I. In some embodiments, Compound I is dissolved in the solvent.

In some embodiments, the solvent can be ethyl acetate.

The method of preparing Compound I Form I can include a variety of other steps. In some embodiments, the reaction mixture can be heated to a temperature of about 85° C. In some embodiments, the method includes cooling the reaction mixture to a temperature of about 20° C.

In some embodiments, the method of preparing Compound I Form I also includes heating the mixture to dissolve Compound I, and cooling the mixture. In some embodiments, the method of preparing Compound I Form I includes forming a mixture of Compound I and ethyl acetate, heating the mixture to dissolve Compound I, and cooling the mixture, thus forming Compound I Form I.

Gentisic Acid

Crystalline Compound I Gentisic Acid can be prepared from Compound I Form I by dissolving Compound I Form I in a solvent with gentisic acid. In some embodiments, the present disclosure provides a method of preparing a crystalline Compound I Gentisic Acid, including forming a mixture of Compound I Form I, gentisic acid and a solvent, under conditions suitable to prepare Compound I Gentisic Acid. In some embodiments, Compound I Form I is dissolved in the solvent. In some embodiments, the solvent can be a polar aprotic solvent. In some embodiments, the solvent can be acetonitrile.

The method can include a variety of other steps. In some embodiments, the reaction mixture can be heated to a temperature of about 50° C. In some embodiments, the reaction mixture can be cooled to ambient temperature. In some embodiments, the reaction mixture can be cooled to a temperature of about 10° C. In some embodiments, the method can include multiple heating and cooling steps.

Hippuric Acid

Crystalline Compound I Hippuric Acid can be prepared from Compound I Form I by dissolving Compound I Form I in a solvent with hippuric acid. In some embodiments, the present disclosure provides a method of preparing a crystalline Compound I Hippuric Acid, including forming a mixture of Compound I Form I, hippuric acid and a solvent, under conditions suitable to prepare Compound I Hippuric Acid. In some embodiments, Compound I Form I is dissolved in the solvent. In some embodiments, the solvent can be a polar aprotic solvent. In some embodiments, the solvent can be acetone.

The method can include a variety of other steps. In some embodiments, the reaction mixture can be heated to a temperature of about 50° C. In some embodiments, the reaction mixture can be cooled to ambient temperature. In some embodiments, the reaction mixture can be cooled to a temperature of about 10° C. In some embodiments, the method can include multiple heating and cooling steps.

Phosphoric Acid Form I

Crystalline Compound I Phosphoric Acid Form I can be prepared from Compound I Form I by dissolving Compound I Form I in a solvent with phosphoric acid. In some embodiments, the present disclosure provides a method of preparing a crystalline Compound I Phosphoric Acid, including forming a mixture of Compound I Form I, phosphoric acid and a solvent, under conditions suitable to prepare Form I. In some embodiments, Compound I Form I is dissolved in the solvent. In some embodiments, the solvent can be a polar aprotic solvent. In some embodiments, the solvent can be acetone.

The method can include a variety of other steps. In some embodiments, the reaction mixture can be triturated with a solvent mixture of acetonitrile and isopropanol.

Phosphoric Acid Form II

Crystalline Compound I Phosphoric Acid Form II can be prepared from Compound I Form I by dissolving Compound I Form I in a solvent with phosphoric acid. In some embodiments, the present disclosure provides a method of preparing a crystalline Compound I Phosphoric Acid Form II, including forming a mixture of Compound I Form I, Phosphoric acid and a solvent, under conditions suitable to prepare Compound I Phosphoric Acid Form II. In some embodiments, Compound I Form I is dissolved in the solvent. In some embodiments, the solvent can be a polar protic solvent. In some embodiments, the solvent can be t-butanol, n-propanol, isopropanol, ethanol, or methanol. In some embodiments, the solvent can be isopropanol.

The method of preparing Compound I Phosphoric Acid Form II can include a variety of other steps. For example, the reaction mixture can be triturated with a solvent mixture of acetonitrile and isopropanol. The method can also include slurrying in diethyl ether and adding a seed of Compound I Phosphoric Acid Form I.

Succinic Acid

Crystalline Compound I Succinic Acid can be prepared from Compound I Form I by dissolving Compound I Form I in a solvent with succinic acid. In some embodiments, the present disclosure provides a method of preparing a crystalline Compound I Succinic Acid o, including forming a mixture of Compound I Form I, succinic acid and a solvent, under conditions suitable to prepare Compound I Succinic Acid. In some embodiments, Compound I Form I is dissolved in the solvent. In some embodiments, the solvent can be a polar protic solvent. In some embodiments, the solvent can be t-butanol, n-propanol, isopropanol, ethanol, or methanol. In some embodiments, the solvent can be isopropanol.

The method can include a variety of other steps. In some embodiments, the reaction mixture can be heated to a temperature of about 60° C. In some embodiments, the reaction mixture can be cooled to ambient temperature. In some embodiments, the reaction mixture can be cooled to a temperature of about 5° C. In some embodiments, the method can include multiple heating and cooling steps.

Ethanedisulfonic Acid Form I

Crystalline Compound I Ethanedisulfonic Acid Form I can be prepared from Compound I Form I by dissolving Compound I Form I in a solvent with ethanedisulfonic acid.

In some embodiments, the present disclosure provides a method of preparing a crystalline Compound I Ethanedisulfonic Acid, including forming a mixture of Compound I Form I, ethanedisulfonic acid and a solvent, under conditions suitable to prepare Compound I Ethanedisulfonic Acid Form I. In some embodiments, Compound I Form I is dissolved in the solvent. In some embodiments, the solvent can be a polar aprotic solvent. In some embodiments, the solvent can be acetone.

The method can include a variety of other steps. In some embodiments, the reaction mixture can be heated to a temperature of about 50° C. In some embodiments, the reaction mixture can be cooled to ambient temperature. In some embodiments, the reaction mixture can be cooled to a temperature of about 10° C. In some embodiments, the method can include multiple heating and cooling steps.

Ethanedisulfonic Acid Form II

Crystalline Compound I Ethanedisulfonic Acid Form II can be prepared by slurrying Compound I Ethanedisulfonic Acid Form I in a solvent. In some embodiments, the present disclosure provides a method of preparing a crystalline Compound I Ethanedisulfonic Acid Form II, including forming a mixture of Compound I Ethanedisulfonic Acid Form I, and a solvent, under conditions suitable to prepare Compound I Ethanedisulfonic Acid Form II. In some embodiments, the solvent can be dichloromethane.

Alternatively, crystalline Compound I Ethanedisulfonic Acid Form I can be prepared from Compound I Form I by dissolving Compound I Form I in a solvent with ethanedisulfonic acid. In some embodiments, the present disclosure provides a method of preparing a crystalline Compound I Ethanedisulfonic Acid Form II, including forming a mixture of Compound I Form I of the present disclosure, ethanedisulfonic acid and a solvent, under conditions suitable to prepare Compound I Ethanedisulfonic Acid Form II. In some embodiments, Compound I Ethanedisulfonic Acid Form II is dissolved in the solvent. In some embodiments, the solvent can be a polar aprotic solvent. In some embodiments, the solvent can be acetone.

The method can include a variety of other steps. In some embodiments, the reaction mixture can be heated to a temperature of about 60° C. In some embodiments, the reaction mixture can be cooled to a temperature of about 20° C.

V. Pharmaceutical Compositions

The solid forms of Compound I provided herein can be administered in the form of pharmaceutical compositions. This disclosure provides pharmaceutical compositions that contain, as the active ingredient, one or more of the solid forms of Compound I described or a pharmaceutically acceptable salt or ester thereof and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents (as indicated in the Combination Therapy section below). Such compositions are prepared in a manner well known in the pharmaceutical art (see, e.g., Remington's Pharmaceutical Sciences, Mace Publishing Co., Philadelphia, Pa. 17th Ed. (1985)); and Modern Pharmaceutics, Marcel Dekker, Inc. 3rd Ed. (G. S. Banker & C. T. Rhodes, Eds.).

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously orally, topically, as an inhalant or via an impregnated or coated device such as a stent, for example or an artery-inserted cylindrical polymer.

One mode for administration is parenteral, particularly by injection. The forms in which the novel compositions of the present disclosure may be incorporated for administration by injection include aqueous or oil suspensions or emulsions, with sesame oil, corn oil, cottonseed oil or peanut oil, as well as elixirs, mannitol, dextrose or a sterile aqueous solution and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the general methods of preparation are vacuum-drying and freeze-drying techniques which yield a powder of the active ingredient plus any additional desired ingredient from a previously sterile-filtered solution thereof.

Oral administration is another route for administration of compounds in accordance with the disclosure. Administration may be via capsule or enteric coated tablets or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup and methyl cellulose. The formulations can additionally include: lubricating agents such as talc, magnesium stearate and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile or on demand delivery of pharmaceutical agents.

In some embodiments, the compositions are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, each dosage unit contains from 1 mg to 2 g of a compound described herein and for parenteral administration, in some embodiments, from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Compositions for inhalation or insufflation include solutions and suspensions in pharmaceutically acceptable, aqueous or organic solvents or mixtures thereof and powders. The liquid or solid compositions may contain suitable pharmaceutically acceptable excipients as described supra. In some embodiments, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent or intermittent positive pressure breathing machine. Solution, suspension or powder compositions may be administered, in some embodiments orally or nasally, from devices that deliver the formulation in an appropriate manner.

In one embodiment, this disclosure relates to a pharmaceutical composition comprising a pharmaceutically acceptable excipient or carrier and a therapeutically effective amount of the compound of Compound I as described above or a pharmaceutically acceptable salt, ester, prodrug, stereoisomer or hydrate thereof.

VI. Methods of Use

The solid forms of Compound I described herein can be administered to a subject suffering from a viral infection such as, but not limited to, hepatitis B virus (HBV), hepatitis C virus (HCV), and human immuno-deficiency virus (HIV) in either single or multiple doses by any of the accepted modes of administration known to those who are skilled in the art and as detailed above.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" or a "partial antagonist" is a substance that provides a level of stimulation or inhibition, respectively, to its binding partner that is not fully or completely agonistic or antagonistic, respectively. It will be recognized that stimulation, and hence, inhibition is defined intrinsically for any substance or category of substances to be defined as agonists, antagonists, or partial agonists.

As used herein, "intrinsic activity" or "efficacy" relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. Where such contextually specific evaluations are relevant, and how they might be relevant in the context of the present disclosure, will be apparent to one of ordinary skill in the art.

As used herein, modulation of a receptor includes agonism, partial agonism, antagonism, partial antagonism, or inverse agonism of a receptor.

As will be appreciated by those skilled in the art, when treating a viral infection such as HCV, HBV, or HIV, such treatment may be characterized in a variety of ways and measured by a variety of endpoints. The scope of the present disclosure is intended to encompass all such characterizations.

In one embodiment, the method can be used to induce an immune response against multiple epitopes of a viral infection in a human. Induction of an immune response against viral infection can be assessed using any technique that is known by those of skill in the art for determining whether an immune response has occurred. Suitable methods of detecting an immune response for the present disclosure include, among others, detecting a decrease in viral load or antigen in a subject's serum, detection of IFN-gamma-secreting peptide specific T cells, and detection of elevated levels of one or more liver enzymes, such as alanine transferase (ALT) and aspartate transferase (AST). In one embodiment, the detection of IFN-gamma-secreting peptide specific T cells is accomplished using an ELISPOT assay. Another embodiment includes reducing the viral load associated with HBV infection, including a reduction as measured by PCR testing.

In some embodiments, the present disclosure provides a method of treating a viral infection, comprising administering to a human in need thereof, a therapeutically effective amount of a crystalline form of Compound I or pharmaceutical composition of the present disclosure. In some embodiments, the present disclosure provides a crystalline form of Compound I for use in the treatment of a viral infection, comprising administering a therapeutically effective amount of a crystalline form of Compound I or a pharmaceutical composition of the present disclosure. In some embodiments, the present disclosure provides use of a crystalline form of Compound I for the treatment of a viral infection. In some embodiments, the present disclosure provides use of a crystalline form of Compound I for the manufacture of a medicament for the treatment of a viral infection.

In another aspect, the present disclosure provides methods for treating a hepatitis B viral infection or a hepatitis C viral infection, wherein each of the methods includes the step of administering to a human subject infected with hepatitis B virus or hepatitis C virus a therapeutically effective amount of a crystalline form of Compound I. Typically, the human subject is suffering from a chronic hepatitis B infection or a chronic hepatitis C infection, although it is within the scope of the present disclosure to treat people who are acutely infected with HBV or HCV.

In some embodiments, the present disclosure provides a crystalline form of Compound I for use in the treatment of a hepatitis B viral infection or a hepatitis C viral infection. In some embodiments, the present disclosure provides use of a crystalline form of Compound I for the manufacture of a medicament for the treatment of a hepatitis B viral infection or a hepatitis C viral infection.

In some embodiments, the present disclosure provides a crystalline form of Compound I for use in the treatment of a hepatitis B viral infection. In some embodiments, the present disclosure provides use of a crystalline form of Compound I for the manufacture of a medicament for the treatment of a hepatitis B viral infection.

Treatment in accordance with the present disclosure typically results in the stimulation of an immune response against HBV or HCV in a human being infected with HBV or HCV, respectively, and a consequent reduction in the viral load of HBV or HCV in the infected person. Examples of immune responses include production of antibodies (e.g., IgG antibodies) and/or production of cytokines, such as interferons, that modulate the activity of the immune system. The immune system response can be a newly induced response, or can be boosting of an existing immune response. In particular, the immune system response can be seroconversion against one or more HBV or HCV antigens.

The viral load can be determined by measuring the amount of HBV DNA or HCV DNA present in the blood. For example, blood serum HBV DNA can be quantified using the Roche COBAS Amplicor Monitor PCR assay (version 2.0; lower limit of quantification, 300 copies/mL [57 IU/mL]) and the Quantiplex bDNA assay (lower limit of quantification, 0.7 MEq/mL; Bayer Diagnostics, formerly Chiron Diagnostics, Emeryville, Calif.). The amount of antibodies against specific HBV or HCV antigens (e.g., hepatitis B surface antigen (HBsAG)) can be measured using such art-recognized techniques as enzyme-linked immunoassays and enzyme-linked immunoabsorbent assays. For example, the amount of antibodies against specific HBV or HCV antigens can be measured using the Abbott AxSYM microparticle enzyme immunoassay system (Abbott Laboratories, North Chicago, Ill.).

Compound I can be administered by any useful route and means, such as by oral or parenteral (e.g., intravenous) administration. Therapeutically effective amounts of Compound I are from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 g to about 30 mg per day, or such as from about 30 g to about 300 µg per day.

Therapeutically effective amounts of Compound I are also from about 0.01 mg per dose to about 1000 mg per dose, such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose.

Other therapeutically effective amounts of Compound I are about 1 mg per dose, 1.5 mg per dose, 2 mg per dose, 2.5 mg per dose, 3 mg per dose, or 3.5 mg per dose or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of Compound I are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. A single dose can also be administered once every month.

The frequency of dosage of Compound I will be determined by the needs of the individual patient and can be, for example, once per day or twice, or more times, per day.

Administration of Compound I continues for as long as necessary to treat the HBV or HCV infection. For example, Compound I can be administered to a human being infected with HBV or HCV for a period of from 20 days to 180 days or, for example, for a period of from 20 days to 90 days or, for example, for a period of from 30 days to 60 days.

Administration can be intermittent, with a period of several or more days during which a patient receives a daily dose of Compound I, followed by a period of several or more days during which a patient does not receive a daily dose of Compound I. For example, a patient can receive a dose of Compound I every other day, or three times per week. Again by way of example, a patient can receive a dose of Compound I each day for a period of from 1 to 14 days, followed by a period of 7 to 21 days during which the patient does not receive a dose of Compound I, followed by a subsequent period (e.g., from 1 to 14 days) during which the patient again receives a daily dose of Compound I. Alternating periods of administration of Compound I, followed by non-administration of Compound I, can be repeated as clinically required to treat the patient.

As described more fully herein, crystalline forms of Compound I can be administered with one or more additional therapeutic agent(s) to a human being infected with hepatitis B virus or hepatitis C virus. The additional therapeutic agent(s) can be administered to the infected human being at the same time as the crystalline form of Compound I, or before or after administration of the crystalline form of Compound I. In some embodiments, the present disclosure provides a crystalline form of Compound I, for use in a method of treating or preventing a hepatitis B viral infection, wherein the crystalline form of Compound I is administered simultaneously, separately or sequentially with one or more additional therapeutic agents for treating a hepatitis B viral infection. In some embodiments, the present disclosure provides use of a crystalline form of Compound I for the manufacture of a medicament for the treatment of a hepatitis B viral infection, wherein the crystalline form of Compound I is administered simultaneously, separately or sequentially with one or more additional therapeutic agents for treating a hepatitis B viral infection.

In another aspect, the present disclosure provides a method for ameliorating a symptom associated with an HBV infection or HCV infection, wherein the method comprises administering to a human subject infected with hepatitis B virus or hepatitis C virus a therapeutically effective amount of the crystalline form of Compound I, wherein the therapeutically effective amount is sufficient to ameliorate a symptom associated with the HBV infection or HCV infection. Such symptoms include the presence of HBV virus particles (or HCV virus particles) in the blood, liver inflammation, jaundice, muscle aches, weakness and tiredness.

In some embodiments, the present disclosure provides a crystalline form of Compound I for use in ameliorating a symptom associated with an HBV infection or HCV infection, wherein the method comprises administering to a human subject infected with hepatitis B virus or hepatitis C virus a therapeutically effective amount of the crystalline form of Compound I, wherein the therapeutically effective amount is sufficient to ameliorate a symptom associated with the HBV infection or HCV infection. In some embodiments, the present disclosure provides use of a crystalline form of Compound I for the manufacture of a medicament for the ameliorating a symptom associated with an HBV infection or HCV infection, wherein the method comprises administering to a human subject infected with hepatitis B virus or hepatitis C virus a therapeutically effective amount of the crystalline form of Compound I, wherein the therapeutically effective amount is sufficient to ameliorate a symptom associated with the HBV infection or HCV infection.

In a further aspect, the present disclosure provides a method for reducing the rate of progression of a hepatitis B viral infection, or a hepatitis C virus infection, in a human being, wherein the method comprises administering to a human subject infected with hepatitis B virus or hepatitis C virus a therapeutically effective amount of Compound I, or a pharmaceutically acceptable salt thereof, wherein the therapeutically effective amount is sufficient to reduce the rate of progression of the hepatitis B viral infection or hepatitis C viral infection. The rate of progression of the infection can be followed by measuring the amount of HBV virus particles or HCV virus particles in the blood.

In another aspect, the present disclosure provides a method for reducing the viral load associated with HBV infection or HCV infection, wherein the method comprises administering to a human being infected with HBV or HCV a therapeutically effective amount of Compound I, or a pharmaceutically acceptable salt thereof, wherein the therapeutically effective amount is sufficient to reduce the HBV viral load or the HCV viral load in the human being.

In a further aspect, the present disclosure provides a method of inducing or boosting an immune response against Hepatitis B virus or Hepatitis C virus in a human being, wherein the method comprises administering a therapeutically effective amount of Compound I, or a pharmaceutically acceptable salt thereof, to the human being, wherein a new immune response against Hepatitis B virus or Hepatitis C virus is induced in the human being, or a preexisting immune response against Hepatitis B virus or Hepatitis C virus is boosted in the human being. Seroconversion with respect to HBV or HCV can be induced in the human being. Examples of immune responses include production of antibodies, such as IgG antibody molecules, and/or production of cytokine molecules that modulate the activity of one or more components of the human immune system.

Induction of seroconversion against HCV or HBV in patients chronically infected with either of these viruses is an unexpected property of Compound I. In clinical practice, an HBV patient, or HCV patient, is treated with Compound I, alone or in combination with one or more other therapeutic agents, until an immune response against HBV or HCV is induced or enhanced and the viral load of HBV or HCV is reduced. Thereafter, although the HBV or HCV virus may persist in a latent form in the patient's body, treatment with Compound I can be stopped, and the patient's own immune system is capable of suppressing further viral replication. In patients treated in accordance with the present disclosure and who are already receiving treatment with an antiviral agent that suppresses replication of the HBV virus or HCV virus, there may be little or no detectable viral particles in the body of the patient during treatment with the antiviral agent(s). In these patients, seroconversion will be evident when the antiviral agent(s) is no longer administered to the patient and there is no increase in the viral load of HBV or HCV.

In the practice of the present disclosure, an immune response is induced against one or more antigens of HBV or HCV. For example, an immune response can be induced against the HBV surface antigen (HBsAg), or against the small form of the HBV surface antigen (small S antigen), or against the medium form of the HBV surface antigen (medium S antigen), or against a combination thereof. Again by way of example, an immune response can be induced against the HBV surface antigen (HBsAg) and also against other HBV-derived antigens, such as the core polymerase or x-protein.

Induction of an immune response against HCV or HBV can be assessed using any technique that is known by those of skill in the art for determining whether an immune response has occurred. Suitable methods of detecting an immune response for the present disclosure include, among others, detecting a decrease in viral load in a subject's serum, such as by measuring the amount of HBV DNA or HCV DNA in a subject's blood using a PCR assay, and/or by measuring the amount of anti-HBV antibodies, or anti-HCV antibodies, in the subject's blood using a method such as an ELISA.

Additionally, the compounds of this disclosure may be useful in the treatment of cancer or tumors (including dysplasias, such as uterine dysplasia). These includes hematological malignancies, oral carcinomas (for example of the lip, tongue or pharynx), digestive organs (for example esophagus, stomach, small intestine, colon, large intestine, or rectum), liver and biliary passages, pancreas, respiratory system such as larynx or lung (small cell and non-small cell), bone, connective tissue, skin (e.g., melanoma), breast, reproductive organs (uterus, cervix, testicles, ovary, or prostate), urinary tract (e.g., bladder or kidney), brain and endocrine glands such as the thyroid. In summary, the compounds of this disclosure are employed to treat any neoplasm, including not only hematologic malignancies but also solid tumors of all kinds.

Hematological malignancies are broadly defined as proliferative disorders of blood cells and/or their progenitors, in which these cells proliferate in an uncontrolled manner. Anatomically, the hematologic malignancies are divided into two primary groups: lymphomas—malignant masses of lymphoid cells, primarily but not exclusively in lymph nodes, and leukemias—neoplasm derived typically from lymphoid or myeloid cells and primarily affecting the bone marrow and peripheral blood. The lymphomas can be subdivided into Hodgkin's Disease and Non-Hodgkin's lymphoma (NHL). The latter group comprises several distinct entities, which can be distinguished clinically (e.g. aggressive lymphoma, indolent lymphoma), histologically (e.g. follicular lymphoma, mantle cell lymphoma) or based on the origin of the malignant cell (e.g. B lymphocyte, T lymphocyte). Leukemias and related malignancies include acute myelogenous leukemia (AML), chronic myelogenous leukemia (CML), acute lymphoblastic leukemia (ALL) and chronic lymphocytic leukemia (CLL). Other hematological malignancies include the plasma cell dyscrasias including multiple myeloma, and the myelodysplastic syndromes.

VII. COMBINATION THERAPY

In certain embodiments, a method for treating or preventing an infectious disease, a viral infection, hepatitis B infection, HIV infection, cancer, or a hyperproliferative disease in a human having or at risk of having the disease is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents. In one embodiment, a method for treating an infectious disease, a viral infection, hepatitis B infection, HIV infection, cancer, or a hyperproliferative disease in a human having or at risk of having the disease is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In certain embodiments, the present disclosure provides a method for treating a viral infection, comprising administering to a subject in need thereof a therapeutically effective amount of a compound disclosed herein or a pharmaceutically acceptable salt thereof, in combination with a therapeutically effective amount of one or more (e.g., one, two, three, four, one or two, one to three, or one to four) additional therapeutic agents which are suitable for treating the viral infection. In some embodiments, the viral infection is a hepatitis B infection. In some embodiments, the viral infection is a HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of Combination Therapy

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the subject. When administered sequentially, the combination may be administered in two or more administrations.

Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

In certain embodiments, a compound as disclosed herein may be combined with one or more (e.g., one, two, three, four, one or two, one to three, or one to four) additional therapeutic agents in any dosage amount of the compound (e.g., from 10 mg to 1000 mg of compound).

Co-administration includes administration of unit dosages of the compounds disclosed herein before or after administration of unit dosages of one or more additional therapeutic agents. The compound disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a subject, for example as a solid dosage form for oral administration.

In certain embodiments a compound as described herein is formulated as a tablet, which may optionally contain one or more other compounds useful for treating the disease being treated. In certain embodiments, the tablet can contain another active ingredient for treating a viral disease, e.g., hepatitis B virus or HIV.

In certain embodiments, such tablets are suitable for once daily dosing.

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent, or excipient are provided.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

Viral Combination Therapy

The compounds described herein may be used or combined with one or more of an antiviral agents including abacavir, aciclovir, adefovir, amantadine, amprenavir, arbidol, atazanavir, atripla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, immunovir, idoxuridine, imiquimod, indinavir, inosine, integrase inhibitors, interferons, including interferon type III, interferon type II, interferon type I, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof.

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide. A compound as disclosed herein may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt thereof, is combined with 150 mg tenofovir disoproxil fumarate, tenofovir disoproxil hemifumarate, or tenofovir disoproxil. A compound as disclosed may be combined with the agents provided herein in any dosage amount of the compound (e.g., from 50 mg to 500 mg of compound) the same as if each combination of dosages were specifically and individually listed.

HIV Combination Therapy

In certain embodiments, a method for treating or preventing an HIV infection in a human or animal having or at risk of having the infection is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human or animal having or at risk of having the infection is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating an HIV infection, comprising administering to a subject in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, the compounds disclosed herein are formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

In the above embodiments, the additional therapeutic agent may be an anti-HIV agent. In some embodiments, the additional therapeutic agent is selected from the group consisting of HIV combination drugs, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T), latency reversing agents, compounds that target the HIV capsid (including capsid inhibitors), immune-based therapies, phosphatidylinositol 3-kinase (PI3K) inhibitors, alpha-4/beta-7 antagonists, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and other HIV therapeutic agents, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir, emtricitabine, tenofovir alafenamide); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; Vacc-4x and romidepsin; and APH-0812.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, ACC-007, AIC-292, KM-023, PC-1005, and VM-1500.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX© and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, MK-8504 and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include ceniviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068.

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), AM-0015, ALT-803, NIZ-985, NKTR-255, IL-15 modulating antibodies, JQ1, disulfiram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series;

Immune-Based Therapies

Examples of immune-based therapies include toll-like receptors modulators such as TLR1, TLR2, TLR3, TLR4, TLR5, TLR6, TLR7, TLR8, TLR9, TLR10, TLR11, TLR12, and TLR13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, STING modulators, RIG-I modulators, NOD2 modulators, and IR-103.

Examples of TLR8 modulators include motolimod, resiquimod, 3M-051, 3M-052, MCT-465, IMO-4200, VTX-763, VTX-1463 and those disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 9,670, 205 (Gilead Sciences Inc.), US20160289229 (Gilead Sciences Inc.), U.S. patent application Ser. No. 15/692,161 (Gilead Sciences Inc.), and U.S. patent application Ser. No. 15/692,093 (Gilead Sciences Inc.).

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, and MB-66.

Examples of those targeting HIV in such a manner include bavituximab, UB-421, C2F5, 2G12, C4E10, C2F5+C2G12+ C4E10, 8ANC195, 3BNC117, 3BNC60, 10-1074, PGT145, PGT121, PGT-151, PGT-133, MDX010 (ipilimumab), DH511, N6, VRC01 PGDM1400, A32, 7B2, 10E8, 10E8v4, CAP256-VRC26.25, DRVIA7, VRC-07-523, VRC-HIVMAB080-00-AB, VRC-HIVMAB060-00-AB, MGD-014 and VRC07. Example of HIV bispecific antibodies include MGD014.

Pharmacokinetic Enhancers

Examples of pharmacokinetic enhancers include cobicistat and ritonavir.

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/ AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC—HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICH-vac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI and MVA.HTI.

Additional HIV Therapeutic Agents

Examples of additional HIV therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

Examples of other drugs for treating HIV include acemannan, alisporivir, BanLec, deferiprone, Gamimune, metenkefalin, naltrexone, Prolastin, REP 9, RPI-MN, VSSP, H1viral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

Gene Therapy and Cell Therapy

Gene Therapy and Cell Therapy include the genetic modification to silence a gene; genetic approaches to directly kill the infected cells; the infusion of immune cells designed to replace most of the subject's own immune system to enhance the immune response to infected cells, or activate the subject's own immune system to kill infected cells, or find and kill the infected cells; genetic approaches to modify cellular activity to further alter endogenous immune responsiveness against the infection.

Examples of dendritic cell therapy include AGS-004.

Gene Editors

Examples of gene editing systems include a CRISPR/Cas9 system, a zinc finger nuclease system, a TALEN system, a homing endonucleases system, and a meganuclease system.

Examples of HIV targeting CRISPR/Cas9 systems include EBT101.

CAR-T Cell Therapy

CAR-T cell therapy includes a population of immune effector cells engineered to express a chimeric antigen receptor (CAR), wherein the CAR comprises an HIV antigen-binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T cell or an NK cell. In some embodiments, the T cell is a CD4+ T cell, a CD8+ T cell, or a combination thereof.

Examples of HIV CAR-T include VC-CAR-T.

TCR-T Cell Therapy

TCR-T cell therapy includes T cells engineered to target HIV derived peptides present on the surface of virus-infected cells.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir, emtricitabine, tenofovir alafenamide); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, tenofovir alafenamide hemifumarate, or bictegravir.

In a particular embodiment, a compound disclosed herein, or a pharmaceutically acceptable salt thereof, is combined with tenofovir, tenofovir disoproxil, tenofovir disoproxil fumarate, tenofovir alafenamide, tenofovir alafenamide hemifumarate, or bictegravir.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, tenofovir alafenamide hemifumarate, and bictegravir and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, tenofovir alafenamide hemifumarate, and bictegravir and a second additional therapeutic agent, wherein the second additional therapeutic agent is emtricitabine.

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein may be combined with the agents provided herein in any dosage amount of the compound (e.g., from 1 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine.

A compound as disclosed herein may be combined with the agents provided herein in any dosage amount of the compound (e.g., from 1 mg to 500 mg of compound) the same as if each combination of dosages were specifically and individually listed.

HBV Combination Therapy

In certain embodiments, a method for treating or preventing an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of a compound disclosed herein or a pharmaceutically acceptable salt thereof, in combination with a therapeutically effective amount of one or more (e.g., one, two, three, four, one or two, one to three, or one to four) additional therapeutic agents which are suitable for treating an HBV infection.

The compounds described herein may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, synthetic nucleases, TALENs), cell therapies such as CAR-T (chimeric antigen receptor T-cell), and TCR-T (an engineered T cell receptor) agent or any combination thereof.

In certain embodiments, a compound described herein is formulated as a tablet, which may optionally contain one or more other compounds useful for treating HBV. In certain embodiments, the tablet can contain another active ingredient for treating HBV, such as 3-dioxygenase (IDO) inhibitors, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, and combinations thereof.

HBV Combination Drugs

Examples of combination drugs for the treatment of HBV include TRUVADA® (tenofovir disoproxil fumarate and emtricitabine); ABX-203, lamivudine, and PEG-IFN-alpha; ABX-203 adefovir, and PEG-IFNalpha; and INO-1800 (INO-9112 and RG7944).

Other HBV Drugs

Examples of other drugs for the treatment of HBV include alpha-hydroxytropolones, amdoxovir, beta-hydroxycytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP—IPV-Hep B, HBAI-20, Infanrix-DTaP—IPV-Hep B-Hib, Pentabio Vaksin DTP—HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPER-VAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440,WF-10, AB-452, ribavirin, IL-12, INO-9112, polymer polyethyleneimine (PEI), Gepon, VGV-1, MOR-22, CRV-431, JNJ-0535, TG-1050, ABI-H2158, BMS-936559, RO-7011785, RG-7854, AB-506,RO-6871765, AIC-649, and IR-103.

Toll-Like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475, and ND-1.1.

Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, D, telratolimod, SP-0509, TMX-30X, TMX-202, RG-7863, RG-7795, LHC-165, RG-7854, and the compounds disclosed in US20100143301 (Gilead Sciences), US20110098248 (Gilead Sciences), and US20090047249 (Gilead Sciences).

Examples of TLR8 modulators include motolimod, resiquimod, 3M-051, 3M-052, MCT-465, IMO-4200, VTX-763, VTX-1463, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), US20130251673 (Novira Therapeutics), U.S. Pat. No. 9,670,205, US20160289229 U.S. patent application Ser. No. 15/692,161 and U.S. patent application Ser. No. 15/692,093.

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Examples of TLR7, TLR8 and TLR9 modulators include the compounds disclosed in WO2017047769 (Teika Seiyaku), WO2015014815 (Janssen), WO2018045150 (Gilead Sciences Inc), WO2018045144 (Gilead Sciences Inc), W2015162075 (Roche),WO2017034986 (University of Kansas), WO2018095426 (Jiangsu Hengrui Medicine Co Ltd), WO2016091698 (Roche), WO2016075661 (GaxoSmithKline Biologicals),WO2016180743 (Roche), WO2018089695 (Dynavax Technologies),WO2016055553 (Roche), WO2015168279 (Novartis), WO2016107536 (Medshine Discovery), WO2018086593 (Livo (Shanghai) Pharmaceutical),WO2017106607 (Merck),WO2017061532 (Sumitomo Dainippon Pharma), WO2016023511 (Chia Tai Tianqing Pharmaceutical), WO2017076346 (Chia Tai Tianqing Pharmaceutical), WO2017046112 (Roche), WO2018078149 (Roche),WO2017040233 (3M Co), WO2016141092 (Gilead Sciences), WO2018049089 (Bristol Myers Squibb),WO2015057655 (Eisai Co Ltd), WO2017001307 (Roche), WO2018005586 (Bristol Myers Squibb), WO201704023 (3M Co),WO2017163264 (Council of Scientific and Industrial Research (India)), WO2018046460 (GlaxoSmithKline Biologicals), WO2018047081 (Novartis), WO2016142250 (Roche), WO2015168269 (Novartis),WO201804163 (Roche), WO2018038877 (3M Co), WO2015057659 (Eisai Co Ltd), WO2017202704 (Roche), WO2018026620 (Bristol Myers Squibb),WO2016029077 (Janus Biotherapeutics), WO201803143 (Merck), WO2016096778 (Roche), WO2017190669 (Shanghai De Novo Pharmatech),U.S. Ser. No. 09/884,866 (University of Minnesota),WO2017219931 (Sichuan KelunBiotech Biopharmaceutical), WO2018002319 (Janssen Sciences), WO2017216054 (Roche),WO2017202703 (Roche),WO2017184735 (IFM Therapeutics), WO2017184746 (IFM Therapeutics), WO2015088045 (Takeda Pharmaceutical), WO2017038909 (Takeda Pharmaceutical),WO2015095780 (University of Kansas),WO2015023958 (University of Kansas).

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfan1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin interferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-GSK6-LRx, GSK-3389404, RG-6004.

Short Interfering RNAs (siRNA) and ddRNAi.

Examples of siRNA include TKM-HBV (TKM-HepB), ALN—HBV, SR-008, HepB-nRNA, and ARC-520, ARC-521, ARB-1740, ARB-1467.

Examples of DNA-directed RNA interference (ddRNAi) include BB-HB-331.

Endonuclease Modulators

Examples of endonuclease modulators include PGN-514.

Ribonucleotide Reductase Inhibitors

Examples of inhibitors of ribonucleotide reductase include Trimidox.

HBV E Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X receptor agonist

Examples of farnesoid x receptor agonist such as EYP-001, GS-9674, EDP-305, MET-409, Tropifexor, AKN-083, RDX-023, BWD-100, LMB-763, INV-3, NTX-023-1, EP-024297 and GS-8670.

HBV Antibodies

Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed).

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Fully human monoclonal antibodies include HBC-34.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience).

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors.

Examples of nucleoprotein modulators include GS-4882, AB-423, AT-130, GLS4, NVR-1221, NVR-3778, AL-3778, BAY 41-4109, morphothiadine mesilate, ARB-168786, ARB-880, JNJ-379, RG-7907, HEC-72702, AB-506, ABI-H0731, JNJ-440, ABI-H2158 and DVR-23.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), US 20170334882 (Novira), US 20170334898 (Roche), WO2017202798 (Roche), WO2017214395 (Enanta), WO2018001944 (Roche), WO2018001952 (Roche), W2018005881 (Novira), W2018005883 (Novira), WO2018011100 (Roche), WO2018011160 (Roche), WO2018011162 (Roche), WO2018011163 (Roche), W2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira).

Examples of transcript inhibitors include the compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), W2017211791 (Roche), W2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

Retinoic Acid-inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include SB-9200.

Phosphatidylinositol 3-kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Indoleamine-2, 3-dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

PD-1 Inhibitors

Examples of PD-1 inhibitors include cemiplimab, nivolumab, pembrolizumab, pidilizumab, BGB-108, STI-A1014, SHR-1210, PDR-001, PF-06801591, IBI-308, GB-226, STI-1110, JNJ-63723283, CA-170, durvalumab, atezolizumab and mDX-400, JS-001, Camrelizumab, Sintilimab, Sintilimab, tislelizumab, BCD-100, BGB-A333 JNJ-63723283, GLS-010 (WBP-3055), CX-072, AGEN-2034, GNS-1480 (Epidermal growth factor receptor antagonist; Programmed cell death ligand 1 inhibitor), CS-1001, M-7824 (PD-L1/TGF-0 bifunctional fusion protein), Genolimzumab, BMS-936559.

PD-L1 Inhibitors

Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014,GS-4224, CX-072, and BMS-936559.

Examples of PD-1 inhibitors include the compounds disclosed in WO2017112730 (Incyte Corp), WO2017087777 (Incyte Corp), WO2017017624, WO2014151634 (Bristol Myers Squibb Co), WO201317322 (Bristol Myers Squibb Co), WO2018119286 (Incyte Corp), WO2018119266 (Incyte Corp), WO2018119263 (Incyte Corp), WO2018119236 (Incyte Corp), WO2018119221 (Incyte Corp), WO2018118848 (Bristol Myers Squibb Co), WO20161266460 (Bristol Myers Squibb Co), WO2017087678 (Bristol Myers Squibb Co), WO2016149351 (Bristol Myers Squibb Co), WO2015033299 (Aurigene Discovery Technologies Ltd), WO2015179615 (Eisai Co Ltd; Eisai Research Institute), WO2017066227 (Bristol Myers Squibb Co), WO2016142886 (Aurigene Discovery Technologies Ltd), WO2016142852 (Aurigene Discovery Technologies Ltd), WO2016142835 (Aurigene Discovery Technologies Ltd; Individual), WO2016142833 (Aurigene Discovery Technologies Ltd), WO2018085750 (Bristol Myers Squibb Co), WO2015033303 (Aurigene Discovery Technologies Ltd), WO2017205464 (Incyte Corp), WO2016019232 (3M Co; Individual; Texas A&M University System), WO2015160641 (Bristol Myers Squibb Co), WO2017079669 (Incyte Corp), WO2015033301 (Aurigene Discovery Technologies Ltd), WO2015034820 (Bristol Myers Squibb Co), WO2018073754 (Aurigene Discovery Technologies Ltd), WO2016077518 (Bristol Myers Squibb Co), WO2016057624 (Bristol Myers Squibb Co), WO2018044783 (Incyte Corp), WO2016100608 (Bristol Myers Squibb Co), WO2016100285 (Bristol Myers Squibb Co), WO2016039749 (Bristol Myers Squibb Co), WO2015019284 (Cambridge Enterprise Ltd), WO2016142894 (Aurigene Discovery Technologies Ltd), WO2015134605 (Bristol Myers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (Bristol Myers Squibb Co), WO2013144704 (Aurigene Discovery Technologies Ltd), WO2018013789 (Incyte Corp), WO2017176608 (Bristol Myers Squibb Co), WO2018009505 (Bristol Myers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd),WO2015044900 (Aurigene Discovery Technologies Ltd), WO2018026971 (Arising International).

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds disclosed in U.S. Pat. No. 9,186,337B2 (Oryzon Genomics), GSK-2879552, and RG-6016.

STING Agonists

Examples of STING agonists include SB-11285, AdVCA0848, STINGVAX, and the compounds disclosed in WO 2018065360 ("Biolog Life Science Institute Forschungslabor und Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkline), WO 2017075477 (Aduro Biotech), US 20170044206 (Merck), WO 2014179760 (University of California), WO2018098203 (Janssen), WO2018118665 (Merck), WO2018118664 (Merck), WO2018100558 (Takeda), WO2018067423 (Merck), WO2018060323 (Boehringer).

Non-Nucleoside Reverse Transcriptase Inhibitors (NNRTI)

Examples of NNRTI include the compounds disclosed in WO2018118826 (Merck), WO2018080903 (Merck), WO2018119013 (Merck), WO2017100108 (Idenix), WO2017027434 (Merck), WO2017007701 (Merck), WO2008005555 (Gilead).

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

Gene Therapy and Cell Therapy

Gene therapy and cell therapy includes the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and genetic approaches to modify cellular activity to further alter endogenous immune responsiveness against the infection.

Gene Editors

Examples of genome editing systems include a CRISPR/Cas9 system, a zinc finger nuclease system, a TALEN system, a homing endonucleases system, and a meganuclease system; e.g., cccDNA elimination via targeted cleavage, and altering one or more of the hepatitis B virus (HBV) viral genes. Altering (e.g., knocking out and/or knocking down) the PreC, C, X PreSI, PreS2, S, P or SP gene refers to (1) reducing or eliminating PreC, C, X PreSI, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreSI, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X PreSI, PreS2, S, P and/or SP gene(s) is performed by targeting the gene(s) within HBV cccDNA and/or integrated HBV DNA.

CAR-T Cell Therapy

CAR T cell therapy includes a population of immune effector cells engineered to express a chimeric antigen receptor (CAR), wherein the CAR comprises an HBV antigen-binding domain. The immune effector cell is a T cell or an NK cell. In some embodiments, the T cell is a CD4+ T cell, a CD8+ T cell, or a combination thereof. Cells can be autologous or allogeneic.

TCR-T Cell Therapy

TCR T cell therapy includes T cells expressing HBV-specific T cell receptors. TCR-T cells are engineered to target HBV derived peptides presented on the surface of virus-infected cells. In some embodiments, the T-cells express HBV surface antigen (HBsAg)-specific TCR. Examples of TCR-T therapy directed to treatment of HBV include LTCR-H2-1.

In another specific embodiment, a compound disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound disclosed herein, or a pharmaceutically acceptable salt thereof, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, a compound disclosed herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In a particular embodiment, a compound disclosed herein, or a pharmaceutically acceptable salt thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

Cancer Combination Therapy

In one embodiment, the compound of the disclosure may be employed with other therapeutic methods of cancer treatment. Preferably, combination therapy with chemotherapeutic, hormonal, antibody, surgical and/or radiation treatments are contemplated.

In some embodiments, the further anti-cancer therapy is surgery and/or radiotherapy.

In some embodiments, the further anti-cancer therapy is at least one additional cancer medicament.

In some embodiments, there is provided a combination comprising a compound as described herein, or a pharmaceutically acceptable salt thereof and at least one further cancer medicament.

In some embodiments, there is provided a combination comprising a compound as described herein, or a pharmaceutically acceptable salt thereof and at least one further cancer medicament, for use in therapy.

In some embodiments, there is provided the use of a combination comprising a compound as described herein, or a pharmaceutically acceptable salt thereof and at least one cancer medicament, in the manufacture of a medicament for the treatment of cancer.

Examples of further cancer medicaments include intercalating substances such as anthracycline, doxorubicin, idarubicin, epirubicin, and daunorubicin; topoisomerase inhibitors such as irinotecan, topotecan, camptothecin, lamellarin D, etoposide, teniposide, mitoxantrone, amsacrine, ellipticines and aurintricarboxylic acid; nitrosourea compounds such as carmustine (BCNU), lomustine (CCNU), and streptozocin; nitrogen mustards such as cyclophosphamide, mechlorethamine, uramustine, bendamustine, melphalan, chlorambucil, mafosfamide, trofosfamid and ifosfamide; alkyl sulfonates such as busulfan and treosulfan; alkylating agents such as procarbazin, dacarbazin, temozolomid and thiotepa; platinum analogues such as cisplatin, carboplatin, nedaplatin, oxaliplatin, satraplatin, and triplatin tetranitrate; microtubule disruptive drugs such as vinblastine, colcemid and nocodazole; antifolates like methotrexate, aminopterin, dichloromethotrexat, pemetrexed, raltitrexed and pralatrexate: purine analogues like azathioprine, mercaptopurine, thioguanine, fludarabine, fludarabine phosphate, pentostatin and cladribine; pyrimidine analogues like 5-fluorouracil, floxuridine, cytarabine, 6-azauracil, gemcitabine; steroids such as gestagene, androgene, glucocorticoids, dexamethasone, prednisolone, and prednisone; anti-cancer antibodies such as monoclonal antibodies, e.g., alemtuzumab, apolizumab, cetuximab, epratuzumab, galiximab, gemtuzumab, ipilimumab, labetuzumab, panitumumab, rituximab, trastuzumab, nimotuzumab, mapatumumab, matuzumab, rhMab ICR62 and pertuzumab, radioactively labeled antibodies and antibody-drug conjugates; anti-cancer peptides such as radioactively labeled peptides and peptide-drug conjugates; and taxane and taxane analogues such as paclitaxel and docetaxel.

In certain embodiments, a method for treating or preventing a hyperproliferative disorder or cancer in a human or animal having or at risk of having the hyperproliferative disorder or cancer is provided, comprising administering to the human or animal a therapeutically effective amount of a compound as disclosed herein, or a pharmaceutically acceptable salt thereof, in combination with a therapeutically effective amount of one or more (e.g., one, two, three, one or two, or one to three) additional therapeutic agents. In one embodiment, a method for treating a hyperproliferative disorder or cancer in a human or animal having or at risk of having the hyperproliferative disorder or cancer is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating a hyperproliferative disorder or cancer, comprising administering to a subject in need thereof a therapeutically effective amount of a compound disclosed herein, or a pharmaceutically acceptable salt thereof, in combination with a therapeutically effective amount of one or more additional therapeutic agents which are suitable for treating hyperproliferative disorder or cancer.

The compounds described herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, a gene modifier or editor (such as CRISPR/Cas9, zinc finger nucleases or synthetic nucleases, TALENs), a CAR (chimeric antigen receptor) T-cell immunotherapeutic agent, an engineered T cell receptor (TCR-T), or any combination thereof. These therapeutic agents may be in the forms of compounds, antibodies, polypeptides, or polynucleotides. In one embodiment, provided herein is a product comprising a compound described herein and an additional therapeutic agent as a combined preparation for simultaneous, separate, or sequential use in therapy.

The one or more therapeutic agents include, but are not limited to, an inhibitor, agonist, antagonist, ligand, modulator, stimulator, blocker, activator or suppressor of a gene, ligand, receptor, protein, or factor. Non-limiting examples of additional therapeutic agents include: Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2B, A2a, A3), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1,CHK2), chemokine (C-C motif) receptor (such as CCR2, CCR4, CCR5), chemokine (C—X-C motif) receptor (such as CXCR4, CXCR1 and CXCR2), Chemokine CC21 ligand, Cholecystokinin CCK2 receptor, Chorionic gonadotropin, c-Kit (tyrosine-protein kinase Kit or CD117), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COP9 signalosome subunit 5, CSF-1 (colony-stimulating factor 1 receptor), CSF2 gene, CTLA-4 (cytotoxic T-lymphocyte protein 4) receptor, Cyclin D1, Cyclin G, cyclin-dependent kinases (CDK, such as CDK1, CDK1B, CDK2-9), cyclooxygenase (such as 1, 2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, Delta-like protein ligand (such as 3, 4), Deoxyribonuclease, Dickkopf-1 ligand, dihydrofolate reductase (DHFR), Dihydropyrimidine dehydrogenase, Dipeptidyl peptidase IV, discoidin domain receptor (DDR, such as DDR1), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, echinoderm microtubule like protein 4, EGFR tyrosine kinase receptor, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Factor (such as Xa, VIIa), famesoid x receptor (FXR), Fas ligand, Fatty acid synthase (FASN), Ferritin, FGF-2 ligand, FGF-5 ligand, fibroblast growth factor (FGF, such as FGF1, FGF2, FGF4), Fibronectin, Fms-related tyrosine kinase 3 (Flt3), focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releasing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone H3, HLA class I antigen (A-2 alpha), HLA class II antigen, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha (HIFlu), Imprinted Maternally Expressed Transcript (H19) gene, mitogen-activated protein kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, GI, G2, K, M), Immunoglobulin Fc receptor, Immunoglobulin gamma Fc receptor (such as I, III, IIIA), indoleamine 2,3-dioxygenase (IDO, such as IDO1), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), lysyl oxidase-like protein (LOXL, such as LOXL2), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mcl-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2,3,6), Membrane copper amine oxidase, Mesothelin, MET tyrosine kinase, Metabotropic glutamate receptor 1, Metalloreductase STEAP1 (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Omithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly ADP ribose polymerase (PARP, such as PARP1, 2 and 3), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, RosI tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Semaphorin-4D, Serine protease, serine/threonine kinase (STK), serine/threonine-protein kinase (TBK, such as TBKI), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Spl) transcription factor, Sphingomyelin synthase, Sphingosine kinase (such as 1, 2), Sphingosine-1-phosphate receptor-1, spleen tyrosine kinase (SYK), SRC gene, Src tyrosine kinase, STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, TGF beta 2 ligand, Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, Transferrin, Transforming growth factor (TGF, such as beta) kinase, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E21 (UBE2I, UBC9), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase Yes, Wee-1 protein kinase, Wilms' tumor antigen 1, Wilms' tumor protein, X-linked inhibitor of apoptosis protein, Zinc finger protein transcription factor or any combination thereof.

Non-limiting examples of additional therapeutic agents may be categorized by their mechanism of action into, for example, the following groups:

anti-metabolites/anti-cancer agents, such as pyrimidine analogs floxuridine, capecitabine, cytarabine, CPX-351 (liposomal cytarabine, daunorubicin), and TAS-118;

purine analogs, folate antagonists (such as pralatrexate), and related inhibitors;

antiproliferative/antimitotic agents including natural products, such as vinca alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide);

DNA damaging agents, such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, merchlorethamine, mitomycin C, mitoxantrone, nitrosourea, procarbazine, taxol, Taxotere, teniposide, etoposide, and triethylenethiophosphoramide;

DNA-hypomethylating agents, such as guadecitabine (SGI-110), ASTX727;

antibiotics such as dactinomycin, daunorubicin, doxorubicin, idarubicin, anthracyclines, mitoxantrone, bleomycins, plicamycin (mithramycin);

enzymes such as L-asparaginase which systemically metabolizes L-asparagine and deprives cells which do not have the capacity to synthesize their own asparagine;

antiplatelet agents;

DNAi oligonucleotides targeting Bcl-2, such as PNT2258;

agents that activate or reactivate latent human immunodeficiency virus (HIV), such as panobinostat and romidepsin;

asparaginase stimulators, such as crisantaspase (Erwinase®) and GRASPA (ERY-001, ERY-ASP), calaspargase pegol;

pan-Trk, ROS1 and ALK inhibitors, such as entrectinib, TPX-0005;

anaplastic lymphoma kinase (ALK) inhibitors, such as alectinib, ceritinib;

antiproliferative/antimitotic alkylating agents, such as nitrogen mustard cyclophosphamide and analogs (melphalan, chlorambucil, hexamethylmelamine, thiotepa), alkyl nitrosoureas (carmustine) and analogs, streptozocin, and triazenes (dacarbazine);

antiproliferative/antimitotic antimetabolites, such as folic acid analogs (methotrexate);

platinum coordination complexes (cisplatin, oxiloplatinim, and carboplatin), procarbazine, hydroxyurea, mitotane, and aminoglutethimide;

hormones, hormone analogs (estrogen, tamoxifen, goserelin, bicalutamide, and nilutamide), and aromatase inhibitors (letrozole and anastrozole);

anticoagulants such as heparin, synthetic heparin salts, and other inhibitors of thrombin;

fibrinolytic agents such as tissue plasminogen activator, streptokinase, urokinase, aspirin, dipyridamole, ticlopidine, and clopidogrel;

antimigratory agents;

antisecretory agents (breveldin);

immunosuppressives, such as tacrolimus, sirolimus, azathioprine, and mycophenolate;

growth factor inhibitors, and vascular endothelial growth factor inhibitors;

fibroblast growth factor inhibitors, such as FPA14;

anti-VEGFR antibodies, such as IMC-3C5, GNR-011, tanibirumab;

anti-VEGF/DDL4 antibodies, such as ABT-165;

anti-cadherins antibodies, such as HKT-288;

anti-CD70 antibodies, such as AMG-172; anti-leucine-rich repeat containing 15 (LRRC15) antibodies, such as ABBV-085. ARGX-110;

angiotensin receptor blockers, nitric oxide donors;

antisense oligonucleotides, such as AEG35156, IONIS-KRAS-2.5Rx, EZN-3042, RX-0201, IONIS-AR-2.5Rx, BP-100 (prexigebersen), IONIS-STAT3-2.5Rx;

DNA interference oligonucleotides, such as PNT2258, AZD-9150;

anti-ANG-2 antibodies, such as MEDI3617, and LY3127804;

anti-ANG-1/ANG-2 antibodies, such as AMG-780;

anti-MET/EGFR antibodies, such as LY3164530;

anti-EGFR antibodies, such as ABT-414, AMG-595, necitumumab, ABBV-221, depatuxizumab mafodotin (ABT-414), tomuzotuximab, ABT-806, vectibix, modotuximab, RM-1929;

anti-CSF1R antibodies, such as emactuzumab, LY3022855, AMG-820, FPA-008 (cabiralizumab);

anti-CD40 antibodies, such as RG7876, SEA-CD40, APX-005M, ABBV-428;

anti-endoglin antibodies, such as TRC105 (carotuximab);

anti-CD45 antibodies, such as 131I-BC8 (lomab-B);

anti-HER3 antibodies, such as LJM716, GSK2849330;

anti-HER2 antibodies, such as margetuximab, MEDI4276, BAT-8001;

anti-HLA-DR antibodies, such as IMMU-114;

anti-IL-3 antibodies, such as JNJ-56022473;

anti-OX40 antibodies, such as MEDI6469, MEDI6383, MEDI0562 (tavolixizumab), MOXR0916, PF-04518600, RG-7888, GSK-3174998, INCAGN1949, BMS-986178, GBR-8383, ABBV-368;

anti-EphA3 antibodies, such as KB-004;

anti-CD20 antibodies, such as obinutuzumab, IGN-002;

anti-CD20/CD3 antibodies, such as RG7828;

anti-CD37 antibodies, such as AGS67E, otlertuzumab (TRU-016);

anti-ENPP3 antibodies, such as AGS-16C3F;

anti-FGFR-3 antibodies, such as LY3076226, B-701;

anti-FGFR-2 antibodies, such as GAL-F2;

anti-C5 antibodies, such as ALXN-1210;

anti-CD27 antibodies, such as varlilumab (CDX-1127);

anti-TROP-2 antibodies, such as IMMU-132 anti-NKG2a antibodies, such as monalizumab;

anti-VISTA antibodies, such as HMBD-002;

anti-PVRIG antibodies, such as COM-701;

anti-EpCAM antibodies, such as VB4-845;

anti-BCMA antibodies, such as GSK-2857916 anti-CEA antibodies, such as RG-7813;

anti-cluster of differentiation 3 (CD3) antibodies, such as MGD015;

anti-folate receptor alpha antibodies, such as IMGN853;

MCL-1 inhibitors, such as AMG-176, S-64315, and AZD-5991, 483-LM, A-1210477, UMI-77, JKY-5-037;

epha2 inhibitors, such as MM-310;

anti LAG-3 antibodies, such as relatlimab (ONO-4482), LAG-525, MK-4280, REGN-3767;

raf kinase/VEGFR inhibitors, such as RAF-265;

polycomb protein (EED) inhibitors, such as MAK683;

anti-fibroblast activation protein (FAP)/IL-2R antibodies, such as RG7461;

anti-fibroblast activation protein (FAP)/TRAIL-R2 antibodies, such as RG7386;

anti-fucosyl-GM1 antibodies, such as BMS-986012;

p38 MAP kinase inhibitors, such as ralimetinib;

PRMT1 inhibitors, such as MS203;

Sphingosine kinase 2 (SK2) inhibitors, such as opaganib;

FLT3-ITD inhibitors, such as BCI-332;

Nuclear erythroid 2-related factor 2 stimulators, such as omaveloxolone (RTA-408);

Tropomyosin receptor kinase (TRK) inhibitors, such as LOXO-195, ONO-7579;

anti-ICOS antibodies, such as JTX-2011, GSK3359609;

anti-DR5 (TRAIL2) antibodies, such as DS-8273;

anti-GD2 antibodies, such as APN-301;

anti-interleukin-17 (IL-17) antibodies, such as CJM-112;

anti-carbonic anhydrase IX antibodies, such as TX-250;

anti-CD38-attenukine, such as TAK573;

anti-Mucin 1 antibodies, such as gatipotuzumab;

Mucin 1 inhibitors, such as GO-203-2C;

MARCKS protein inhibitors, such as BIO-11006;

Folate antagonists, such as arfolitixorin;

Galectin-3 inhibitors, such as GR-MD-02;

Phosphorylated P68 inhibitors, such as RX-5902;

CD95/TNF modulators, such as ofranergene obadenovec;

PI3K/Akt/mTOR inhibitors, such as ABTL-0812;

pan-PIM kinase inhibitors, such as INCB-053914;

IL-12 gene stimulators, such as EGEN-001, tavokinogene telseplasmid;

Heat shock protein HSP90 inhibitors, such as TAS-116, PEN-866;

VEGF/HGF antagonists, such as MP-0250;

SYK tyrosine kinase/FLT3 tyrosine kinase inhibitors, such as TAK-659;

SYK tyrosine kinase/JAK tyrosine kinase inhibitors, such as ASN-002;
FLT3 tyrosine kinase inhibitor, such as FF-10101;
FLT3 tyrosine kinase agonist, such as CDX-301;
FLT3/MEK1 inhibitors, such as E-6201;
IL-24 antagonist, such as AD-IL24;
RIG-I agonists, such as RGT-100;
Aerolysin stimulators, such as topsalysin;
P-Glycoprotein 1 inhibitors, such as HM-30181A;
CSF-1 antagonists, such as ARRY-382, BLZ-945;
anti-Mesothelin antibodies, such as SEL-403;
Thymidine kinase stimulators, such as aglatimagene besadenovec;
Polo-like kinase 1 inhibitors, such as PCM-075;
TLR-7 agonists, such as TMX-101 (imiquimod);
NEDD8 inhibitors, such as pevonedistat (MLN-4924), TAS-4464;
Pleiotropic pathway modulators, such as avadomide (CC-122);
FoxM1 inhibitors, such as thiostrepton;
Anti-MUC1 antibodies, such as Mab-AR-20.5;
anti-CD38 antibodies, such as isatuximab, MOR-202;
UBA1 inhibitors, such as TAK-243;
Src tyrosine kinase inhibitors, such as VAL-201;
VDAC/HK inhibitors, such as VDA-1102;
BRAF/PI3K inhibitors, such as ASN-003;
Elf4a inhibitors, such as rohinitib, eFT226;
TP53 gene stimulators, such as ad-p53;
PD-L1/EGFR inhibitors, such as GNS-1480;
Retinoic acid receptor alpha (RARα) inhibitors, such as SY-1425;
SIRT3 inhibitors, such as YC8-02;
Stromal cell-derived factor 1 ligand inhibitors, such as olaptesed pegol (NOX-A12);
IL-4 receptor modulators, such as MDNA-55;
Arginase-I stimulators, such as pegzilarginase;
Topoisomerase I inhibitor/hypoxia inducible factor-1 alpha inhibitors, such as PEG-SN38 (firtecan pegol);
Hypoxia inducible factor-1 alpha inhibitors, such as PT-2977, PT-2385;
CD122 agonists such as NKTR-214;
p53 tumor suppressor protein stimulators such as kevetrin;
Mdm4/Mdm2 p53-binding protein inhibitors, such as ALRN-6924;
kinesin spindle protein (KSP) inhibitors, such as filanesib (ARRY-520);
CD80-fc fusion protein inhibitors, such as FPT-155;
Menin and mixed lineage leukemia (MLL) inhibitors such as KO-539;
Liver x receptor agonists, such as RGX-104;
IL-10 agonists, such as AM-0010;
EGFR/ErbB-2 inhibitors, such as varlitinib;
VEGFR/PDGFR inhibitors, such as vorolanib;
IRAK4 inhibitors, such as CA-4948;
anti-TLR-2 antibodies, such as OPN-305;
Calmodulin modulators, such as CBP-501;
Glucocorticoid receptor antagonists, such as relacorilant (CORT-125134);
Second mitochondria-derived activator of caspases (SMAC) protein inhibitors, such as BI-891065;
Lactoferrin modulators, such as LTX-315;
Kit tyrosine kinase/PDGF receptor alpha antagonists such as DCC-2618;
KIT inhibitors, such as PLX-9486;
Exportin 1 inhibitors, such as eltanexor;
EGFR/ErbB2/Ephb4 inhibitors, such as tesevatinib;
anti-CD33 antibodies, such as IMGN-779;
anti-KMA antibodies, such as MDX-1097;
anti-TIM-3 antibodies, such as TSR-022, LY-3321367, MBG-453;
anti-CD55 antibodies, such as PAT-SC1;
anti-PSMA antibodies, such as ATL-101;
anti-CD100 antibodies, such as VX-15;
anti-EPHA3 antibodies, such as fibatuzumab;
anti-Erbb antibodies, such as CDX-3379, HLX-02, seribantumab;
anti-APRIL antibodies, such as BION-1301;
Anti-Tigit antibodies, such as BMS-986207, RG-6058;
CHST15 gene inhibitors, such as STNM-01;
RAS inhibitors, such as NEO-100;
Somatostatin receptor antagonist, such as OPS-201;
CEBPA gene stimulators, such as MTL-501;
DKK3 gene modulators, such as MTG-201;
p70s6k inhibitors, such as MSC2363318A;
methionine aminopeptidase 2 (MetAP2) inhibitors, such as M8891, APL-1202;
arginine N-methyltransferase 5 inhibitors, such as GSK-3326595;
anti-programmed cell death protein 1 (anti-PD-1) antibodies, such as nivolumab (OPDIVO®, BMS-936558, MDX-1106), pembrolizumab (KEYTRUDA®, MK-3477, SCH-900475, lambrolizumab, CAS Reg. No. 1374853-91-4), pidilizumab, PF-06801591, BGB-A317, GLS-010 (WBP-3055), AK-103 (HX-008), MGA-012, BI-754091, REGN-2810 (cemiplimab), AGEN-2034, JS-001, JNJ-63723283, genolimzumab (CBT-501), LZM-009, BCD-100, LY-3300054, SHR-1201, BAT-1306, and anti-programmed death-ligand 1 (anti-PD-L1) antibodies such as BMS-936559, atezolizumab (MPDL3280A), durvalumab (MEDI4736), avelumab, CK-301, (MSB0010718C), MEDI0680, CX-072, CBT-502, PDR-001 (spartalizumab), TSR-042 (dostarlimab), JTX-4014, BGB-A333, SHR-1316, CS-1001 (WBP-3155, KN-035, IBI-308, FAZ-053, and MDXi105-01;
PD-L1/VISTA antagonists such as CA-170;
anti-PD-L1/TGFβ antibodies, such as M7824;
anti-transferrin antibodies, such as CX-2029;
anti-IL-8 (Interleukin-8) antibodies, such as HuMax-Inflam;
ATM (ataxia telangiectasia) inhibitors, such as AZD0156;
CHK1 inhibitors, such as GDC-0575, LY2606368 (prexasertib), SRA737, RG7741 (CHK1/2);
CXCR4 antagonists, such as BL-8040, LY2510924, burixafor (TG-0054), X4P-002, X4P-001-10;
EXH2 inhibitors, such as GSK2816126;
HER2 inhibitors, such as neratinib, tucatinib (ONT-380);
KDM1 inhibitors, such as ORY-1001, IMG-7289, INCB-59872, GSK-2879552;
CXCR2 antagonists, such as AZD-5069;
GM-CSF antibodies, such as lenzilumab;
DNA dependent protein kinase inhibitors, such as MSC2490484A (nedisertib), VX-984, AsiDNA (DT-01);
protein kinase C (PKC) inhibitors, such as LXS-196, sotrastaurin;
Selective estrogen receptor downregulators (SERD), such as fulvestrant (Faslodex®), RG6046, RG6047, elacestrant (RAD-1901) and AZD9496;
Selective estrogen receptor covalent antagonists (SERCAs), such as H3B-6545;
selective androgen receptor modulator (SARM), such as GTX-024, darolutamide;
transforming growth factor-beta (TGF-beta) kinase antagonists, such as galunisertib;

anti-transforming growth factor-beta (TGF-beta) antibodies, such as LY3022859, NIS793, XOMA 089;

bispecific antibodies, such as MM-141 (IGF-1/ErbB3), MM-111 (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietins/VEGF), PF-06671008 (Cadherins/CD3), AFM-13 (CD16/CD30), APV0436 (CD123/CD3), flotetuzumab (CD123/CD3), REGN-1979 (CD20/CD3), MCLA-117 (CD3/CLECi2A), MCLA-128 (HER2/HER3), JNJ-0819, JNJ-7564 (CD3/heme), AMG-757 (DLL3-CD3), MGD-013 (PD-1/LAG-3), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), MGD-009 (CD3/B7H3);

Mutant selective EGFR inhibitors, such as PF-06747775, EGF816 (nazartinib), ASP8273, ACEA-0010, BI-1482694;

Anti-GITR (glucocorticoid-induced tumor necrosis factor receptor-related protein) antibodies, such as MEDI1873, FPA-154, INCAGN-1876, TRX-518, BMS-986156, MK-1248, GWN-323;

anti-delta-like protein ligand 3 (DDL3) antibodies, such as rovalpituzumab tesirine;

anti-clusterin antibodies, such as AB-16B5;

anti-Ephrin-A4 (EFNA4) antibodies, such as PF-06647263;

anti-RANKL antibodies, such as denosumab;

anti-mesothelin antibodies, such as BMS-986148, Anti-MSLN-MMAE;

anti-sodium phosphate cotransporter 2B (NaP2B) antibodies, such as lifastuzumab;

anti-c-Met antibodies, such as ABBV-399;

Adenosine A2A receptor antagonists, such as CPI-444, AZD-4635, preladenant, PBF-509;

Alpha-ketoglutarate dehydrogenase (KGDH) inhibitors, such as CPI-613;

XPO1 inhibitors, such as selinexor (KPT-330);

Isocitrate dehydrogenase 2 (IDH2) inhibitors, such as enasidenib (AG-221);

IDH1 inhibitors such as AG-120, and AG-881 (IDH1 and IDH2), IDH-305, BAY-1436032;

interleukin-3 receptor (IL-3R) modulators, such as SL-401;

Arginine deiminase stimulators, such as pegargiminase (ADI-PEG-20);

antibody-drug conjugates, such as MLN0264 (anti-GCC, guanylyl cyclase C), T-DM1 (trastuzumab emtansine, Kadcycla), milatuzumab-doxorubicin (hCD74-DOX), brentuximab vedotin, DCDT2980S, polatuzumab vedotin, SGN-CD70A, SGN-CD19A, inotuzumab ozogamicin, lorvotuzumab mertansine, SAR3419, isactuzumab govitecan, enfortumab vedotin (ASG-22ME), ASG-15ME, DS-8201 (trastuzumab deruxtecan), 225Ac-lintuzumab, U3-1402, 177Lu-tetraxetan-tetuloma, tisotumab vedotin, anetumab ravtansine, CX-2009, SAR-566658, W-0101, polatuzumab vedotin, ABBV-085;

claudin-18 inhibitors, such as claudiximab;

β-catenin inhibitors, such as CWP-291;

anti-CD73 antibodies, such as MEDI-9447 (oleclumab), CPX-006, IPH-53, BMS-986179;

CD73 antagonists, such as AB-680, PSB-12379, PSB-12441, PSB-12425;

CD39/CD73 antagonists, such as PBF-1662;

chemokine receptor 2 (CCR) inhibitors, such as PF-04136309, CCX-872, BMS-813160 (CCR2/CCR5);

thymidylate synthase inhibitors, such as ONX-0801;

ALK/ROS1 inhibitors, such as lorlatinib;

tankyrase inhibitors, such as G007-LK;

Mdm2 p53-binding protein inhibitors, such as CMG-097, HDM-201;

c-PIM inhibitors, such as PIM447;

BRAF inhibitors, such as dabrafenib, vemurafenib, encorafenib (LGX818), PLX8394;

sphingosine kinase-2 (SK2) inhibitors, such as Yeliva® (ABC294640);

cell cycle inhibitors, such as selumetinib (MEK1/2), and sapacitabine;

AKT inhibitors such as MK-2206, ipatasertib, afuresertib, AZD5363, and ARQ-092, capivasertib, triciribine;

anti-CTLA-4 (cytotoxic T-lymphocyte protein-4) inhibitors, such as tremelimumab, AGEN-1884, BMS-986218;

c-MET inhibitors, such as AMG-337, savolitinib, tivantinib (ARQ-197), capmatinib, and tepotinib, ABT-700, AG213, AMG-208, JNJ-38877618 (OMO-1), merestinib, HQP-8361;

c-Met/VEGFR inhibitors, such as BMS-817378, TAS-115;

c-Met/RON inhibitors, such as BMS-777607;

BRAF/EGFR inhibitors, such as BGB-283;

bcr/abl inhibitors, such as rebastinib, asciminib;

MNK1/MNK2 inhibitors, such as eFT-508;

mTOR inhibitor/cytochrome P450 3A4 stimulators, such as TYME-88;

lysine-specific demethylase-1 (LSD1) inhibitors, such as CC-90011;

Pan-RAF inhibitors, such as LY3009120, LXH254, TAK-580;

Raf/MEK inhibitors, such as RG7304;

CSF1R/KIT and FLT3 inhibitors, such as pexidartinib (PLX3397);

kinase inhibitors, such as vandetanib;

E selectin antagonists, such as GMI-1271;

differentiation inducers, such as tretinoin;

epidermal growth factor receptor (EGFR) inhibitors, such as osimertinib (AZD-9291);

topoisomerase inhibitors, such as doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114);

corticosteroids, such as cortisone, dexamethasone, hydrocortisone, methylprednisolone, prednisone, prednisolone;

growth factor signal transduction kinase inhibitors;

nucleoside analogs, such as DFP-10917;

Axl inhibitors, such as BGB-324 (bemcentinib), SLC-0211;

BET inhibitors, such as INCB-054329, INCB057643, TEN-010, AZD-5153, ABT-767, BMS-986158, CC-90010, GSK525762 (molibresib), NHWD-870, ODM-207,GSK-2820151, GSK-1210151A, ZBC246, ZBC260, ZEN3694, FT-1101, RG-6146, CC-90010, mivebresib, BI-894999, PLX-2853, PLX-51107, CPI-0610, GS-5829;

PARP inhibitors, such as olaparib, rucaparib, veliparib, talazoparib, ABT-767, BGB-290;

Proteasome inhibitors, such as ixazomib, carfilzomib (Kyprolis®), marizomib;

Glutaminase inhibitors, such as CB-839;

Vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU- 131; bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, stapuldencel-T, eltrapuldencel-T, SL-701, BSK01TM, rocapuldencel-T (AGS-003), DCVAC, CVac™, stapuldencel-T, eltrapuldencel-T, SL-701, BSKO1™, ADXS31-142; oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, PF-06753512, VBI-1901, TG-4010, ProscaVax™; tumor cell vaccines, such as Vigil® (IND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; GI-4000;

anti-DLL4 (delta like ligand 4) antibodies, such as demcizumab;

STAT-3 inhibitors, such as napabucasin (BBI-608);

ATPase p97 inhibitors, such as CB-5083;

smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole;

interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus)(Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon);

interferon gamma ligand modulators, such as interferon gamma (OH-6000, Ogamma 100);

IL-6 receptor modulators, such as tocilizumab, siltuximab, AS-101 (CB-06-02, IVX-Q-101);

Telomerase modulators, such as, tertomotide (GV-1001, HR-2802, Riavax) and imetelstat (GRN-163, JNJ-63935937);

DNA methyltransferases inhibitors, such as temozolomide (CCRG-81045), decitabine, guadecitabine (S-110, SGI-110), KRX-0402, RX-3117, RRx-001, and azacitidine;

DNA gyrase inhibitors, such as pixantrone and sobuzoxane;

Bcl-2 family protein inhibitors, such as ABT-263, venetoclax (ABT-199), ABT-737, and AT-101;

Notch inhibitors, such as LY3039478 (crenigacestat), tarextumab (anti-Notch2/3), BMS-906024;

anti-myostatin inhibitors, such as landogrozumab;

hyaluronidase stimulators, such as PEGPH-20;

Wnt pathway inhibitors, such as SM-04755, PRI-724, WNT-974;

gamma-secretase inhibitors, such as PF-03084014, MK-0752, RO-4929097;

Grb-2 (growth factor receptor bound protein-2) inhibitors, such as BP1001;

TRAIL pathway-inducing compounds, such as ONC201, ABBV-621;

Focal adhesion kinase inhibitors, such as VS-4718, defactinib, GSK2256098;

hedgehog inhibitors, such as saridegib, sonidegib (LDE225), glasdegib and vismodegib;

Aurora kinase inhibitors, such as alisertib (MLN-8237), and AZD-2811,AMG-900, barasertib, ENMD-2076;

HSPB1 modulators (heat shock protein 27, HSP27), such as brivudine, apatorsen;

ATR inhibitors, such as BAY-937, AZD6738, AZD6783, VX-803, VX-970 (berzosertib) and VX-970;

mTOR inhibitors, such as sapanisertib and vistusertib (AZD2014), ME-344;

mTOR/PI3K inhibitors, such as gedatolisib, GSK2141795, omipalisib, RG6114;

Hsp90 inhibitors, such as AUY922, onalespib (AT13387), SNX-2112, SNX5422;

Murine double minute (mdm2) oncogene inhibitors, such as DS-3032b, RG7775, AMG-232, HDM201, and idasanutlin (RG7388);

CD137 agonists, such as urelumab, utomilumab (PF-05082566);

STING agonists, such as ADU-S100 (MIW-815), SB-11285, MK-1454, SR-8291, AdVCA0848, GSK-532, SYN-STING, MSA-1, SR-8291;

FGFR inhibitors, such as FGF-401, INCB-054828, BAY-1163877, AZD4547, JNJ-42756493, LY2874455, Debio-1347;

fatty acid synthase (FASN) inhibitors, such as TVB-2640;

Anti-KIR monoclonal antibodies, such as lirilumab (IPH-2102), IPH-4102;

Antigen CD19 inhibitors, such as MOR208, MEDI-551, AFM-11, inebilizumab;

CD44 binders, such as A6;

protein phosphatase 2A (PP2A) inhibitors, such as LB-100;

CYP17 inhibitors, such as seviteronel (VT-464), ASN-001, ODM-204, CFG920, abiraterone acetate;

RXR agonists, such as IRX4204;

hedgehog/smoothened (hh/Smo) antagonists, such as taladegib, patidegib;

complement C3 modulators, such as Imprime PGG;

IL-15 agonists, such as ALT-803, NKTR-255, and hetIL-15;

EZH2 (enhancer of zeste homolog 2) inhibitors, such as tazemetostat, CPI-1205, GSK-2816126;

Oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, OBP-301;

DOT1L (histone methyltransferase) inhibitors, such as pinometostat (EPZ-5676);

toxins such as Cholera toxin, ricin, *Pseudomonas* exotoxin, *Bordetella pertussis* adenylate cyclase toxin, diphtheria toxin, and caspase activators;

DNA plasmids, such as BC-819;

PLK inhibitors of PLK 1, 2, and 3, such as volasertib (PLK);

WEE inhibitors, such as AZD1775 (adavosertib);

Rho kinase (ROCK) inhibitors, such as AT13148, KD025;

ERK inhibitors, such as GDC-0994, LY3214996, MK-8353;

IAP inhibitors, such as ASTX660, debio-1143, birinapant, APG-1387, LCL-161;

RNA polymerase inhibitors, such has lurbinectedin (PM-1183), CX-5461;

Tubulin inhibitors, such as PM-184, BAL-101553 (lisavanbulin), and OXI-4503, fluorapacin (AC-0001), plinabulin;

Toll-like receptor 4 (TL4) agonists, such as G100, GSK1795091, and PEPA-10;

Elongation factor 1 alpha 2 inhibitors, such as plitidepsin;

CD95 inhibitors, such as APG-101, APO-010, asunercept;

WTT inhibitors, such as DSP-7888;

splicing factor 3B subunit1 (SF3B1) inhibitors, such as H3B-8800;

PDGFR alpha/KIT mutant-specific inhibitors such as BLU-285;

SHP-2 inhibitors, such as TNO155 (SHP-099), RMC-4550; and retinoid Z receptor gamma (RORγ) agonists, such as LYC-55716.

In some embodiments, provided herein are methods of treating or preventing a hyperproliferative disorder or cancer in a human or animal having or at risk of having the hyperproliferative disorder or cancer is provided, comprising administering to the human or animal a therapeutically effective amount of a compound as disclosed herein, or a pharmaceutically acceptable salt thereof, in combination with a therapeutically effective amount of one or more (e.g., one, two, three, one or two, or one to three) additional therapeutic agents selected from the group consisting of apoptosis signal-regulating kinase (ASK) inhibitors; Bruton's tyrosine kinase (BTK) inhibitors; cluster of differentiation 47 (CD47) inhibitors; cyclin-dependent kinase (CDK) inhibitors; discoidin domain receptor (DDR) inhibitors; histone deacetylase (HDAC) inhibitors; indoleamine-pyrrole-2,3-dioxygenase (IDO1) inhibitors; Janus kinase (JAK) inhibitors; lysyl oxidase-like protein (LOXL) inhibitors; matrix metalloprotease (MMP) inhibitors; mitogen-activated protein kinase (MEK) inhibitors; phosphatidylinositol 3-kinase (PI3K) inhibitors; spleen tyrosine kinase (SYK) inhibitors; toll-like receptor 8 (TLR8) inhibitors; toll-like receptor 9 (TLR9) inhibitors; tyrosine-kinase inhibitors (TKIs), and any combination thereof, or a pharmaceutically acceptable salt thereof. Non-limiting examples include:

Apoptosis Signal-Regulating Kinase (ASK) Inhibitors: ASK inhibitors include ASKI inhibitors. Examples of ASKI inhibitors include, but are not limited to, those described in WO 2011/008709 (Gilead Sciences) and WO 2013/112741 (Gilead Sciences);

Bruton's Tyrosine Kinase (BTK) Inhibitors: Examples of BTK inhibitors include, but are not limited to, (S)-6-amino-9-(1-(but-2-ynoyl)pyrrolidin-3-yl)-7-(4-phenoxyphenyl)-7H-purin-8 (9H)-one, acalabrutinib (ACP-196), BGB-3111, CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315;

Cluster of Differentiation 47 (CD47) inhibitors: Examples of CD47 inhibitors include, but are not limited to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621;

Cyclin-dependent Kinase (CDK) Inhibitors: CDK inhibitors include inhibitors of CDK 1, 2, 3, 4, 6,7 and 9, such as abemaciclib, alvocidib (HMR-1275,flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, and TG-02;

Discoidin Domain Receptor (DDR) Inhibitors: DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations);

Histone Deacetylase (HDAC) Inhibitors: Examples of HDAC inhibitors include, but are not limited to, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, entinostat;

Indoleamine-pyrrole-2,3-dioxygenase (IDO) inhibitors: Examples of IDO1 inhibitors include, but are not limited to, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916;

Janus Kinase (JAK) Inhibitors: JAK inhibitors inhibit JAK1, JAK2, and/or JAK3. Examples of JAK inhibitors include, but are not limited to, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019;

Lysyl Oxidase-Like Protein (LOXL) Inhibitors: LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics);

Matrix Metalloprotease (MMP) Inhibitors: MMP inhibitors include inhibitors of MMP1 through 10. Examples of MMP9 inhibitors include, but are not limited to, marimastat (BB-2516), cipemastat (Ro 32-3555), GS-5745 (andecaliximab) and those described in WO 2012/027721 (Gilead Biologics);

Mitogen-activated Protein Kinase (MEK) Inhibitors: MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, refametinib;

Phosphatidylinositol 3-kinase (PI3K) Inhibitors: PI3K inhibitors include inhibitors of PI3Kγ, PI3Kδ, PI3Kβ, PI3Kα, and/or pan-PI3K. Examples of PI3K inhibitors include, but are not limited to, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TGI00115, TGR-1202 (umbralisib), TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences);

Spleen Tyrosine Kinase (SYK) Inhibitors: Examples of SYK inhibitors include, but are not limited to, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Conn.) and those described in U.S. 2015/0175616;

Toll-like receptor 8 (TLR8) inhibitors: Examples of TLR8 inhibitors include, but are not limited to, E-6887, IMO-4200, IMO-8400, IMO-9200, MCT-465, MEDI-9197, motolimod, resiquimod, VTX-1463, and VTX-763;

Toll-like receptor 9 (TLR9) inhibitors: Examples of TLR9 inhibitors include, but are not limited to, AST-008, IMO-2055, IMO-2125, lefitolimod, litenimod, MGN-1601, and PUL-042; and Tyrosine-kinase Inhibitors (TKIs): TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, tivoanib, and TH-4000, MEDI-575 (anti-PDGFR antibody).

As used herein, the term "chemotherapeutic agent" or "chemotherapeutic" (or "chemotherapy" in the case of treatment with a chemotherapeutic agent) is meant to encompass any non-proteinaceous (i.e., non-peptidic) chemical compound useful in the treatment of cancer. Examples of chemotherapeutic agents include but are not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlomaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiII), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFIRI (fluorouracil, leucovorin, and irinotecan); and pharmaceutically acceptable salts, acids, or derivatives of any of the above.

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Anti-Hormonal Agents

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204.

Examples of progesterone receptor antagonist include onapristone.

Anti-Angiogenic Agents

Anti-angiogenic agents include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, $\alpha,\alpha'$-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

Anti-fibrotic agents include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Immunotherapeutic Agents

The immunotherapeutic agents include and are not limited to therapeutic antibodies suitable for treating subjects. Some examples of therapeutic antibodies include abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

Cancer Gene Therapy and Cell Therapy

Cancer Gene Therapy and Cell Therapy includes the insertion of a normal gene into cancer cells to replace a mutated or altered gene; genetic modification to silence a mutated gene; genetic approaches to directly kill the cancer cells; including the infusion of immune cells designed to replace most of the subject's own immune system to enhance the immune response to cancer cells, or activate the subject's own immune system (T cells or Natural Killer cells) to kill cancer cells, or find and kill the cancer cells; genetic approaches to modify cellular activity to further alter endogenous immune responsiveness against cancer.

Gene Editors

Examples of genome editing system include a CRISPR/Cas9 system, a zinc finger nuclease system, a TALEN system, a homing endonucleases system, and a meganuclease system.

CAR-T Cell Therapy and TCR-T Cell Therapy

CAR-T cell therapy includes a population of immune effector cells engineered to express a chimeric antigen receptor (CAR), wherein the CAR comprises a tumor antigen-binding domain. The immune effector cell is a T cell or an NK cell. TCR-T cell therapy includes TCR-T cells that are engineered to target tumor derived peptides present on the surface of tumor cells. Cells can be autologous or allogeneic.

In some embodiments, the CAR comprises an antigen binding domain, a transmembrane domain, and an intracellular signaling domain.

In some embodiments, the intracellular domain comprises a primary signaling domain, a costimulatory domain, or both of a primary signaling domain and a costimulatory domain.

In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon R1b), CD79a, CD79b, Fcgamma RIIa, DAP10, and DAP12.

In some embodiments, the costimulatory domain comprises a functional domain of one or more proteins selected from the group consisting of CD27, CD28, 4-1BB (CD137), OX40, CD30, CD40, PD-1, ICOS, lymphocyte function-associated antigen-1 (LFA-I), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD 1 ld, ITGAE, CD103, ITGAL, CD 1 la, LFA-1, ITGAM, CDi 1b, ITGAX, CD1 lc, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD1 la, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R u, ITGA1, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, TNFR2, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), SLAMF6 (NTB-A, Ly108), SLAM (SLAMFI, CD150, IPO-3), BLAME (SLAMF8), SELPLG (CD162), LTBR, PAG/Cbp, NKp44, NKp30, NKp46, NKG2D, and NKG2C.

In some embodiments, the antigen binding domain binds a tumor antigen.

In some embodiments, the tumor antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvlll); ganglioside G2 (GD2); ganglioside GD3 (aNeuSAc(2-8)aNeuSAc(2-3)bD-Gaip(1-4)bDGIcp(1-1)Cer); TNF receptor family member B cell maturation (BCMA); Tn antigen ((Tn Ag) or (GaNAcu-Ser/Thr)); prostate-specific membrane antigen (PSMA); Receptor tyrosine kinase-like orphan receptor 1 (RORI); Fms-Like, Tyrosine Kinase 3 (FLT3); Tumor-associated glycoprotein 72 (TAG72); CD38; CD44v6; Carcinoembryonic antigen (CEA); Epithelial cell adhesion molecule (EP-CAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y)antigen; CD24; Platelet-derived growth factor receptor beta (PDGFR-beta); Stage-specific embryonic antigen-4 (SSEA-4); CD20; delta like 3 (DLL3); Folate receptor alpha; Receptor tyrosine-protein kinase, ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeuSAc(2-3)bDGalp(1-4)bDGlcp(1-1)Cer); transglutaminase 5 (TGS5); high molecular weight-melanoma associated antigen (HMWMAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GoboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (ORS IE2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRI); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLECi2A); bone marrow stromal cell antigen 2 (BST2); EGF-like module containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the tumor antigen is selected from CD150, 5T4, ActRIIA, B7, BMCA, CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, GD2, GD3, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-IIRalpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

Non limiting examples of cell therapies include Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CART cells, autologous 4H11-28z/fnL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502,CMD-601, CMD-602, CSG-005.

In some embodiments, the tumor targeting antigen includes: Alpha-fetoprotein, such as ET-1402, and AFP-TCR; Anthrax toxin receptor 1, such as anti-TEM8 CAR T-cell therapy; B cell maturation antigens (BCMA), such as bb-2121, UCART-BCMA, ET-140, KITE-585, MCM-998, LCAR-B38M, CART-BCMA, SEA-BCMA, BB212, UCART-BCMA, ET-140, P-BCMA-101, AUTO-2 (APRIL-CAR); Anti-CLL-1 antibodies, such as KITE-796; B7 homolog 6, such as CAR-NKp30 and CAR-B7H6; B-lymphocyte antigen CD19, such as TBI-1501, CTL-119 huCART-19 T cells, JCAR-015 U.S. Pat. No. 7,446,190, JCAR-014, JCAR-017, (WO2016196388, WO2016033570, WO2015157386), axicabtagene ciloleucel (KTE-C19), U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, IM19 CAR-T; B-lymphocyte antigen CD20, such as ATTCK-20; B-lymphocyte cell adhesion, such as UCART-22, JCAR-018 WO2016090190; NY-ESO-1, such as GSK-3377794, TBI-1301; Carbonic anhydrase, such as DC-Ad-GMCAIX; Caspase 9 suicide gene, such as CaspaCIDe DLI, BPX-501; CCR5, such as SB-728; CDw123, such as MB-102, UCART-123; CD20m such as CBM-C20.1; CD4, such as ICG-122; CD30, such as CART30 (CBM-C30.1; CD33, such as CIK-CAR.CD33; CD38, such as T-007, UCART-38; CD40 ligand, such as BPX-201; CEACAM protein 4 modulators, such as MG7-CART; Claudin 6, such as CSG-002; EBV targeted, such as CMD-003; EGFR, such as autologous 4H11-28z/fIL-12/EFGRt T cell; Endonuclease, such as PGN-514, PGN-201; Epstein-Barr virus specific T-lymphocytes, such as TT-10; Erbb2, such as CST-102, CIDeCAR; Ganglioside (GD2), such as 4SCAR-GD2; Glutamate carboxypeptidase II, such as CIK-CAR.PSMA, CART-PSMA-TGFBRDN, P-PSMA-101; Glypican-3 (GPC3), such as TT-16, GLYCAR; Hemoglobin, such as PGN-236; Hepatocyte growth factor receptor, such as anti-cMet RNA CAR T; Human papillomavirus E7 protein, such as KITE-439; Immunoglobulin gamma Fc receptor III, such as ACTR087; IL-12, such as DC-RTS-IL-12; IL-12 agonist/mucin 16, such as JCAR-020; IL-13 alpha 2, such as MB-101; IL-2, such as CST-101; K-Ras GTPase, such as anti-KRAS G12V mTCR cell therapy; Neural cell adhesion molecule L1 LiCAM (CD171), such as JCAR-023; Latent membrane protein 1/Latent membrane protein 2, such as Ad5f35-LMPd1-2-transduced autologous dendritic cells; Melanoma associated antigen 10, such as MAGE-A10C796T MAGE-A10 TCR; Melanoma associated antigen 3/Melanoma associated antigen 6 (MAGE A3/A6) such as KITE-718; Mesothelin, such as CSG-MESO, TC-210; NKG2D, such as NKR-2; Ntrkrl tyrosine kinase receptor, such as JCAR-024; T cell receptors, such as BPX-701, IMCgp100; T-lymphocyte, such as TT-12; Tumor infiltrating lymphocytes, such as LN-144, LN-145; and Wilms tumor protein, such as JTCR-016, WT1-CTL.

Lymphoma or Leukemia Combination Therapy

In some embodiments, the additional therapeutic agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17-AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R-MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCl-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

In some embodiments, the additional therapeutic agents are suitable for treating non-Hodgkin's lymphomas (NHL), especially those of B cell origin, which include monoclonal antibodies, standard chemotherapy approaches (e.g., CHOP, CVP, FCM, MCP, and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include of atumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP, R-FCM, R-CVP, and R-MCP.

Examples of radioimmunotherapy for NHL/B-cell cancers include yttrium-90 ibritumomab tiuxetan (ZEVALIN) and iodine-131 tositumomab (BEXXAR®).

Mantle Cell Lymphoma Combination Therapy

In some embodiments, the additional therapeutic agents are suitable for treating mantle cell lymphoma (MCL), which include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

Other examples of therapeutic agents suitable for treating MCL include:

immunotherapy, such as monoclonal antibodies (like rituximab) and cancer vaccines, such as GTOP-99, which are based on the genetic makeup of an individual subject's tumor;

radioimmunotherapy, wherein a monoclonal antibody is combined with a radioisotope particle, such as iodine-131 tositumomab (BEXXAR®), yttrium-90 ibritumomab tiuxetan (ZEVALIN®), and BEXXAR® in sequential treatment with CHOP;

autologous stem cell transplantation coupled with high-dose chemotherapy, administering proteasome inhibitors such as bortezomib (VELCADE® or PS-341), or administering antiangiogenesis agents such as thalidomide, especially in combination with rituximab;

drugs that lead to the degradation of Bcl-2 protein and increase cancer cell sensitivity to chemotherapy, such as oblimersen, in combination with other chemotherapeutic agents;

mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents;

other agents such as flavopiridol, palbociclib (PD0332991), R-roscovitine (seliciclib, CYC202), styryl sulphones, obatoclax (GX15-070), TRAIL, Anti-TRAIL death receptors DR4 and DR5 antibodies, temsirolimus (TORISEL®, CCl-779), everolimus (RAD001), BMS- 345541, curcumin, SAHA, thalidomide, lenalidomide (REVLIMID®, CC-5013), and geldanamycin (17-AAG).

Waldenstrom's Macroglobulinemia Combination Therapy

In some embodiments, the additional therapeutic agents are suitable for treating Waldenstrom's Macroglobulinemia (WM), which include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Other examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma Combination Therapy

In some embodiments, the additional therapeutic agents are suitable for treating diffuse large B-cell lymphoma (DLBCL), which include cyclophosphamide, doxorubicin, vincristine, prednisone, anti-CD20 monoclonal antibodies, etoposide, bleomycin, many of the agents listed for WM, and any combination thereof, such as ICE and R-ICE.

Chronic Lymphocytic Leukemia Combination Therapy

In some embodiments, the additional therapeutic agents are suitable for treating chronic lymphocytic leukemia (CLL), which include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Myelofibrosis Combination Therapy

In some embodiments, the additional therapeutic agents are suitable for treating myelofibrosis, which include hedgehog inhibitors, histone deacetylase (HDAC) inhibitors, and tyrosine kinase inhibitors. Non-limiting examples of hedgehog inhibitors are saridegib and vismodegib.

Examples of HDAC inhibitors include, but are not limited to, pracinostat and panobinostat.

Non-limiting examples of tyrosine kinase inhibitors are lestaurtinib, bosutinib, imatinib, gilteritinib, radotinib, and cabozantinib.

Hyperproliferative Disease Combination Therapy

In some embodiments, the additional therapeutic agents are suitable for treating a hyperproliferative disease, which include gemcitabine, nab-paclitaxel, and gemcitabine/nab-paclitaxel with a JAK inhibitor and/or PI3K6 inhibitor.

Bladder Cancer Combination Therapy

In some embodiments, the additional therapeutic agents are suitable for treating bladder cancer, which include atezolizumab, carboplatin, cisplatin, docetaxel, doxorubicin, fluorouracil (5-FU), gemcitabine, idosfamide, Interferon alfa-2b, methotrexate, mitomycin, nab-paclitaxel, paclitaxel, pemetrexed, thiotepa, vinblastine, and any combination thereof.

Breast Cancer Combination Therapy

In some embodiments, the additional therapeutic agents are suitable for treating breast cancer, which include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof Triple Negative Breast Cancer Combination Therapy In some embodiments, the additional therapeutic agents are suitable for treating triple negative breast cancer, which include cyclophosphamide, docetaxel, doxorubicin, epirubicin, fluorouracil, paclitaxel, and combinations thereof.

Colorectal Cancer Combination Therapy

In some embodiments, the additional therapeutic agents are suitable for treating colorectal cancer, which include bevacizumab, capecitabine, cetuximab, fluorouracil, irinotecan, leucovorin, oxaliplatin, panitumumab, ziv-aflibercept, and any combinations thereof Castration-Resistant Prostate Cancer Combination Therapy In some embodiments, the additional therapeutic agents are suitable for treating castration-resistant prostate cancer, which include abiraterone, cabazitaxel, docetaxel, enzalutamide, prednisone, sipuleucel-T, and any combinations thereof Esophageal and Esophagogastric Junction Cancer Combination Therapy In some embodiments, the additional therapeutic agents are suitable for treating esophageal and esophagogastric junction cancer, which include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric Cancer Combination Therapy

In some embodiments, the additional therapeutic agents are suitable for treating gastric cancer, which include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof Head & Neck Cancer Combination Therapy In some embodiments, the additional therapeutic agents are suitable for treating head & neck cancer, which include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Hepatobiliary Cancer Combination Therapy

In some embodiments, the additional therapeutic agents are suitable for treating hepatobiliary cancer, which include capecitabine, cisplatin, fluoropyrimidine, 5-fluorourcil, gemcitabine, oxaliplatin, sorafenib, and any combinations thereof.

Hepatocellular Carcinoma Combination Therapy

In some embodiments, the additional therapeutic agents are suitable for treating hepatocellular carcinoma, which include capecitabine, doxorubicin, gemcitabine, sorafenib, and any combinations thereof.

Non-Small Cell Lung Cancer Combination Therapy

In some embodiments, the additional therapeutic agents are suitable for treating non-small cell lung cancer (NSCLC), which include afatinib, albumin-bound paclitaxel, alectinib, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.

Small Cell Lung Cancer Combination Therapy

In some embodiments, the additional therapeutic agents are suitable for treating small cell lung cancer (SCLC), which include bendamustine, carboplatin, cisplatin, cyclophosphamide, docetaxel, doxorubicin, etoposide, gemcitabine, ipilimumab, irinotecan, nivolumab, paclitaxel, temozolomide, topotecan, vincristine, vinorelbine, and any combinations thereof.

Melanoma Combination Therapy

In some embodiments, the additional therapeutic agents are suitable for treating melanoma, which include albumin bound paclitaxel, carboplatin, cisplatin, cobimetinib, dabrafenib, dacarbazine, IL-2, imatinib, interferon alfa-2b, ipilimumab, nitrosourea, nivolumab, paclitaxel, pembrolizumab, ipilimumab, temozolomide, trametinib, vemurafenib, vinblastine, and any combinations thereof.

Ovarian Cancer Combination Therapy

In some embodiments, the additional therapeutic agents are suitable for treating ovarian cancer, which include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcitabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Pancreatic Cancer Combination Therapy

In some embodiments, the additional therapeutic agents are suitable for treating pancreatic cancer, which include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof.

Renal Cell Carcinoma Combination Therapy

In some embodiments, the additional therapeutic agents are suitable for treating renal cell carcinoma, which include axitinib, bevacizumab, cabozantinib, erlotinib, everolimus, lenvatinib, nivolumab, pazopanib, sorafenib, sunitinib, temsirolimus, and any combinations thereof.

VIII. Kits

The present disclosure provides a kit comprising a compound of the present disclosure or a pharmaceutically acceptable salt thereof. The kit may further comprise instructions for use, e.g., for use in treating a viral infection. The instructions for use are generally written instructions, although electronic storage media (e.g., magnetic diskette or optical disk) containing instructions are also acceptable.

The present disclosure also provides a pharmaceutical kit comprising one or more containers comprising a compound of the present disclosure or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

Also provided are articles of manufacture comprising a unit dosage of a compound of the present disclosure or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

IX. Examples

Abbreviations as used herein have respective meanings as follows:

| | |
|---|---|
| Ac | Acetate |
| ACN | Acetonitrile |
| BippyPhos | 5-(di-tert-butylphosphino)-1',3',5'-triphenyl-1'H-[1,4']bipyrazole |
| Bn | Benzyl |
| br. s | Broad singlet |
| Bu | Butyl |
| dba | Dibenzylideneacetone |
| DCM | Dichloromethane |
| dd | Doublet of doublets |
| ddd | Doublet of doublet of doublets |
| DIPE | diisopropyl ether |
| DMF | Dimethylformamide |
| DMSO | Dimethylsulfoxide |
| dr | Diastereomeric ratio |
| DSC | Differential scanning calorimetry |
| DVS | Dynamic vapor sorption |
| ee | Enantiomeric excess |
| equiv | Equivalents |
| Et | Ethyl |
| EtOAc | Ethyl acetate |
| EtOH | Ethanol |
| ft | Foot (length) |
| g | Gram |
| GC | Gas chromatography |
| h | Hour |
| HBV | Hepatitis B virus |

| | |
|---|---|
| HCV | Hepatitis C virus |
| HFIPA | hexafluoroisopropanol |
| HIV | Human Immunodeficiency virus |
| HPLC | High-pressure liquid chromatography |
| IPA | Isopropyl alcohol |
| IPAc | Isopropyl acetate |
| iPr | Isopropyl |
| iProAc or IPAc | isopropyl acetate |
| kg | Kilogram |
| L | Liter |
| m | Multiplet |
| M | Molar |
| Me | Methyl |
| MEK | methyl ethyl ketone |
| MeOH | methanol |
| Me-THF | 2 methyl tetrahydrofuran |
| mg | Milligram |
| MHz | Mega hertz |
| MIBK | Methylisobutyl ketone |
| min | Minute |
| mL | Milliliter |
| mmol | Millimole |
| mol | Mole |
| MTBE | Methyl-tert-butyl ether |
| N | Normal |
| NLT | No less than |
| NMR | Nuclear magnetic resonance |
| Ph | Phenyl |
| RH | Relative humidity |
| s | Singlet |
| t-Bu | tert-Butyl |
| td | Triplet of doublets |
| Tf | Trifluoromethanesulfonate |
| TFE | trifluoroethanol |
| TGA | Thermogravimetric analysis |
| THF | Tetrahydrofuran |
| TMS | Trimethylsilyl |
| vol | Volume |
| wt | Weight |
| XRPD | X-ray powder diffraction |
| δ | Chemical shift |
| μL | Microliter |

The solid forms (polymorphs, solvates and hydrates) of Compound I were characterized by a variety of the following methods.

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640e) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

Differential Scanning Calorimetry (DSC) data were collected using a TA Instruments 2920 and Q2000 differential scanning calorimeter. Temperature calibration was performed using NIST-traceable indium metal. The sample was placed into a T zero aluminum DSC pan, covered with a lid and crimped. The weight was then accurately recorded. A weighed aluminum pan configured as the sample pan was placed on the reference side of the cell. The sample was heated from −30° C. to 250° C. at 10° C./minute.

Thermogravimetric Analysis (TGA) data were collected using a TA Instruments Discovery thermogravimetric analyzer. Temperature calibration was performed using nickel and Alumel™. Each sample was placed in an aluminum pan and inserted into the TG furnace. The furnace was heated under a nitrogen purge. The sample was heated from ambient to 350° C. at 10° C./minute.

Moisture sorption/desorption data were collected on a VTI SGA-100 Vapor Sorption Analyzer. NaCl and PVP were used as calibration standards. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Weight percentages reported in the data section are relative to the total sample mass introduced prior to equilibration at 5% RH as measured on the instrument.

Example 1. Preparation of Compound I

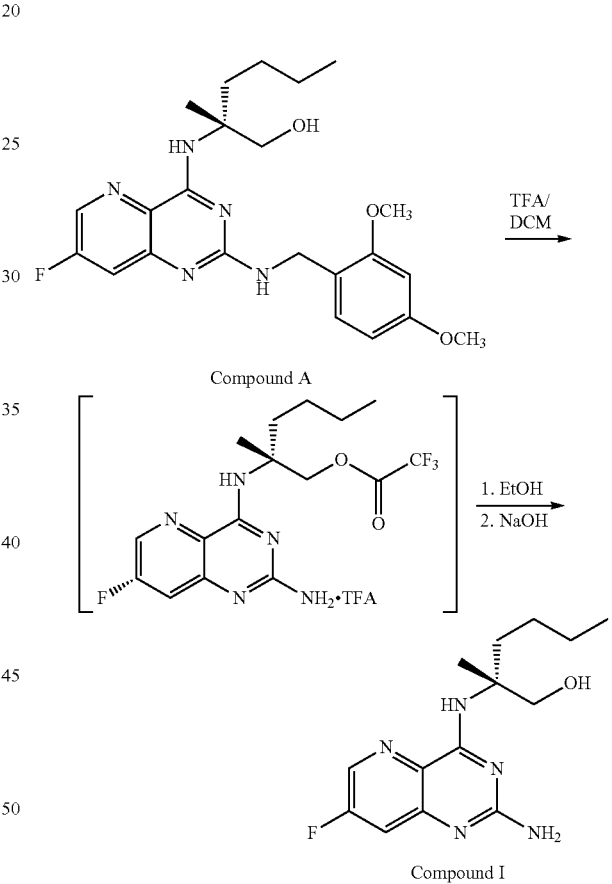

To a nitrogen flushed 50-L jacketed reactor was charged Compound A (2.69 kg, 6.07 moles, 1.0 equiv). This was followed by the addition of dichloromethane (10.13 L, 13.44 kg). Agitation was set to 175 RPM and the contents were agitated until a solution was observed. Trifluoroacetic acid (4.53 L, 6.75 kg) was charged at a rate such that the internal temperature did not exceed 35° C. (ca. 30 min.). After the addition of trifluoroacetic acid, the jacket was set to 46° C. (to maintain a gentle reflux). The contents were agitated at this temperature for 3 h and then the jacket was set to 15° C. Once the internal temperature reached 20° C., ethanol (denatured from n-heptane) (8.56 L, 6.75 kg) was charged and the contents were allowed to agitate at 20° C. for 14 h. After this amount of time, the heterogeneous contents were filtered through a benchtop poly-filter into a nitrogen flushed 100-L jacketed reactor.

Dichloromethane (5.21 L, 6.91 kg) was charged to the 50-L reactor and the solution was rinsed through the filter into the 100-L reactor. To the 100-L reactor was then charged water (15.5 L, 15.5 kg) and ethyl acetate (19.0 L, 17.0 kg). Agitation was set to 175 RPM and the jacket was set to 87° C. The contents were allowed to heat to reflux for 30 min. After this amount of time, the jacket was set to 20° C. The aqueous layer was discharged. To the reactor was charged water (18.4 L, 18.4 kg), and agitation was set to 200 RPM. 30% w/w NaOH (8.61 kg) was charged and the contents were agitated for 30 min. at 30° C. (jacket was set at 40° C.). Ethyl acetate (45.0 L, 40.4 kg) was then charged and the jacket was set to 55° C. Once the internal temperature reached 45° C., the contents were agitated at 200 RPM for 30 min. After this amount of time, agitation was stopped and the phases were allowed to separate and the aqueous layer was discharged. 4.5% w/w aqueous sodium bicarbonate (prepared from 605 g sodium bicarbonate and 12.8 kg water) solution was charged and the contents were agitated at 200 RPM at an internal temperature of 45° C. for 30 min. After this amount of time, agitation was stopped and the layers were allowed to separate. The aqueous layer was discharged and the jacket was set to 20° C. The contents were aged at this temperature under nitrogen for 14 h. The jacket was then set to 55° C. Once the internal temperature reached 45° C., 4.5% w/w aqueous sodium bicarbonate (prepared from 605 g sodium bicarbonate and 12.8 kg water) was charged and the contents were agitated (200 RPM) at 45° C. for 30 min. Agitation was then stopped, the phases were allowed to separate and the aqueous layer was discharged. 4.5% w/w aqueous sodium bicarbonate (prepared from 605 g sodium bicarbonate and 12.8 kg water). The contents were agitated (200 RPM) at 45° C. for 30 min. Agitation was then stopped, the phases were allowed to separate and the aqueous layer was discharged. Water (13.6 L, 13.6 kg) was added and the contents were agitated (150 RPM) at 45° C. for 30 min. After this amount of time, agitation was stopped and the phases were allowed to separate and the aqueous layer was discharged.

Example 2. Form I

The reactor was configured for vacuum distillation and the jacket was set to 70° C. and agitation was set to 150 RPM. The solvent was removed via vacuum distillation to ca. 30 L. The jacket was set to 35° C. and the reactor was backfilled with nitrogen. Ethyl acetate (45 L, 40.4 kg) was charged and the reactor was heated to 70° C., agitation was set to 150 RPM and the pressure was reduced. The solvent was removed via vacuum distillation to ca. 30 L. The jacket was set to 35° C. and the reactor was backfilled with nitrogen. The ethyl acetate distillation sequence was repeated as described 5 X. Final volumes for the five distillations were ca. 30 L after charging 45 L ethyl acetate for each sequence. The contents were sampled for water content (target <0.5% $H_2O$). After passing the water content criteria, the jacket was heated to 70° C., agitation was set to 150 RPM and the pressure was reduced and the distillation was continued to ca. 22 L. The jacket was set to 35° C. and the reactor was backfilled with nitrogen. Ethyl acetate (15 L, 13.5 kg) was charged and the contents were polish filtered through a 1.0 µm filter into the crystallizer. The jacket on the crystallizer was set to 70° C. and agitation was set to 150 RPM. The pressure of the vessel was reduced and the distillation was continued to ca. 18 L. Once this target volume was reached, the crystallizer was backfilled with nitrogen and the jacket was set to 87° C. Ethyl acetate (9.5 L, 8.5 kg) was charged and the contents were agitated until a homogenous solution was observed. After all solids dissolved, a cooling ramp from 85° C. to 20° C. over 8 h was initiated.

The solids were filtered and the wet-cake was washed with ethyl acetate (6.1 L, 5.5 kg). The jacket on the filter was set to 46° C. and the contents were dried for 24 h under reduced pressure with a nitrogen bleed. Compound I (Form I) was isolated in good purity (99.6% Assay, 99.7% AN).

Optionally, Compound I (1.2 kg, 4.0 mol) was charged to a 50-L jacketed reactor followed by ethyl acetate (25 L, 22 kg). The jacket on the reactor was set to 87° C. and agitation was set to 150 RPM. The contents were agitated until a solution was observed. After all solids dissolved, a cooling ramp from 85° C. to 20° C. over 8 h was initiated. The solids were filtered and the wet-cake was washed with ethyl acetate (6.1 L, 5.5 kg). The jacket on the filter was set to 46° C. and the contents were dried for 24 h under reduced pressure with a nitrogen bleed. Compound I was isolated.

Form I is an unsolvated phase. Its XRPD pattern is shown in FIG. 1.

TABLE 1

Crystal Data and Data Collection Parameters for Compound I Form I

| | |
|---|---|
| Empirical formula | $C_{14}H_{20}FN_5O$ |
| Formula weight | 293.35 |
| Temperature | 100(2) K |
| Wavelength | 1.54178 Å |
| Crystal system | Tetragonal |
| Space group | $P4_1$ |
| Unit cell dimensions | a = 8.0344(2) Å   $\alpha$ = 90° |
| | b = 8.0344(2) Å   $\beta$ = 90° |
| | c = 23.7871(7) Å   $\gamma$ = 90° |
| Volume | 1535.49(9) Å$^3$ |
| Z | 4 |
| Density (calculated) | 1.269 Mg/m$^3$ |
| Absorption coefficient | 0 766 mm$^{-1}$ |
| F(000) | 624 |
| Crystal size | 0.450 × 0.320 × 0.290 mm$^3$ |
| Theta range for data collection | 5.506 to 71.991° |
| Index ranges | −9 <= h <= 9, −9 <= k <= 9, −27 <= l <= 28 |
| Reflections collected | 36463 |
| Independent reflections | 2954 [R(int) = 0.0397] |
| Completeness to theta = 67.679° | 99.4% |
| Refinement method | Full-matrix least-squares on F$^2$ |
| Data/restraints/parameters | 2954/1/203 |
| Goodness-of-fit on F$^2$ | 1.219 |
| Final R indices [I > 2sigma(I)] | R1 = 0.0339, wR2 = 0.0824 |
| R indices (all data) | R1 = 0.0341, wR2 = 0.0827 |
| Absolute structure parameter | Flack parameter: 0.12(4) |
| | Hooft parameter: 0.10(4) |
| Extinction coefficient | 0.0098(8) |
| Largest diff. peak and hole | 0.146 and −0.147 e · Å$^{-3}$ |

TABLE 2

Peak Table for Form I

| Pos. [°2θ] | Rel. Int. [%] |
|---|---|
| 10.9 | 42.72 |
| 11.5 | 17.57 |
| 13.2 | 47.27 |
| 14.7 | 38.18 |
| 15.5 | 53.84 |
| 15.6 | 39.90 |

TABLE 2-continued

Peak Table for Form I

| Pos. [°2θ] | Rel. Int. [%] |
|---|---|
| 18.4 | 2.21 |
| 19.0 | 8.77 |
| 21.4 | 66.66 |
| 21.9 | 100.00 |
| 22.3 | 5.33 |
| 23.2 | 30.44 |
| 24.2 | 4.77 |
| 24.6 | 6.37 |
| 24.9 | 26.03 |
| 25.7 | 8.09 |
| 26.5 | 4.13 |
| 27.0 | 11.23 |
| 28.8 | 2.99 |
| 29.7 | 3.56 |
| 30.4 | 3.53 |
| 30.9 | 1.12 |
| 31.8 | 3.44 |
| 33.2 | 4.08 |
| 34.0 | 4.63 |
| 34.7 | 4.13 |
| 35.4 | 3.16 |
| 36.1 | 4.79 |
| 38.2 | 3.29 |
| 39.1 | 3.36 |

Example 3. Gentisic Acid

Compound I Form I (37.01 mg), approximately one molar equivalent of gentisic acid (18.1 mg), and acetonitrile (300 µl) were heated to 50° C. in an Avantium Crystal16@ multiple-reactor system. After approximately 15 minutes, the reactor system was turned off for fast cooling to ambient temperature. After reaching ambient temperature, samples were re-heated to about 50° C. for about 4 hours and then cooled to about 10° C. at 0.1° C./min. Solids were collected by vacuum filtration, added to dichloromethane (0.5 ml), and stirred at ambient temperature. After about 5 hours, solids were collected by vacuum filtration and analyzed.

Compound I Gentisic Acid XRPD Pattern is Shown in FIG. 2.

TABLE 3

Peak Table for Gentisic Acid

| Pos. [°2Th.] | Rel. Int. [%] |
|---|---|
| 4.4 | 100.00 |
| 8.7 | 72.12 |
| 12.3 | 1.88 |
| 12.9 | 10.71 |
| 13.9 | 2.00 |
| 14.4 | 1.57 |
| 14.9 | 15.64 |
| 16.3 | 4.01 |
| 17.3 | 4.71 |
| 18.9 | 3.58 |
| 19.5 | 6.04 |
| 20.5 | 3.38 |
| 21.7 | 1.94 |
| 22.2 | 0.99 |
| 23.0 | 2.82 |
| 24.8 | 14.51 |
| 25.7 | 7.28 |
| 26.3 | 5.81 |
| 27.1 | 3.43 |
| 27.7 | 1.53 |
| 33.1 | 0.10 |
| 39.4 | 0.87 |

The DSC curve is shown in FIG. 3 and displays one endothermic transition at about 178° C. The TGA curve is shown in FIG. 4 and indicates that the phase is unsolvated. The dynamic vapor sorption curve is shown in FIG. 5 and the data indicates that the form absorbs about 1.1% of water up to 95% RH at 25° C. The material was found to not have changed forms post experiment.

Example 4. Hippuric Acid

Compound I Form I (40.09 mg), approximately one molar equivalent of hippuric acid (24.5 mg), and acetone (300 µl) were heated to about 50° C. in an Avantium Crystal16 multiple-reactor system. After approximately 15 minutes, the reactor system was turned off for fast cooling to ambient temperature. After reaching ambient temperature, samples were re-heated to about 50° C. for about 4 hours and then cooled to about 10° C. at 0.1° C./min. Solids were collected by vacuum filtration and analyzed.

Compound I Hippuric Acid XRPD pattern is shown in FIG. 6.

TABLE 4

Peak Table for Hippuric Acid

| Pos. [°2Th.] | Rel. Int. [%] |
|---|---|
| 2.9 | 9.03 |
| 5.0 | 100.00 |
| 7.6 | 8.23 |
| 10.4 | 3.52 |
| 12.6 | 11.30 |
| 14.6 | 1.07 |
| 17.6 | 3.41 |
| 18.1 | 1.74 |
| 19.0 | 6.51 |
| 20.3 | 3.61 |
| 25.2 | 28.94 |
| 25.6 | 5.54 |
| 26.3 | 3.35 |
| 26.7 | 2.49 |
| 27.2 | 2.27 |
| 27.9 | 1.49 |
| 28.5 | 4.96 |
| 29.2 | 1.51 |

The DSC curve is shown in FIG. 7 and displays one endothermic transition at about 127° C. The TGA curve is shown in FIG. 8 and indicates that the phase is unsolvated. The dynamic vapor sorption curve is shown in FIG. 9 and the data indicates that the form absorbs about 0.68% of water up to 95% RH at 25° C. The material was found to not have changed forms post experiment.

Example 5. Phosphoric Acid Form I

Compound I Phosphate Form I was isolated by dissolving Compound I Form I (39.14 mg) and 2 molar equivalents of phosphoric acid (18 µl, 85% aqueous) in acetone (300 µl). A gel resulted from the reaction and was triturated with various solvents including ethyl acetate, diethyl ether and ultimately a mixture of acetonitrile and isopropanol (67/33 v/v, 300 µl). Solids resulted after stirring for about 5 days at ambient temperature in the acetonitrile/isopropanol mixture. Solids were collected by vacuum filtration and the wet cake was washed with isopropanol (100 µl).

Compound I Phosphoric Acid Form I XRPD pattern is shown in FIG. 10.

TABLE 5

Peak Table for Phosphoric Acid Form I

| Pos. [°2Th.] | Rel. Int. [%] |
|---|---|
| 3.7 | 100.00 |
| 6.1 | 86.20 |
| 7.1 | 45.11 |
| 12.1 | 13.70 |
| 14.2 | 16.17 |
| 18.8 | 8.77 |
| 21.6 | 16.10 |
| 24.0 | 9.08 |
| 27.4 | 32.26 |
| 28.2 | 16.79 |

The DSC curve is shown in FIG. 11 and displays several endothermic transitions at about 43, 118, and 202° C. The TGA curve is shown in FIG. 12 and indicates that the phase is solvated. This form was not further characterized.

Example 6. Phosphoric Acid Form II

Compound I Phosphate Material II was isolated by cooling Compound I Form I (53.00 mg) and 1 molar equivalent of phosphoric acid (13 μl, 85% aqueous) in isopropanol (500 μl). Note that purple discoloration was observed upon the addition of phosphoric acid into the mixture of Compound I and isopropanol, but turned clear upon mixing. A gel resulted from the reaction, and was triturated with various solvents including acetonitrile, diethyl ether and acetonitrile/isopropanol (67/33 v/v). Solids were crystallized by slurrying the gel in diethyl ether (1 ml) and adding seeds of Compound I Phosphate Form I. Solids were isolated by vacuum filtration after stirring for about 3 days.

Compound I Phosphoric Acid Form II XRPD pattern is shown in FIG. 13.

TABLE 6

Peak Table for Phosphoric Acid Form II

| Pos. [°2Th.] | Rel. Int. [%] |
|---|---|
| 5.4 | 86.78 |
| 6.3 | 100.00 |
| 10.4 | 7.13 |
| 11.5 | 4.54 |
| 13.6 | 6.08 |
| 15.4 | 6.17 |
| 15.8 | 14.48 |
| 16.3 | 7.56 |
| 18.1 | 18.65 |
| 18.5 | 6.00 |
| 18.9 | 21.75 |
| 20.6 | 12.08 |
| 21.4 | 6.04 |
| 22.4 | 3.94 |
| 23.6 | 6.50 |
| 23.8 | 8.09 |
| 24.1 | 10.39 |
| 26.0 | 1.56 |
| 26.7 | 22.49 |
| 27.4 | 11.38 |
| 28.7 | 3.62 |
| 29.2 | 2.37 |
| 31.5 | 2.31 |
| 32.4 | 2.96 |

The DSC curve is shown in FIG. 14 and displays two endothermic transitions at about 42 and 95° C. The TGA curve is shown in FIG. 15 and indicates that the phase is solvated. This form was not further characterized.

Example 7. Succinic Acid

Compound I Form I (35.7 mg) and approximately half a molar equivalent of succinic acid (7.54 mg) was dissolved in isopropanol (0.5 ml) at approximately 60° C. in a Mettler-Toledo EasyMax Synthesis Workstation. The solution was cooled to about 5° C. over approximately 9 hours. Solids were collected by vacuum filtration, air dried for approximately 10 minutes, and analyzed.

Compound I Succinic Acid XRPD pattern is shown in FIG. 16.

TABLE 7

Peak Table for Succinic Acid

| Pos. [°2Th.] | Rel. Int. [%] |
|---|---|
| 4.6 | 19.38 |
| 6.8 | 100.00 |
| 9.3 | 36.09 |
| 12.7 | 3.55 |
| 13.2 | 8.09 |
| 13.6 | 4.77 |
| 14.1 | 5.61 |
| 14.9 | 5.69 |
| 15.8 | 6.68 |
| 17.5 | 10.00 |
| 18.2 | 4.60 |
| 18.7 | 16.13 |
| 19.0 | 14.47 |
| 19.3 | 6.42 |
| 19.7 | 4.79 |
| 20.7 | 7.51 |
| 21.3 | 5.50 |
| 22.0 | 4.99 |
| 22.5 | 5.25 |
| 23.0 | 8.23 |
| 25.7 | 19.51 |
| 27.0 | 7.81 |
| 27.4 | 2.60 |
| 28.3 | 2.18 |
| 28.7 | 2.77 |
| 30.1 | 1.75 |
| 36.4 | 2.43 |

The DSC curve is shown in FIG. 17 and displays two endothermic transitions at about 96 and 115° C. The TGA curve is shown in FIG. 18 and indicates that the phase is unsolvated. The dynamic vapor sorption curve is shown in FIG. 19 and the data indicates that the form absorbs about 1.2% of water up to 95% RH at 25° C. The material was found to not have changed forms post experiment.

Example 8. Ethanedisulfonic Acid Form I

Ethanedisulfonic Acid Form I was isolated from a cooling experiment in acetone. In one experiment, Compound I Form I (34.19 mg), approximately one molar equivalent of 1,2-ethanedisulfonic acid hydrate (27.3 mg), and acetone (300 μl) were heated to about 50° C. in an Avantium Crystal16® multiple-reactor system. After approximately 15 minutes, the reactor system was turned off for fast cooling to ambient temperature. After reaching ambient temperature, samples were re-heated to about 50° C. for about 4 hours and then cooled to about 10° C. at 0.1° C./min. Solids were collected by vacuum filtration and analyzed.

Compound I Ethanedisulfonic Acid Form I XRPD pattern is shown in FIG. 20.

TABLE 8

| Peak Table for Ethanedisulfonic Acid Form I | |
|---|---|
| Pos. [°2Th.] | Rel. Int. [%] |
| 4.4 | 35.07 |
| 7.9 | 18.17 |
| 8.7 | 34.95 |
| 9.5 | 13.63 |
| 11.0 | 4.33 |
| 12.5 | 13.87 |
| 13.0 | 27.50 |
| 13.3 | 18.20 |
| 16.2 | 12.07 |
| 16.6 | 15.51 |
| 18.0 | 7.15 |
| 18.3 | 14.71 |
| 19.4 | 5.11 |
| 20.0 | 18.66 |
| 20.6 | 18.20 |
| 21.1 | 23.42 |
| 21.4 | 5.31 |
| 22.1 | 100.00 |
| 22.3 | 36.92 |
| 23.4 | 13.75 |
| 23.7 | 8.93 |
| 24.1 | 6.11 |
| 24.9 | 4.91 |
| 26.0 | 13.56 |
| 26.9 | 4.30 |
| 28.4 | 3.97 |
| 29.9 | 12.63 |
| 30.6 | 8.80 |
| 38.4 | 2.24 |

Example 9. Ethanedisulfonic Acid Form II

Compound I Ethanedisulfonic aciform II was isolated by slurrying Form I in dichloromethane. Compound I Edisylate Form II was also isolated from a cooling experiment in acetone. The procedure involved dissolving Compound I Form I (32.10 mg) in acetone (800 μl) at approximately 60° C. in a Mettler-Toledo EasyMax reactor. 1,2-ethanesulfonic acid hydrate (1.1 molar equivalents, 26.05 mg) was added to the solution, and a dark purple solution resulted. The solution was cooled to about 20° C. over approximately 6.5 hours.

Compound I Ethanedisulfonic Acid Form II XRPD pattern is shown in FIG. 21.

TABLE 9

| Peak Table for Ethanedisulfonic Acid Form II | |
|---|---|
| Pos. [°2Th.] | Rel. Int. [%] |
| 4.5 | 100.00 |
| 5.6 | 5.00 |
| 8.4 | 25.24 |
| 9.2 | 19.22 |
| 11.7 | 2.28 |
| 12.9 | 15.31 |
| 13.4 | 9.50 |
| 14.9 | 1.79 |
| 16.6 | 24.61 |
| 17.3 | 4.83 |
| 17.9 | 11.71 |
| 18.3 | 13.46 |
| 19.4 | 3.82 |
| 21.0 | 3.01 |
| 22.2 | 31.30 |
| 24.2 | 14.40 |
| 26.0 | 5.90 |
| 27.2 | 7.37 |

Although the foregoing disclosure has been described in some detail by way of illustration and example for purposes of clarity of understanding, one of skill in the art will appreciate that certain changes and modifications may be practiced within the scope of the appended claims. In addition, each reference, including all of the U.S. patents, U.S. patent application publications, U.S. patent applications, foreign patents, foreign patent applications and non-patent publications referred to in this specification are incorporated herein by reference, in their entirety, to the extent not inconsistent with the present description. Where a conflict exists between the instant application and a reference provided herein, the instant application shall dominate.

What is claimed is:

1. A crystalline form of (R)-2-((2-amino-7-fluoropyrido[3,2-d]pyrimidin-4-yl)amino)-2-methylhexan-1-ol gentisic acid:

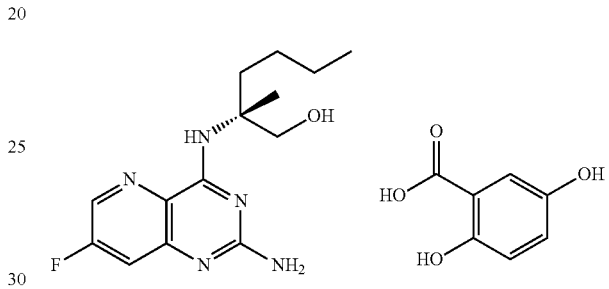

characterized by an X-ray powder diffraction (XRPD) pattern comprising three or more peaks at 4.4°, 8.7°, 12.9°, 14.9°, 17.3°, 19.5°, 24.8°, 25.7°, or 26.3° 2θ (±0.2° 2θ), Compound I gentisic acid.

2. The crystalline form of claim 1, characterized by an XRPD pattern comprising four or more peaks at 4.4°, 8.7°, 12.9°, 14.9°, 17.3°, 19.5°, 24.8°, 25.7°, or 26.3° 2θ (±0.2° 2θ).

3. The crystalline form of claim 1, characterized by an XRPD pattern comprising peaks at 4.4°, 8.7°, and 14.9° 2θ (±0.2° 2θ).

4. The crystalline form of claim 3, wherein the XRPD pattern further comprises one or more additional peaks at 12.9°, 17.3°, 19.5°, 24.8°, 25.7°, or 26.3° 2θ (±0.2° 2θ).

5. The crystalline form of claim 3, wherein the XRPD pattern further comprises two or more additional peaks at 12.9°, 17.3°, 19.5°, 24.8°, 25.7°, or 26.3° 2θ (±0.2° 2θ).

6. The crystalline form of claim 1, characterized by an XRPD pattern comprising peaks at 12.9°, 24.8°, and 25.7° 2θ (±0.2° 2θ).

7. The crystalline form of claim 6, wherein the XRPD pattern further comprises one or more additional peaks at 4.4°, 8.7°, 14.9°, 17.3°, 19.5°, or 26.3° 2θ (±0.2° 2θ).

8. The crystalline form of claim 6, wherein the XRPD pattern further comprises two or more additional peaks at 4.4°, 8.7°, 14.9°, 24.8°, or 26.3° 2θ (±0.2° 2θ).

9. The crystalline form of claim 1, characterized by an XRPD pattern comprising peaks at 4.4°, 8.7°, 12.9°, 14.9°, 17.3°, 19.5°, 24.8°, 25.7°, and 26.3° 2θ (±0.2° 2θ).

10. The crystalline form of claim 1, characterized by an XRPD pattern substantially as shown in FIG. 2.

11. The crystalline form of claim 1, characterized by a differential scanning calorimetry (DSC) thermogram having an endotherm with an onset of about 178° C.

12. The crystalline form of claim 1, characterized by a DSC thermogram substantially as shown in FIG. 3.

13. A crystalline form of (R)-2-((2-amino-7-fluoropyrido[3,2-d]pyrimidin-4-yl)amino)-2-methylhexan-1-ol hippuric acid:

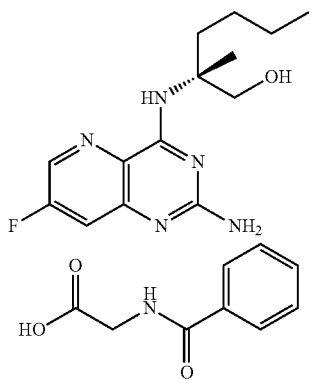

characterized by an XRPD pattern comprising three or more peaks at 2.9°, 5.0°, 7.6°, 10.4°, 12.6°, 17.6°, 19.0°, 25.2°, or 28.5° 2θ (±0.2° 2θ), Compound I hippuric acid.

14. A crystalline form of (R)-2-((2-amino-7-fluoropyrido[3,2-d]pyrimidin-4-yl)amino)-2-methylhexan-1-ol phosphoric acid:

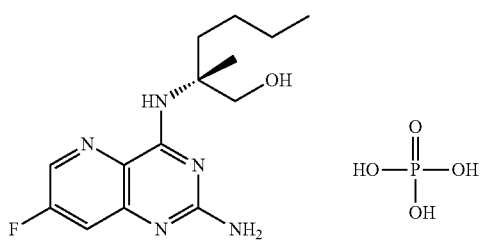

characterized by an XRPD pattern comprising three or more peaks at 3.7°, 6.1°, 7.1°, 12.1°, 14.2°, 21.6°, 24.0°, 27.4°, or 28.2° 2θ (±0.2° 2θ), phosphate salt Form I.

15. A crystalline form of (R)-2-((2-amino-7-fluoropyrido[3,2-d]pyrimidin-4-yl)amino)-2-methylhexan-1-ol phosphoric acid:

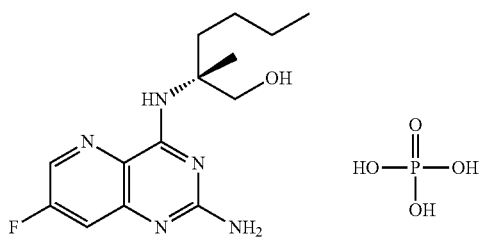

characterized by an XRPD pattern comprising three or more peaks at 5.4°, 6.3°, 15.8°, 18.1°, 18.9°, 20.6°, 24.1°, 26.7°, or 27.4° 2θ (±0.2° 2θ), phosphate salt Form II.

16. A crystalline form of (R)-2-((2-amino-7-fluoropyrido[3,2-d]pyrimidin-4-yl)amino)-2-methylhexan-1-ol succinic acid:

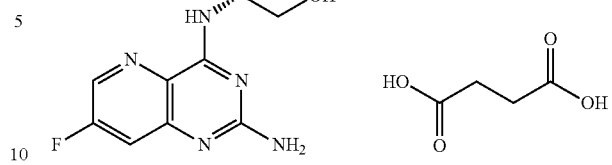

characterized by an XRPD pattern comprising three or more peaks at 4.6°, 6.8°, 9.3°, 13.2°, 17.5°, 18.7°, 19.0°, 25.7°, or 27.0° 2θ (±0.2° 2θ), Compound I succinic acid.

17. A crystalline form of (R)-2-((2-amino-7-fluoropyrido[3,2-d]pyrimidin-4-yl)amino)-2-methylhexan-1-ol ethanedisulfonic acid:

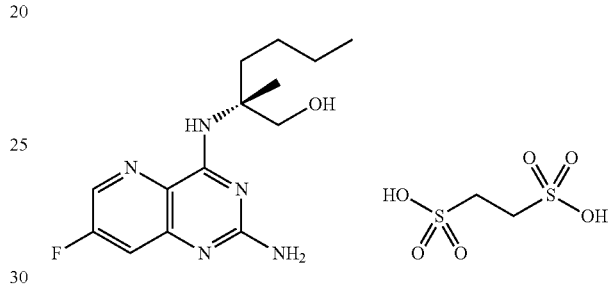

characterized by an XRPD pattern comprising three or more peaks at 4.4°, 7.9°, 8.7°, 13.0°, 16.6°, 20.6°, 21.1°, 22.1°, or 26.0° 2θ (±0.2° 2θ), Compound I ethanedisulfonic acid Form I.

18. A crystalline form of (R)-2-((2-amino-7-fluoropyrido[3,2-d]pyrimidin-4-yl)amino)-2-methylhexan-1-ol ethanedisulfonic acid:

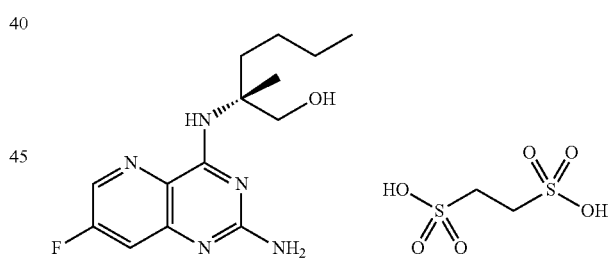

characterized by an XRPD pattern comprising three or more peaks at 4.5°, 5.6°, 8.4°, 12.9°, 13.4°, 16.6°, 17.9°, 18.3°, or 22.2° 2θ (±0.2° 2θ), Compound I ethanedisulfonic acid Form II.

19. A pharmaceutical composition comprising the crystalline form of claim 1 and one or more pharmaceutically acceptable excipients.

20. The pharmaceutical composition of claim 19, wherein the crystalline form is the gentisate salt.

21. A method of treating or preventing a hepatitis B virus (HBV) infection in a subject in need thereof, comprising administering to the subject a therapeutically effective amount of the crystalline form of claim 1, or the pharmaceutical composition of claim 19.

22. The method of claim 21, further comprising administering a therapeutically effective amount of one or more additional therapeutic agents.

23. The method of claim 21, wherein the one or more additional therapeutic agents are administered simultaneously with the crystalline form or the pharmaceutical composition.

24. The method of claim 21, wherein the one or more additional therapeutic agents are selected from the group consisting of: HBV combination drugs, HBV vaccines, HBV DNA polymerase inhibitors, immunomodulators, toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucleotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2,3-dioxygenase (IDO) pathway inhibitors, PD-1 inhibitors, PD-L1 inhibitors, recombinant thymosin alpha-1 agonists, Bruton's tyrosine kinase (BTK) inhibitors, KDM inhibitors, HBV replication inhibitors, arginase inhibitors, and other HBV drugs.

25. The method of claim 21, wherein the one or more additional therapeutic agents are selected from the group consisting of: adefovir, tenofovir disoproxil fumarate+ emtricitabine, tenofovir disoproxil fumarate, entecavir, lamivudine, tenofovir alafenamide, tenofovir, tenofovir disoproxil, tenofovir alafenamide fumarate, tenofovir alafenamide hemifumarate, telbivudine, emtricitabine, peginterferon alfa-2b, interferon alpha 1b, interferon alpha 2b, pegylated interferon alpha-2a, interferon alfa-n1, ribavirin, interferon beta-1a, Bioferon, Ingaron, Inmutag, Algeron, Roferon-A, Oligotide, Zutectra, Shaferon, interferon alfa-2b, Alfaferone, interferon alfa-2b, Feron, interferon-alpha 2, Bevac, Laferonum, Vipeg, Blauferon-B, Blauferon-A, Intermax Alpha, Realdiron, Lanstion, Pegaferon, PDferon-B, alfainterferona 2b, Kalferon, Pegnano, Feronsure, PegiHep, Optipeg A, Realfa 2B, Reliferon, peginterferon alfa-2b, Reaferon-EC, Proquiferon, Uniferon, Urifron, interferon alfa-2b, Anterferon, Shanferon, MOR-22, interleukin-2 (IL-2), recombinant human interleukin 2, Layfferon, Ka Shu Ning, Shang Sheng Lei Tai, Intefen, Sinogen, Fukangtai, Alloferon and celmoleukin.

26. The method of claim 21, wherein the one or more additional therapeutic agents are selected from the group consisting of: entecavir, adefovir, tenofovir disoproxil fumarate, tenofovir alafenamide, tenofovir, tenofovir disoproxil, tenofovir alafenamide fumarate, tenofovir alafenamide hemifumarate, telbivudine and lamivudine.

27. The method of claim 21, wherein the one or more additional therapeutic agents are selected from the group consisting of tenofovir alafenamide, tenofovir alafenamide fumarate, and tenofovir alafenamide hemifumarate.

* * * * *